US012629406B2

(12) United States Patent (10) Patent No.: US 12,629,406 B2
Gulati et al. (45) Date of Patent: May 19, 2026

(54) ALTERATIONS IN ENDOTHELIN RECEPTORS FOLLOWING HEMORRHAGE AND RESUSCITATION BY CENTHAQUIN

(71) Applicants: MIDWESTERN UNIVERSITY, Downers Grove, IL (US); Pharmazz, Inc., Willowbrook, IL (US)

(72) Inventors: Anil Gulati, Naperville, IL (US); Manish Lavhale, Amravati (IN); Bhawna Katia, Bathinda (IN); Abhishek Kumar Singh, Bareilly (IN)

(73) Assignees: MIDWESTERN UNIVERSITY, Downers Grove, IL (US); Pharmazz, Inc., Willowbrook, IL (US)

( * ) Notice: Subject to any disclaimer, the term of this patent is extended or adjusted under 35 U.S.C. 154(b) by 761 days.

(21) Appl. No.: 17/052,473

(22) PCT Filed: May 3, 2019

(86) PCT No.: PCT/US2019/030652
§ 371 (c)(1),
(2) Date: Nov. 2, 2020

(87) PCT Pub. No.: WO2019/213558
PCT Pub. Date: Nov. 7, 2019

(65) Prior Publication Data
US 2021/0169978 A1 Jun. 10, 2021

Related U.S. Application Data

(60) Provisional application No. 62/666,675, filed on May 3, 2018.

(30) Foreign Application Priority Data

May 25, 2018 (IN) .............................. 201841019588

(51) Int. Cl.
*A61K 38/17* (2006.01)
*A61K 31/496* (2006.01)
*A61P 13/12* (2006.01)

(52) U.S. Cl.
CPC ........ *A61K 38/1709* (2013.01); *A61K 31/496* (2013.01); *A61P 13/12* (2018.01)

(58) Field of Classification Search
None
See application file for complete search history.

(56) References Cited

U.S. PATENT DOCUMENTS

| | | | |
|---|---|---|---|
| 3,954,987 A | 5/1976 | Simpson |
| 3,983,121 A | 9/1976 | Murthi et al. |
| 4,088,659 A | 5/1978 | Bhat et al. |
| 4,761,417 A | 8/1988 | Maroko |
| 5,055,470 A | 10/1991 | Boissard et al. |
| 5,922,681 A | 7/1999 | Doherty et al. |
| 6,369,114 B1 | 4/2002 | Weil et al. |
| 6,372,226 B2 | 4/2002 | Aoki et al. |
| 6,545,048 B1 | 4/2003 | Patterson et al. |
| 7,030,082 B2 | 4/2006 | Soltero et al. |
| 8,623,823 B2 | 1/2014 | Gulati |
| 8,980,874 B2 | 3/2015 | Gulati |
| 9,493,524 B2 | 11/2016 | Gulati |
| 10,112,981 B2 | 10/2018 | Gulati |
| 10,561,704 B2 | 2/2020 | Gulati |
| 10,828,368 B2 | 11/2020 | Gulati |
| 2002/0082285 A1 | 6/2002 | Lebwohl |
| 2003/0100507 A1 | 5/2003 | Gulati |
| 2003/0104976 A1 | 6/2003 | Davar et al. |
| 2003/0232787 A1 | 12/2003 | Dooley |
| 2003/0236235 A1 | 12/2003 | Gulati |
| 2004/0044008 A1 | 3/2004 | Daugan et al. |
| 2004/0063719 A1 | 4/2004 | Adams et al. |
| 2004/0138121 A1 | 7/2004 | Gulati |
| 2004/0176274 A1 | 9/2004 | Davar et al. |
| 2006/0079553 A1 | 4/2006 | Hargreaves et al. |
| 2007/0066568 A1 | 3/2007 | Dalton et al. |
| 2010/0004166 A1 | 1/2010 | Pittner et al. |
| 2010/0189802 A1 | 7/2010 | Childs et al. |
| 2010/0209433 A1 | 8/2010 | Bergmann et al. |
| 2011/0312936 A1 | 12/2011 | Lanter et al. |
| 2012/0083447 A1 | 4/2012 | Gulati |
| 2012/0093798 A1 | 4/2012 | Gulati |
| 2012/0308644 A1 | 12/2012 | Bromley et al. |

(Continued)

FOREIGN PATENT DOCUMENTS

| | | |
|---|---|---|
| CN | 102458399 A | 5/2012 |
| DE | 2421382 A1 | 11/1975 |

(Continued)

OTHER PUBLICATIONS

Agrawal M and Swartz R "Acute Renal Failure" Am. Fam. Physician 61:2077-2088. (Year: 2000).*
Salman et al. "Resuscitative Effect of Centhaquin on Renal Medullary Blood Flow in a Rat Model of Hemorrhagic Shock" Crit. Care Med. 47:740. (Year: 2019).*
Ranjan et al. "Abstract 13767: Centhaquin Attenuates Acute Kidney Injury Following Hemorrhagic Shock" Circulation 140:A13767. (Year: 2019).*
Gulati et al. "Abstract 20622: Endothelin Receptor Alteration Following Hemorrhagic Shock and Resuscitation by Centhaquin" Ciculation 136:A20622. (Year: 2017).*
Reniguntala et al. "Synthesis and Characterization of Centhaquin and its Citrate Salt and a Comparative Evaluation of their Cardiovascular Actions" Drug Res 65:184-191. (Year: 2015).*

(Continued)

*Primary Examiner* — Sudhakar Katakam
*Assistant Examiner* — Zachary J Miknis
(74) *Attorney, Agent, or Firm* — MARSHALL, GERSTEIN & BORUN LLP

(57) ABSTRACT

The present disclosure is related to methods and compositions for treating or preventing kidney injury or failure, comprising administering an endothelin B ($ET_B$) receptor agonist and/or an $\alpha_2$ adrenergic agent.

15 Claims, 19 Drawing Sheets

Specification includes a Sequence Listing.

(56) References Cited

U.S. PATENT DOCUMENTS

| | | | |
|---|---|---|---|
| 2013/0296331 A1 | 11/2013 | Abassi et al. | |
| 2015/0148398 A1 | 5/2015 | Attali et al. | |
| 2015/0250782 A1 | 9/2015 | Gulati et al. | |
| 2016/0151450 A1 | 6/2016 | Gulati | |
| 2018/0085461 A1* | 3/2018 | Gulati | A61P 43/00 |

FOREIGN PATENT DOCUMENTS

| | | |
|---|---|---|
| EP | 0126327 A1 | 11/1984 |
| EP | 0410114 A2 | 1/1991 |
| EP | 2890376 B1 | 9/2017 |
| JP | 50-149692 A | 11/1975 |
| JP | 60-006612 A | 1/1985 |
| JP | 2010-536868 A | 12/2010 |
| JP | 2012-502952 A | 2/2012 |
| WO | 92/19644 A1 | 11/1992 |
| WO | 02/43654 A2 | 6/2002 |
| WO | 03/09805 A2 | 2/2003 |
| WO | 2004/037235 A2 | 5/2004 |
| WO | 2004/045592 A2 | 6/2004 |
| WO | 2008/043102 A2 | 4/2008 |
| WO | 2008/122020 A1 | 10/2008 |
| WO | 2008/124803 A1 | 10/2008 |
| WO | 2009/026282 A2 | 2/2009 |
| WO | 2009/026828 A1 | 3/2009 |
| WO | 2010/127096 A2 | 11/2010 |
| WO | 2010/127197 A2 | 11/2010 |
| WO | 2012/138043 A2 | 10/2012 |
| WO | 2014/035446 A1 | 3/2014 |
| WO | 2015/006324 A2 | 1/2015 |
| WO | 2019/213558 A1 | 11/2019 |

OTHER PUBLICATIONS

Briyal et al. Alterations in Endothelin Receptors Following Hemorrhage and Resuscitation by Centhaquin, Physiological Research, 67:199-214 (2018).

Briyal et al., "IRL-1620 prevents beta amyloid (A ) induced oxidative stress and cognitive impairment," Journal of Clinical PHarmacology 51(9):1349, Abstract No. 1123022 (2011).

Briyal, et al. "Effect of combination of endothelin receptor antagonist (TAK-044) and aspirin in middle cerebral artery occlusion model of acute ischemic stroke in rats," Methods Find Exp Clin Pharmacol 29:257-263 (2007).

Briyal, et al. "Endothelin-A receptor antagonists prevent amyloid-beta-induced increase in ETA receptor expression, oxidative stress, and cognitive impairment," Journal of Alzheimer's disease : JAD 23:491-503 (2011).

Briyal, et al. "Repeated administration of exendin-4 reduces focal cerebral ischemia-induced infarction in rats," Brain research 1427:23-34 (2012a).

Briyal, et al. "Endothelin-A receptor antagonist BQ123 potentiates acetaminophen induced hypothermia and reduces infarction following focal cerebral ischemia in rats," European journal of pharmacology 644:73-79 (2010).

Briyal, et al. "Repeated administration of centhaquin to pregnant rats did not affect postnatal development and expression of endothelin receptors in the brain, heart or kidney of pups," Arzneimittel-Forschung 62:670-676 (2012b).

Brondani et al., "Levels of vascular cell adhesion molecule-1 and endothelin-1 in ischemic stroke: A longitudinal prospective study," Clin Biochem 40:282-284 (2007).

Brooks et al., Identification and function of putative ETB receptor subtypes in the dog kidney, J. Cardiovasc. Pharmacol., 26(Suppl 3):S322-5 (1995).

Bulger et al., Out-of-hospital hypertonic resuscitation after traumatic hypovolemic shock: a randomized, placebo controlled trial, Ann. Surg., 253(3):431-41 (2011).

Bulger et al., Out-of-hospital hypertonic resuscitation following severe traumatic brain injury: a randomized controlled trial, JAMA, 304(13):1455-64 (2010).

Bylund et al., International Union of Pharmacology nomenclature of adrenoceptors, Pharmacol. Rev., 46(2):121-36 (1994).

Cai et al., Novel insights for systemic inflammation in sepsis and hemorrhage, Mediators Inflamm. 2010:642462 (2010).

Cali et al., "Enhanced parkin levels favor ER-mitochondria cross-talk and guarantee Ca2+ transfer to sustain cell bioeneraetics," Biochimica et Biophysica Acta 1832:495-508 (2013).

Cardillo et al., Interactions between nitric oxide and endothelin in the regulation of vascular tone of human resistance vessels in vivo, Hypertension, 35(6):1237-1241 (2000).

Carlsson, "Assessment of Chronic Pain. I. Aspects of the Reliability and Validity of the Visual Analoaue Scale," Pain 16:87-101 (1983).

Carmichael, "Cellular and molecular mechanisms of neural repair after stroke: making waves," Annals of neurology 59:735-742 (2006).

Carpy et al., "Structure of 1-(3-Methylphenyl)-4-(2-quinolylethyl)piperazone: Centhaquin," Acta Crvstalloaraohica C47:227-229 (1991).

Carrier et al., "Enhancement of Alpha-1 and Alpha-2 Adrenerigic Agonist-Induced Vasoconstriction by Removal of Endothelium in Rat Aorta," J Pharmacol Exp Ther 232:682-687 (1985).

Casadesus, et al. "Indices of metabolic dysfunction and oxidative stress," Neurochemical research 32:717-722 (2007).

Cavun et al., Evidence that hemorrhagic hypotension is mediated by the ventrolateral periaqueductal gray region, Am. J. Physiol. Regul. Integr. Comp. Physiol., 281(3):R747-52 (2001).

Chakrabarti et al., "Therapeutic potential of endothelin receptor antagonists in diabetes," Expert Opinion on Investigational Drugs 9(12):2873-2888 (2000).

Chan et al., "Effects of endothelin-1 on portal-systemic collaterals of common bile duct-ligated cirrhotic rats," European Journal of Clinical Investigation 34(4):290-296 (2004).

Chappell et al., A rational approach to perioperative fluid management, Anesthesiology, 109(4):723-40 (2008).

Charu et al., "Inhaled corticosteroids and long term outcome in adults with asthma," Thorax 61:1011-1012 (2006).

Chen et al., "Physical Conditioning Decreases Norepinephrine-Induced Vasoconstriction in Rabbits-Possible Roles of Norepinephrine-Evoked Endothelium-Derived Relaxing Factor," Circulation 90:970-975 (1994).

Chen, et al. "Niaspan increases angiogenesis and improves functional recovery after stroke," Annals of neurology 62:49-58 (2007).

Chuquet, et al. "Selective blockade of endothelin-B receptors exacerbates ischemic brain damage in the rat," Stroke; a iournal of cerebral circulation 33:3019-3025 (2002).

Cirrito, et al. "Synaptic activity regulates interstitial fluid amyloid-beta levels in vivo," Neuron 48:913-922 (2005).

Consigny, "Endothelin-1 increases arterial sensitivity to 5-hydroxytryptamine," Eur J Pharmacol 186:239-245 (1990).

Cowburn et al., "Selective or non-selective endothelin receptor antagonists for chronic heart failure: what do we know so far?", Journal of Clinical and Basic Cardiology 2(1):41-44 (1999).

Cowley et al., Renal medullary oxidative stress, pressure-natriuresis, and hypertension, Hypertension, 52(5):777-786 (2008).

Cuervo, "Autophagy: In Sickness and in Health," Trends Cell Biol 14:70-77 (2004).

Cutler, et al. "Involvement of oxidative stress-induced abnormalities in ceramide and cholesterol metabolism in brain aging and Alzheimer's disease," Proceedings of the National Academy of Sciences of the United States of America 101:2070-2075 (2004).

D'Angelo et al., "In vivo evidence for endothelin-1-mediated attenuation of a1-adrenergic stimulation," Am J Physiol Heart Circ Physiol 290:H1251-1258 (2006).

De Boode, Clinical monitoring of systemic hemodynamics in critically ill newborns, Early Hum. Dev., 86(3):137-41 (2010).

De la Torre, "Impaired brain microcirculation may trigger Alzheimer's disease," Neuroscience and biobehavioral reviews 18:397-401 (1994).

De la Torre, et al. "Hippocampal nitric oxide upregulation precedes memory loss and A beta 1-40 accumulation after chronic brain hypoperfusion in rats," Neurological research 25:635-641 (2003).

(56)            References Cited

OTHER PUBLICATIONS

Deb, et al. "Pathophysiologic mechanisms of acute ischemic stroke: An overview with emphasis on therapeutic significance beyond thrombolysis," Pathophysiology 17:197-218 (2010).

Dembowski, et al. "Phenotype, intestinal morphology, and survival of homozygous and heterozygous endothelin B receptor-deficient (spotting lethal) rats," J Pediatr Surg 35:480-488 (2000).

Dillon et al., "A bioassay of Treatment of Hemorrhagic Shock," Archives of Surgery, 93(4):537- 555, plus abstract (1966).

Dimyan, et al. "Neuroplasticity in the context of motor rehabilitation after stroke," Nature reviews Neurology 7:76-85 (2011).

Ding, et al. "Magnetic resonance imaging investigation of axonal remodeling and angiogenesis after embolic stroke in sildenafil-treated rats," Journal of Cerebral Blood Flow and Metabolism, 28:1440-1448 (2008).

Doerks et al., Protein annotation: detective work for function prediction, Trends Genet., 14(6):248-50 (1998).

Donnan, et al. "Stroke," Lancet 371:1612-1623 (2008).

Drabek et al., Intravenous hydrogen sulfide does not induce hypothermia or improve survival from hemorrhagic shock in pigs, Shock, 35(1):67-73 (2011).

Dries et al., "Hyotensive Resuscitation," Shock 6(5):311-316 (1996).

Dubick et al., Issues of concern regarding the use of hypertonic/hyperoncotic fluid resuscitation of hemorrhagic hypotension, Shock, 25(4):321-8 (2006).

Dung et al., Fluid replacement in dengue shock syndrome: a randomized, double-blind comparison of four intravenous-fluid regimens, Clin. Infect. Dis., 29(4):787-94 (1999).

Edwards et al., Endothelin-1 levels in ischaemia, reperfusion, and haemorrhagic shock in the canine infrarenal aortic revascularisation model, European journal of vascular surgery, 8(6):729-734 (1994).

Kohzuki, et al., "Endothelin receptors in ischemic rat brain and Alzheimer brain," Journal of cardiovascular pharmacology 26 Suppl 3:S329-331 (1995).

Kojima, et al. Circulating levels of endothelin and atrial natriuretic factor during postnatal life' Acta Paediatr 81:676-677 (1992).

Komarov et al., A chemical inhibitor of p53 that protects mice from the side effects of cancer therapy, Science, 285:1733-1737 (1999).

Kon et al., Glomerular actions of endothelin in vivo, The Journal of clinical investigation, 83:1762-1767 (1989).

Kopito et al., "Conformational Disease," Nat Cell Biol 2:E207-209 (2000).

Kossmann et al., Interleukin-6 released in human cerebrospinal fluid following traumatic brain injury may trigger nerve growth factor production in astrocytes, Brain research, 713:143-152 (1996).

Kovacs et al., "Alpha2 antagonist yohimbine suppresses maintained firing of rat prefrontal neurons in vivo," Neuroreport 14(6):833-6 (2003).

Kowalczyk et al., The role of endothelin-1 and endothelin receptor antagonists in inflammatory response and sepsis, Archivum immunologiae et therapiae experimentalis, 63:41-52 (2015).

Kowalenko et al., Improved outcome with hypotensive resuscitation of uncontrolled hemorrhagic shock in a swine model, J. Trauma, 33(3):349-53 (1992).

Koyama, et al. "I.c.v administration of an endothelin ET(B) receptor agonist stimulates vascular endothelial growth factor-A production and activates vascular endothelial growth factor receptors in rat brain," Neuroscience 192:689-698 (2011).

Koyama, et al., "Endothelins reciprocally regulate VEGF-A and angiopoietin-1 production in cultured rat astrocvtes: implications on astrocvtic proliferation," Glia 60:1954-1963 (2012).

Kumar et al., Nationwide Trends of Severe Sepsis in the 21st Century (2000-2007) Chest 140(5):1223-31 (2011).

Kuwaki et al., "Modulatory Effects of Rat Endothelin on Central Cardiovascular Control in Rats," Jpn J Physiol 40:97-116 (1990).

Langer et al., "Recent Developments in Noradrenergic Neurotransmission and its Relevance to the Mechanism of Action of Certain Antihypertensive Agents," Hypertension 2:372-382 (1980).

Lavhale et al., Endothelin modulates the cardiovascular effects of clonidine in the rat, Pharmacological research, 62:489-499 (2010).

Lavhale et al., Resuscitative effect of centhaquin after hemorrhagic shock in rats, The Journal of surgical research, 179:115-124 (2013).

Lawrence et al., Evidence for ETA and ETB receptors in rat skin and an investigation of their function in the cutaneous microvasculature, Br. J. Pharmacol., 115:840-844 (1995).

Laziz I, et al. "Endothelin as a neuroprotective factor in the olfactory epithelium," Neuroscience 172:20-29 (2011).

Lee, et al., "The endothelin receptor-Bis required for the migration of neural crest-derived melanocyte and enteric neuron precursors," Dev Biol 259:162-175 (2003).

Leonard et al., Endothelin B receptor agonist, IRL-1620, enhances angiogenesis and neurogenesis following cerebral ischemia in rats, Brain research, 1528:28-41 (2013).

Leonard, et al., "Endothelin B receptor agonist, IRL-1620, reduces neurological damage following permanent middle cerebral artery occlusion in rats," Brain research 1420:48-58 (2011).

Leonard, et al., "Repeated administration of ET(B) receptor agonist, IRL-1620, produces tachyphylaxis only to its hypotensive effect," Pharmacological research: the official journal of the Italian Pharmacological Society 60:402-410 (2009).

Leonard, et al., "Endothelin B receptor agonist, IRL-1620, provides long-term neuroprotection in cerebral ischemia in rats," Brain research 1464:14-23 (2012).

Levin, "Endothelins," The New England journal of medicine 333:356-363 (1995).

Li et al., Ideal permissive hypotension to resuscitate uncontrolled hemorrhagic shock and the tolerance time in rats, Anesthesiology, 114(1):111-9 (2011).

Li, et al., "The requirement of extracellular signal-related protein kinase pathway in the activation of hypoxia inducible factor 1 alpha in the developing rat brain after hypoxia-ischemia," Acta neuropathologica 115:297-303 (2008).

Liangos et al., Epidemiology and outcomes of acute renal failure in hospitalized patients: a national survey, Clin. J. Am. Soc. Nephrol., 1:43-51 (2006).

Lima et al., The prognostic value of the subjective assessment of peripheral perfusion in critically ill patients, Grit. Care Med., 37(3):934-8 (2009).

Liu et al., Hemorrhage-induced vascular hyporeactivity to norepinephrine in select vasculatures of rats and the roles of nitric oxide and endothelin, Shock, 19(3):208-14 (2003).

Liu, et al., "Contralesional axonal remodeling of the corticospinal system in adult rats after stroke and bone marrow stromal cell treatment," Stroke; a journal of cerebral circulation 39:2571-2577 (2008).

Loo, et al. "Cortical expression of endothelin receptor subtypes A and B following middle cerebral artery occlusion in rats," Neuroscience 112:993-1000 (2002).

Lopes, et al., "Neurodegeneration in an Abeta-induced model of Alzheimer's disease: the role of Cdk5," Aging ce/19:64-77 (2010).

Lowry, et al., "Protein measurement with the Falin phenol reagent," The Journal of biological chemistry 193:265-275 (1951).

Ly, et al. "Neuroprotection and thrombolysis: combination therapy in acute ischaemic stroke," Expert Opin Pharmacother 7:1571-1581 (2006).

Makaritsis et al., Role of alpha(2)-adrenergic receptor subtypes in the acute hypertensive response to hypertonic saline infusion in anephric mice, Hypertension, 35(2):609-13 (2000).

Makaritsis et al., Role of the alpha2B-adrenergic receptor in the development of salt-induced hypertension, Hypertension, 33(1):14-7 (1999).

Malik, et al., "Neurogenesis continues in the third trimester of pregnancy and is suppressed by premature birth," The Journal of neuroscience: the official journal of the Society for Neuroscience 33:411-423 (2013).

Malone et al., Massive transfusion practices around the globe and a suggestion for a common massive transfusion protocol, J. Trauma, 60(6 Suool):S91-6 (2006).

Mark, et al., "A role for 4-hydroxynonenal, an aldehydic product of lipid peroxidation, in disruption of ion homeostasis and neuronal death induced by amyloid beta-peptide," Journal of neurochemistry 68:255-264 (1997).

(56)         References Cited

OTHER PUBLICATIONS

Martini et al., "Acidosis and Coagulopathy—The Differential Effects on Fibrinogen Synthesis and Breakdown in Pigs," Annals of Surgery 246(5):831-835 (2007).

Mathers, et al., "Global and regional causes of death," Br Med Bu/192:7-32 (2009).

Matus et al., "Protein Folding Stress In Neurodegenerative Diseases: A Glimpse Into The ER," Curr Opin Cell Biol 23:239-252 (2011).

Mazzoni et al., Suc-[Glu9,Ala11,15]-endothelin-1 (8-21), IRL 1620, identifies two populations of ET(B) receptors in guinea-pig bronchus, Br. J. Pharmacol., 127:1406-1414 (1999).

Meier-Ruge, et al. "Changes in brain glucose metabolism as a key to the pathogenesis of Alzheimer's disease," Gerontology 40:246-252 (1994).

Meller et al., "The Possible Role of Flia in Nociceptive Processing and Hyperalgesia in the Spinal Cord of the Rat," Neurooharmacol. 33:1471-8 (1994).

Meng et al., Distinct effects of systemic infusion of G-CSF vs. IL-6 on lung and liver inflammation and injury in hemorrhagic shock, Shock, 14:41-48 (2000).

Merck Manual 17th edition Japanese version (English translation), pp. 1709-1706 (1999).

Merkwirth et al., "Loss of Prohibitin Membrane Scaffolds Impairs Mitochondrial Architecture and Leads to Tau Hyperphosphorylation and Neurodegeneration," PLOS Genetics 8(11):e1003021, 13 pages (2012).

Micieli, et al., "Safety and efficacy of alteplase in the treatment of acute ischemic stroke," Vase Health Risk Manag 5:397-409 (2009).

Mickley et al., Activation of endothelin ETA receptors masks the constrictor role of endothelin ETB receptors in rat isolated small mesenteric arteries, British journal of pharmacology, 120:1376-1382 (1997).

Rao et al., "Misfolded proteins, endoplasmic reticulum stress and neurodegeneration," Curr Opin Cell Biol. 16(6):653-662 (2004).

Reagan-Shaw et al., Dose translation from animal to human studies revisited, FASEB J., 22(3):659-61 (Mar. 2008).

Rebello et al., "Systemic hemodynamic and regional circulatory effects of centrally administered endothelin-1 are mediated through ETA receptors," Brain Research 676:141-150 (1995).

Rebello, et al. "Elevated levels of endothelin-1 following unilateral cerebral-ischemia in rats," Faseb Journal 9:A937-A (1995).

Recht et al., The sequencing of chemotherapy and radiation therapy after conservative surgery for early-stage breast cancer, NEJM, 334(21):1356-61 (1996).

Rhee et al., A study of the safety and efficacy of travoprost 0.004%/timolol 0.5% ophthalmic solution compared to latanoprost 0.005% and timolol 0.5% dosed concomitantly in patients with open-angle glaucoma or ocular hypertension, Clin. Ophthalmol., 2(2):313-9 (2008).

Rhee et al., Searching for the optimal resuscitation method: recommendations for the initial fluid resuscitation of combat casualties, J. Trauma, 54(5Suool):S52-62 (2003).

Riechers, et al. "Endothelin B receptor deficient transgenic rescue rats: a rescue phenomenon in the brain," Neuroscience 124:719-723 (2004).

Roger, et al. "Heart disease and stroke statistics—2012 update: a report from the American Heart Association," Circulation 125:e2-e220 (2012).

Rosenstein, et al., "VEGF in the nervous system," Organogenesis 6:107-114 (2010).

Rossaint et al., Key issues in advanced bleeding care in trauma, Shock, 26:322-331 (2006).

Rubinsztein, "The roles of intracellular protein-degradation pathways in neurodegeneration," Nature 443:780-786 (2006).

Ruetten et al., "Effects of the endothelin receptor antagonist, SB 209670, on circulatory failure and organ injury in endotoxic shock in the anaesthetized rat," British Journal of Pharmacology, 118(1):198-204 (1996).

Sakai et al., Hemoglobin vesicles and red blood cells as carriers of carbon monoxide prior to oxyaen for resuscitation after hemorrhaaic shock in a rat model, Shock, 31(5):507-14 (2009).

Sakamoto et al., "Distinct Subdomains of Human Endothelin Receptors Determine Their Selectivity to EndothelinA-selective Antagonist and EndothelinB-selective Agonists," J Biol Chem 268:8547-8553 (1993).

San Martin et al., The epidemiology of dengue in the americas over the last three decades: a worrisome reality, Am. J. Trop Med. Hyg., 82(1):128-35 (2010).

Sandoo et al., The endothelium and its role in regulating vascular tone, The open cardiovascular medicine journal, 4:302-312 (2010).

Santry et al., Fluid resuscitation: past, present, and the future, Shock, 33(3):229-41 (2010).

Sardanelli et al., Dynamic helical CT of breast tumors, J. Comp. Assisted Tomography, 22(3):398-407 (1998).

Schadt et al., "Hemodynamic and neurohumoral responses to acute hypovolemia in conscious mammals," Am J Physiol 260(2 Pt 2):H305-18 (1991).

Schiffrin, et al. "Clinical significance of endothelin in cardiovascular disease," Curr Opin Cardiol 12:354-367 (1997).

Schinelli, "Pharmacology and physiopathology of the brain endothelin system: an overview," Curr Med Chem 13:627-638, (2006).

Schmitt et al., "Localization of the Hypotensive Effect of 2-(2-6-Dichlorophenylamino)-2-Imidazoline Hydrochloride (St 155, Catapresan)," Eur J Pharmacol 6:8-12 (1969).

Schneider et al., Contrasting actions of endothelin ET(A) and ET(B) receptors in cardiovascular disease, Annual review of pharmacology and toxicology, 47:731-759 (2007).

Search Report from European Application No. 14823205.1 dated Jan. 4, 2017.

Selkoe, "Folding Proteins In Fatal Ways," Nature 426:900-904 (2003).

Shackford et al., The epidemiology of traumatic death. A population-based analysis, Archives of surgery, 128:571-575 (1993).

Sharma et al., "Yohimbine modulates diaspirin crosslinked hemoglobin-induced systemic hemodynamics and regional circulatory effects," Critical Care Medicine 23(5):874-84 (1995).

Shetty et al. Biochem Biophys Res Commun 191:459-464 (1993).

Shin, et al., "Age-dependent cerebrovascular dysfunction in a transgenic mouse model of cerebral amyloid angiopathy," Brain : a journal of neurology 130:2310-2319 (2007).

Sims, et al., "Mitochondria, oxidative metabolism and cell death in stroke," Biochimica et biophysica acta pp. 80-91 (2009).

Singhi et al., Dengue and dengue hemorrhagic fever: management issues in an intensive care unit, J. Pediatr. (Rio J.). 83(2Suppl):S22-35 (2007).

Skolnick et al., From genes to protein structure and function: novel applications of computational approaches in the genomic era, Trends Biotechnol., 18(1):34-9 (2000).

Smith, et al. "Soluble beta-amyloid (A beta) 40 causes attenuation or potentiation of noradrenaline-induced vasoconstriction in rats depending upon the concentration employed," Neuroscience letters 367:129-132 (2004).

Smyth et al., Use of vasoactive agents to increase tumor perfusion and the antitumor efficacy of drug-monoclonal antibody conjugates, J. Natl. Cancer Inst., 79(6):1367-73 (1987).

Sonveaux et al., Endothelin-1 is a critical mediator of myogenic tone in tumor arterioles: implications for cancer treatment, Cancer Res., 64(9):3209-14 (2004).

Souza et al., "Increased Cardiac Sympathetic Drive and Reduced Vagal Modulation Following Endothelin Receptor Antagonism in Healthy Conscious Rats," Clin Exp Pharmacol Physiol 35:751-756 (2008).

Srimal et al., "Pharmacological studies on 2-(2-(4-(3-methylphenyl)-1-Piperazinyl)Ethyl) Quinoline (Centhaquin). I. Hypotensive Activity," Journal of the Italian Pharmac Pharmacol Res 22:319-329 (1990).

Srimal et al., "Studies on 2-(2-(4-(3-Methylphenyl)1-Piperazinyl)Ethyl Quinoline (Centhaquin), a Centrally Acting Antihypertensive II.Effect on Cardiohaemodynamics," Asia Pacific Journal of Pharmacology 5:185-190 (1990).

(56)          References Cited

OTHER PUBLICATIONS

Sriram et al., Divergent roles for tumor necrosis factor-alpha in the brain, Journal of neuroimmune pharmacology, 2:140-153 (2007).
Stein et al., "The Discovery of Sulfonamide Endothelin Antagonists and the Development of the Orally Active ETA Antagonist 5-(Dimethylamino)-N-(3,4-dimethyl-5-isoxazolyl)-1-naphthalenesulfonamide," J Med Chem 37:329-331 (1994).
Steinwachs, et al., "The future of cardiology: utilization and costs of care," J Am Coll Cardiol 35:91B-98B (2000).
Strong, et al. "Preventing stroke: saving lives around the world," Lancet Neural 6:182-187 (2007).
Suo, et al. "Soluble Alzheimers beta-amyloid constricts the cerebral vasculature in vivo," Neuroscience letters 257:77-80 (1998).
Supavekin et al., Differential gene expression following early renal ischemia/reperfusion, Kidney Int., 63:1714-1724 (2003).
Supplementary European Search Report in counterpart foreign Application No. EP10770318, dated Oct. 23, 2012.
Tabuchi et al., "Endothelin Enhances Adrenergic Vasoconstriction in Perfused Rat Mesenteric Arteries," 159(3):1304-1308 (1989).
Tabuchi et al., "Endothelin Inhibits Presynaptic Adrenergic Neurotransmission in Rat Mesenteric Artery," Biochem Biophys Res Commun 161:803-808 (1989).
Takagawa et al., Efficacy of the drugs administered to the patients with cerebral vascular diseases from a viewpoint of cerebral blood flow measurement, 48(9):667-93 (1994).
Tavares et al., Localization of alpha 2A- and alpha 2B-adrenergic receptor subtypes in brain, Hypertension, 27(3 Pt 1):449-55 (1996).
Hardy et al., Massive transfusion and coagulopathy: pathophysiology and implications for clinical management, Can. J. Anaesth., 53(6 Suppl):S40-58 (2006).
Hardy, et al. "The amyloid hypothesis of Alzheimer's disease: progress and problems on the road to therapeutics," Science 297:353-356 (2002).
Harris et al., Haemodynamic and renal tubular effects of low doses of endothelin in anaesthetized rats, The Journal of physiology, 433:25-39 (1991).
Harvey et al., Imaging of tumour therapy responses by dynamic CT, Eur. J. Radiology, 30:221-6 (1999).
Hawkins, et al. "The blood-brain barrier/neurovascular unit in health and disease," Pharmacological reviews 57:173-185 (2005).
Hegde et al., "Attenuation in Rat Brain Nitric Oxide Synthase Activity in the Coarctation Model of Hypertension," Pharmacol Res 36:109-114 (1997).
Hein et al., Two functionally distinct alpha2-adrenergic receptors regulate sympathetic neurotransmission, Nature, 402(6758):181-4 (1999).
Helmy et al., Altered peripheral vascular responses to exogenous and endogenous endothelin-1 in patients with well-compensated cirrhosis, Hepatology, 33:826-831 (2001).
Henrion et al., Potentiation of norepinephrine-induced contractions by endothelin-1 in the rabbit aorta, Hypertension, 22(1):78-83 (1993).
Hensley, et al., "A model for beta-amyloid aggregation and neurotoxicity based on free radical generation by the peptide: relevance to Alzheimer disease," Proceedings of the National Academy of Sciences of the United States of America 91:3270-3274 (1994).
Hermann, et al., "Implications of vascular endothelial growth factor for postischemic neurovascular remodeling," Journal of cerebral blood flow and metabolism : official journal of the International Society of Cerebral Blood Flow and Metabolism 29:1620-1643 (2009).
Heslop et al., "Haemorrhage-Evoked Compensation and Decompensation are Mediated by Distinct Caudal Midline Medullary Regions in the Urethane-Anaesthetised Rat," Neuroscience 113(3):555-67 (2002).
Hickey et al., "Characterization of a coronary vasoconstrictor produced by cultured endothelial cells," Am J Physiol 248:C550-556 (1985).
Hierholzer et al., Essential role of induced nitric oxide in the initiation of the inflammatory response after hemorrhagic shock, J. Exp. Med., 187(6):917-28 (1998).

Hirschberg et al., Multicenter clinical trial of recombinant human insulin-like growth factor I in patients with acute renal failure, Kidney Int., 55:2423-2432 (1999).
Ho et al., "Excessive Use of Normal Saline in Managing Traumatized Patients in Shock: A Preventable Contributor to Acidosis," J Trauma 51(1):173-7 (2001).
Hoehn, et al. "VEGF mRNA expressed in microvessels of neonatal and adult rat cerebral cortex," Brain Res Mol Brain Res 101:103-108 (2002).
Hoffman et al., Mechanisms of big endothelin-1-induced diuresis and natriuresis : role of ET(B) receptors, Hypertension, 35:732-739 (2000).
Hsia et al., A hemoglobin-based multifunctional therapeutic: polynitroxylated pegylated hemoglobin, Artif. Organs, 36(2):215-20 (2012).
Hunyor et al., "Clonidine overdose," Br Med J 4:23 (1975).
Iadecola, et al. "Threats to the mind: aging, amyloid, and hypertension," Stroke; a journal of cerebral circulation 40:S40-44 (2009).
Ikeda et al., "A New Endothelin Receptor Antagonist, TAK-044, Shows Long-Lasting Inhibition of Both ETA- and ETs-Mediated Blood Pressure Responses in Rats," J Pharmacol Exp Ther 270:728-733 (1994).
Inoue et al., The human endothelin family: three structurally and pharmacologically distinct isopeptides predicted by three separate genes, Proc. Natl. Acad. Sci. USA, 86:2863-2867 (1989).
International Application No. PCT/US12/60257, International Search Report and Written Opinion, mailed Mar. 18, 2013.
International Application No. PCT/US19/30652, International Preliminary Report on Patentability, mailed Nov. 12, 2020.
International Application No. PCT/US19/30652, International Search Report and Written Opinion, mailed Jul. 25, 2019.
International preliminary report on patentability from PCT/US2014/045748 dated Jan. 12, 2016.
International search report from PCT/US2014/045748 dated Nov. 13, 2014.
International Search Report in international application No. PCT/US2008/073581, dated Jul. 15, 2009.
International Search Report in international application No. PCT/US2010/032942, dated Jan. 24, 2011.
International Search Report in international application No. PCT/US2010/033083, dated Jan. 25, 2011.
Ishikawa et al., "Biochemical and pharmacological profile of a potent and selective endothelin B-receptor antaaonist, BQ-788," Proc Natl Acad Sci USA 91(11):4892-4896 (1994).
Ishizuka et al., Endothelin-1 enhances vascular cell adhesion molecule-1 expression in tumor necrosis factor alpha-stimulated vascular endothelial cells, Eur. J. Pharmacol., 369(2):237-45 (1999).
Jacob et al., The challenge in management of hemorrhagic shock in trauma, Medical journal, Armed Forces India, 70(2):163-169 (2014).
Jansen et al., "Blood lactate monitoring in critically ill patients: A systematic health technology assessment," Crit Care Med 37(10):2827-2839 (2009).
Janson, et al., "Increased risk of type 2 diabetes in Alzheimer disease," Diabetes 53:474-481 (2004).
Jarajapu et al. "The a1A-adrenoceptor subtype mediates contraction in rat femoral resistance arteries," Eur J Pharmacol 422:127-135 (2001).
Jochem et al., Cardiac and regional haemodynamic effects of endothelin-1 in rats subjected to critical haemorrhagic hypotension, Journal of physiology and pharmacology, 54:383-396 (2003).
Johnson, et al., "Cognitive profiles in dementia: Alzheimer disease vs healthy brain aging," Neurology 71:1783-1789 (2008).
Kakkar, et al., "A modified spectrophotometric assay of superoxide dismutase," Indian journal of biochemistry & biophysics 21:130-132 (1984).
Katayama, Current trends in the treatment of acute ischemic stroke, Nichiidaishi, 65(3):4-9 (1999).
Kaundal, et al., "Targeting endothelin receptors for pharmacotherapy of ischemic stroke: current scenario and future perspectives," Drug Discov Today 17:793-804 (2012).
Kauvar et al., Impact of hemorrhage on trauma outcome: an overview of epidemiology, clinical presentations, and therapeutic considerations, J. Trauma, 60(6 Suppl):S3-11 (2006).

(56) References Cited

OTHER PUBLICATIONS

Kennedy et al., "Centrally Acting Imidazolines Stimulate Vascular Alpha 1A-Adrenergic Receptors in Rat-Tail Artery," Cell Mol Neurobiol 26:645-657 (2006).

Khongphatthanayothin et al., "Myocardial depression in dengue hemorrhagic fever: Prevalence and clinical description," Pediat Crit Care Med 8(6):524-9 (2007).

Kim et al., Innate inflammatory responses in stroke: mechanisms and potential therapeutic targets, Current medicinal chemistry, 21:2076-2097 (2014).

Kitazono, et al., "Enhanced responses of the basilar artery to activation of endothelin-B receptors in stroke-prone spontaneously hypertensive rats," Hypertension 25:490-494 (1995).

Kobinger et al. "Kreislaufuntersuchungen mit 2-(2,6-Dichlorphenylamino)-2-imidazolin-hydrochlorid," Arzneimit-telforschung 17:292-300 (1967).

Kobinger, "Central a-Adrenergic Systems as Targets for Hypotensive Drugs," Rev Physiol Biochem Pharmacol 81:39-100 (1978).

Kohan et al., Regulation of blood pressure and salt homeostasis by endothelin, Physiological reviews, 91:1-77 (2011).

Abo-Zena et al., "Hypertensive Urgency Induced by an Interaction of Mirtazapine and Clinidine," Pharmacotherapy 20:476-478 (2000).

Acosta et al., Lethal injuries and time to death in a level I trauma center, J. Am. Coll. Surg., 186(5):528-33 (1998).

Ahmed, et al. "Curcuminoids Enhance Memory in an Amyloid-Infused Rat Model of Alzheimer's Disease," Neuroscience 169:1296-1306 (2010).

Alam et al., "Effect of different resuscitation strategies on neutrophil activation in a swine model of hemorrhaaic shock," Resuscitation 60:91-99 (2004).

Alam et al., New developments in fluid resuscitation, Surg. Clin. North Am., 87(1):55-72, vi (2007).

Allgren et al., Anaritide in acute tubular necrosis. Auriculin Anaritide Acute Renal Failure Study Group, N. Engl. J. Med., 336(12):828-834 (1997).

Alten et al., Prevention of hypovolemic circulatory collapse by IL-6 activated Stat3, PloS one, 3(2):e1605 (2008).

Altman et al., Abnormal regulation of the sympathetic nervous system in alpha2A-adrenergic receptor knockout mice, Mol. Pharmacol., 56(1):154-61 (1999).

Amaresh et al., Centhaquine Restores Renal Blood Flow and Protects Tissue Damage After Hemorrhagic Shock and Renal Ischemia, Frontiers In Pharmacology, 12: (2021).

Andres et al. "Human neural stem cells enhance structural plasticity and axonal transport in the ischaemic brain," Brain 134:1777-1789 (2011).

Andurkar et al., Assessment of the analgesic effect of centhaquin in mouse tail flick and hot-plate tests, Pharmacology, 88(5-6):233-41 (2011).

Angus et al., Epidemiology of severe sepsis in the United States: analysis of incidence, outcome, and associated costs of care, Grit. Care. Med., 29(7):1303-10 (2001).

Area-Gomez et al., "Mitochondria-associated ER membranes and Alzheimer Disease," Curr Opin Genet Dev. 38:90-96 (2016).

Arya, "Centhaquin," Drugs of the Future 9(2):104-105 (1984).

Asano, et al. "Endothelin: a potential modulator of cerebral vasospasm," European journal of pharmacology 190:365-372 (1990).

Ayuste et al., "Hepatic and Pulmonary Apoptosis After Hemorrhagic Shock in Swine Can Be Reduced Throuah Modifications of Conventional Rinaer's Solution," J Trauma 60(1):52-63 (2006).

Bacigaluppi et al., "Delayed post-ischaemic neuroprotection following systemic neural stem cell transplantation involves multiple mechanisms," Brain: a journal of neurology 132:2239-2251 (2009).

Backo et al., "Clonidine-Induced Hypertension in a Patient with a Spinal Lesion," Ann Pharmacother 36:1396-1398 (2002).

Bajpai et al., Fourier transform infrared spectra and normal mode analysis of 1-(3-methyl phenyl piperazin-I-yl)-2-(quinolin-2-yl)ethane (Centhaquin): a potent centrally acting anti-hypertensive agent, Journal of Molecular Structure, 516:15-21 (2000).

Balogh et al., Both primary and secondary abdominal compartment syndrome can be predicted early and are harbingers of multiple organ failure, The Journal of trauma, 54(5):848-859 (2003).

Baquer, et al. "A metabolic and functional overview of brain aging linked to neurological disorders," Biogerontology 10:377-413 (2009).

Barcroft et al., On the vasodilatation in human skeletal muscle during post-haemorrhagic fainting, J. Physiol., 104(2):161-75 (1945).

Barone, et al. "Selective antagonism of endothelin-A-receptors improves outcome in both head trauma and focal stroke in rat," Journal of cardiovascular pharmacology 36:S357-361 (2000).

Barone, et al. "The endothelin receptor antagonist SB 217242 reduces cerebral focal ischemic brain injury," Journal of cardiovascular pharmacology 26 Suppl 3:S404-407 (1995).

Bastin et al., Salt selection and optimisation procedures for pharmaceutical new chemical entitites, Org. Process Res. & Dev., 4:427-36 (2000).

Bath, et al. "ABC of arterial and venous disease, Acute stroke," BMJ 320:920-923 (2000).

Bauer et al., Functional significance of endothelin B receptors in mediating sinusoidal and extrasinusoidal effects of endothelins in the intact rat liver, Hepatology, 31(4):937-947 (2000).

Bell et al., Effect of endothelin-1 and sarafotoxin S6c on blood flow in a rat tumor, J. Cardiovasc. Pharmacol., 26(Suppl. 3):S222-5 (1995).

Bell et al., Modification of blood flow in the HSN tumour and normal tissues of the rat by the endothelin ETb receptor agonist, IRL 1620, Int. J. Cancer, 80:295-302 (1999).

Bell, et al. "Neurovascular mechanisms and blood-brain barrier disorder in Alzheimer's disease," Acta neuropathologica 118:103-113 (2009).

Bellamy, The causes of death in conventional land warfare: implications for combat casualty care research, Mil. Med., 149(2):55-62 (1984).

Bennett, "The LANSS Pain Scale: the Leeds assessment of neuropathic symptoms and signs," Pain. 92:147-157 (2001).

Berge et al., Pharmaceutical salts, J. Pharm. Sci., 66(1):1-19 (Jan. 1977).

Bertolini et al., "The Adrenocorticotropic Hormone (ACTH)-Induced Reversal of Hemorrhagic Shock," Resuscitation 18(2-3):253-267 (1989).

Bhatnagar et al., Effect of centhaquine on spontaneous and evoked norepinephrine release from isolated perfused rabbit heart, Arzneimit-telforschung, 35(4):693-697 (1985).

Bickell et al., "The detrimental effects of intravenous crystalloid after aortotomy in swine," Surgery 110(3):529-36 (1991).

Bickell et al., "Use of Hypertonic Saline/Dextran Versus Lactated Ringer's Solution as a Resuscitation Fluid After Uncontrolled Aortic Hemorrhage in Anesthetized Swine," Ann Emerg Med 21(9):1077-85 (1992).

Bickell et al., Immediate versus delayed fluid resuscitation for hypotensive patients with penetrating torso iniuris, N. Engl. J. Med., 331(17):1105-9 (1994).

Bomber et al., Propranolol hydrochloride enhancement of tumor perfusion and uptake of gallium-67 in a mouse sarcoma, J. Nucl. Med., 27(2):243-5 (1986).

Bonanno, Physiopathology of shock, Journal of emergencies, trauma, and shock, 4(2):222-232 (2011).

Bonvallet et al., "BQ123, an ETA-receptor antagonist, attenuates hypoxic pulmonary hyertension in rats," Am J Physiol 266:H1327-1331 (1994).

Bork, "Powers and Pitfalls in Sequence Analysis: The 70% Hurdle," Genome Res. 10(4):398-400 (2000).

Bourque et al., The interaction between endothelin-1 and nitric oxide in the vasculature: new perspectives, American journal of physiology Regulatory, integrative and comparative physiology, 300(6):R1288-1295 (2011).

Bousquet et al., "Pharmacological Tools for the Study of the Central Vasomotor Control," Biochem Pharmacol 32:1459-1465 (1983).

Brasch et al., Assessing tumor angiogenesis using macromolecular MR imaging contrast media, JMRI, 7:68-74 (1997).

Bredesen, et al. "Cell death in the nervous system," Nature 443:796-802 (2006).

(56) References Cited

OTHER PUBLICATIONS

Breier, et al. "The role of vascular endothelial growth factor in blood vessel formation," Trends in cell biology 6:454-456 (1996).

Brenner, "Errors in genome annotation," Trends in Genetics, 15(4):132-3 (1999).

Breuiller-Fouche et al., Regulation of the endothelin/endothelin receptor system by interleukin-1 {beta} in human myometrial cells, Endocrinology, 146(11):4878-4886 (2005).

Brierley et al., Clinical practice parameters for hemodynamic support of pediatric and neonatal septic shock: 2007 update from the American College of Critical Care Medicine, Crit. Care Med., 37(2):666-88 (2009).

Ehrenreich et al., Endothelin b receptor deficiency is associated with an increased rate of neuronal apoptosis in the dentate gyrus, Neuroscience, 95(4):993-1001 (2000).

Ehrenreich, "The astrocytic endothelin system: toward solving a mystery focus on distinct pharmacological properties of ET-1 and ET-3 on astroglial gap junctions and Ca(2+) signaling" The American journal of physiology 277:C614-615 (1999).

Ehrenreich, et al. "Endothelin B receptor-deficient rats as a subtraction model to study the cerebral endothelin system," Neuroscience 91:1067-1075 (1999).

Ellman, "Tissue sulfhydryl groups," Archives of biochemistry and biophysics 82:70-77 (1959).

Engstrom et al., "Acidosis Impairs the Coagulation: A Thromboelastograhic Study," J Trauma 61(3):624-8 (2006).

Ethell, "An amyloid-notch hypothesis for Alzheimer's disease," The Neuroscientist 16:614-617 (2010).

European Application No. 19796519.7, European Search Report and Opinion, mailed Dec. 20, 2021.

Fagura et al., "Pharmacological classification of a1-adrenoceptors mediating contractions of rabbit isolated ear artery: comparison with rat isolated thoracic aorta," Br J Pharmacol 120:247-258 (1997).

Feigin, et al. "Worldwide stroke incidence and early case fatality reported in 56 population-based studies: a systematic review," Lancet Neural 8:355-369 (2009).

Fellner et al., Endothelin-A and -B receptors, superoxide, and Ca2+ signaling in afferent arterioles, Am. J. Physiol. Renal. Physiol., 292(1):F175-184 (2007).

First Office Action and Search (English translation), Chinese patent application No. 201280076674.9, dated Jun. 20, 2016.

Fisher, et al., The International Agenda for Stroke, in 1st Global Conference on Healthy Lifestyles and Noncommunicable Diseases Control (Association AH ed), American Heart Association, Moscow (2011).

Font, et al., "Angiogenesis, neurogenesis and neuroplasticity in ischemic stroke," Current cardiology reviews 6:238-244 (2010).

Fuhrman et al., Acute kidney injury epidemiology, risk factors, and outcomes in critically ill patients 16-25 years of age treated in an adult intensive care unit, Ann. Intensive Care, 8(1):26 (2018).

Ganster et al., Effects of hydrogen sulfide on hemodynamics, inflammatory response and oxidative stress during resuscitated hemorrhagic shock in rats, Grit. Care, 14(5):R165 (2010).

Gardiner et al., Effects of bosentan (Ro 47-0203), an ETA-, ETB-receptor antagonist, on regional haemodynamic responses to endothelins in conscious rats, British journal of pharmacology, 112(3):823-830 (1994).

Gavras et al., "The .SUB.a2.-adrenergic receptors in hypertension and heart failure: experimental and clinical studies," Journal of Hypertension 19(12):2115-24 (2001).

Gil-Mohapel, et al., "Hippocampal cell loss and neurogenesis after fetal alcohol exposure: insights from different rodent models," Brain Res Rev 64:283-303 (2010).

Gill et al., "Effects of agmatine on the survival rate in rats bled to hemorrhage," Arzneimittelforschung 61(4):229-33 (2011).

Goligorsky, et al. "Co-operation between endothelin and nitric oxide in promoting endothelial cell migration and angiogenesis," Clinical and experimental pharmacology & physiology 26:269-271 (1999).

Gondre et al., Endothelin-1-induced alterations in phenylephrine-induced contractile responses are largely additive in physiologically diverse rabbit vasculature, J. Pharmacol. Exp. Ther., 286(2):635-42 (1998).

Gonzales et al., "Hepatoprotection and Lethality Rescue by Histone Daecetylase Inhibitor Valproic Acid in Fatal Hemorrhagic Shock," J Trauma 65:554-565 (2008).

Gora-Kupilas, et al., "The neuroprotective function of vascular endothelial growth factor (VEGF)," Folia neuropathologica / Association of Polish Neuropathologists and Medical Research Centre, Polish Academy of Sciences 43:31-39 (2005).

Goto et al., Endothelin activates the dihydropyridine-sensitive, voltage-dependent Ca2+ channel in vascular smooth muscle, Proc. Natl. Acad. Sci. USA, 86(10):3915-8 (1989).

Graf et al., Determination of optimal time window for liver scanning with CT during arterial portography, Radiology, 190:43-7 (1994).

Gubler, The changing epidemiology of yellow fever and dengue, 1900 to 2003: full circle?, Comp. Immunol. Microbiol. Infect. Dis., 27(5):319-30 (2004).

Gulati et al., "Central Serotonergic Uptake Mechanisms in Hypertensive Rats: Effects of Clonidine and Centhaquin," European Journal of Pharmacology 231(2):151-156 (1993).

Gulati et al., "Effect of Repeated Administration of Centhaquin, a Centrally Acting Hypotensive Drug, on Adrenergic, Cholinergic (Muscarinic), Dopaminergic, and Serotonergic Receptors in Brain Regions of Rat," Drug Development Research 23:307-323 (1991).

Gulati et al., "Effect of Repeated Administration of Clonidine on Adrenergic, Cholinergic (Muscarinic), Dopaminergic, and Serotonergic Receptors in Brain Regions of Rats," Drug Development Research 22:141-152 (1991).

Gulati et al., "Role of adrenergic mechanisms in the pressor effect of diaspirin cross-linked hemoalobin," J Lab Clin Med 124(1):125-33 (1994).

Gulati et al., Centhaquin improves resuscitative effect of hypertonic saline in hemorrhaged rats, The Journal of surgical research, 178:415-423 (2012).

Gulati et al., Dose-dependent effect of diaspirin cross-linked hemoglobin on regional blood circulation of severely hemorrhaged rats, Shock, 9:65-73 (1998).

Gulati et al., Effect of centhaquin on endothelin receptors following resuscitation of hemorrhaged rat, Critical Care Medicine, 44(12):163 (2016).

Gulati et al., Endothelin antagonizes the hypotension and potentiates the hypertension induced by clonidine, European journal of pharmacology, 230:293-300 (1993).

Gulati et al., Endothelin Receptor Alteration Following Hemorrhagic Shock and Resuscitation by Centhaquin, Circulation, 136:A20622 (2017).

Gulati et al., Role of endothelin-converting enzyme in the systemic hemodynamics and regional circulatory effects of proendothelin-1 (1-38) and diaspirin cross-linked hemoglobin in rats, J. Lab. Clin. Med., 126:559-570 (1995).

Gulati et al., Role of ET and NO in resuscitative effect of diaspirin cross-linked hemoglobin after hemorrhage in rat, The American journal of physiology, 273:H827-836 (1997).

Gulati et al., Role of sympathetic nervous system in cardiovascular effects of centrally administered endothelin-1 in rats, The American journal of physiology, 273:H1177-1186 (1997).

Gulati, et al. "Cardiovascular effects of centrally administered endothelin-1 and its relationship to changes in cerebral blood flow," Life sciences 58:437-445 (1996).

Gulati, et al. "Effect of centrally administered endothelin agonists on systemic and regional blood circulation in the rat: role of sympathetic nervous system," Neuropeptides 31:301-309 (1997).

Gulati, et al., "Cardiovascular effects of centrally administered endothelin-1 in rats," Journal of cardiovascular pharmacology 26 Suppl 3:S244-246 (1995).

Gulati, Evidence for antagonistic activity of endothelin for clonidine induced hypotension and bradycardia, Life Sci., 50(2):153-160 (1992).

Gupta, et al. "Effect of endothelin antagonist (TAK-044) on cerebral ischemic volume, oxidative stress markers and neurobehavioral

(56) References Cited

OTHER PUBLICATIONS parameters in the middle cerebral artery occlusion model of stroke in rats," Life sciences 77:15-27 (2005).

Gutierrez et al., Clinical review: hemorrhagic shock, Critical care, 8:373-381 (2004).

Guyenet et al. "Inhibition of Sympathetic Preganglionic Neurons by Catecholamines and Clonidine: Mediation by an alpha-Adrenergic Receptor," J Neurosci 1:908-917 (1981).

Guzman et al., Dengue: a continuing global threat, Nat. Rev. Microbiol., 8(12 suppl):S7-16 (2010).

Guzman et al., Dengue: an update, Lancet Infect. Dis., 2(1):33-42 (2002).

Guzman et al., Update on the global spread of dengue, Int. J. Antimicrob. Agents, 36 Suppl 1:S40-2 (2010).

Han, et al., "Cerebrovascular dysfunction in amyloid precursor protein transgenic mice: contribution of soluble and insoluble amyloid-beta peptide, partial restoration via gamma-secretase inhibition," The Journal of neuroscience : the official journal of the Society for Neuroscience 28:13542-13550 (2008).

Hara et al., "Suppression of Basal Autophagy in Neural Cells Causes Neurodegenerative Disease in Mice," Nature 441:885-889 (2006).

Miguel et al., Endothelin receptor-specific control of endoplasmic reticulum stress and apoptosis in the kidney, Scientific Reports, 7(1): (2017).

Minami, et al. "Endothelin-1-like immunoreactivity in cerebral cortex of Alzheimer-type dementia" Progress in neuro-psychopharmacology & biological psychiatry 19:509-513 (1995).

Mommsen et al., Productive capacity of alveolar macrophages and pulmonary organ damage after femoral fracture and hemorrhage in IL-6 knockout mice, Cytokine, 53:60-65 (2011).

Moran et al., Prevention of trauma/hemorrhagic shock-induced lung apoptosis by IL-6-mediated activation of Stat3, Clinical and translational science, 2:41-49 (2009).

Morens et al., Dengue and hemorrhagic fever: a potential threat to public health in the United States, JAMA, 299(2):214-6 (2008).

Morissette et al., High-throughput crystallization: polymorphs, salts, co-crystals and solvates of pharmaceutical solids, Adv. Drug Deliv. Rev., 56(3):275-300 (Feb. 2004).

Morris, "Developments of a water-maze procedure for studying spatial learning in the rat," Journal of neuroscience methods 11:47-60 (1984).

Morrison et al., "Hypotensive Resuscitation Strategy Reduces Transfusion Requirements and Severe Postoperative Coagulopathy in Trauma Patients with Hemorrhagic Shock: Preliminary Results of a Randomized Controlled Trial," The Journal of Trauma Injury, Infection, and Critical Care 70(3):652-663 (2011).

Murphy, "Plasticity during stroke recovery: from synapse to behaviour," Nature reviews Neuroscience 10:861-872 (2009).

Murray, et al., "Membrane-mediated amyloidogenesis and the promotion of oxidative lipid damage by amyloid beta proteins," The Journal of biological chemistry 282:9335-9345 (2007).

Murray, et al., "Promotion of oxidative lipid membrane damage by amyloid beta proteins," Biochemistry 44:12606-12613 (2005).

Murti et al., Synthesis and Osar of 1-aryl-4-(β-2-quinolyl/1-isoquinolylethyl)piperazines and some related compounds as hypotensive agents Indian Journal of Chemistry 28B:934-942 (1989).

Muruganandham et al., Diltiazem enhances tumor blood flow: MRI study in a murine tumor, Int. J. Radiation Oncology Biol. Phys., 43(2):413-21 (1999).

Naftchi et al., "Autonomic Dysreflexia: Pharmacological Management of Hypertensive Crises in Spinal Cord Injured Patients," J Spinal Cord Med 20:355-360 (1997).

Nakayama et al., "Potentiation by endothelin-1 of 5-hydroxytryptamine-induced contraction in coronary artery of the pig," Br J Pharmacol 104:978-986 (1991).

Namas et al., An adequately robust early TNF-alpha response is a hallmark of survival following trauma/hemorrhage, PloS one, 4:e8406 (2009).

Nassif et al., "Autopagy impairment: a crossroad between neurodegeneration and tauopathies," BMC Bioloav 10(78), 4 paaes (2012).

Ngo et al., The Protein Folding Problem and Tertiary Structure Prediction, Chapter 14 in Computational Complexity Protein Structure Prediction and the Levinthal Paradox, pp. 492-495 (1995).

Nishizawa, "Experimental research on neonatal hypoxic ischemic encephalopathy," Academic Dissertation, 8 pages (English translated (pp. 1-4) and Japanese (pp. 5-8) versions), (Mar. 24, 1990; Shiga Prefecture).

Nishizawa, "Experimental Studies on Neonatal Hypoxic-ischemic Brain Injury," Academic Dissertation (1990).

Nitta, et al. "B-Amyloid protein-induced Alzheimer's disease animal model," Neuroscience letters 170:63-66 (1994).

Niwa, et al. "Exogenous AB1-40 reproduces cerebrovascular alterations resulting from amyloid precursor protein overexpression in mice," Journal of cerebral blood flow and metabolism: official journal of the International Societv of Cerebral Blood Flow and Metabolism 20:1659-1668 (2000).

Niwa, et al., "AB-peptides enhance vasoconstriction in cerebral circulation," American journal of physiology Heart and circulatory physiology 281:H2417-2424 (2001).

Niwa, et al., "Cerebrovascular autoregulation is profoundly impaired in mice overexpressing amyloid precursor protein, " American journal of physiology Heart and circulatory physiology 283:H315-323 (2002).

Notification of Reasons for Refusal (English translation), Japanese patent application No. 2015-529776, dated Apr. 12, 2016.

Nowacka, et al., "Vascular endothelial growth factor (VEGF) and its role in the central nervous system: a new element in the neurotrophic hypothesis of antidepressant drug action," Neuropeptides 46:1-10 (2012).

Nowicki et al., "Endothelin-1 in Human Intestine Resected for Necrotizing Enterocolitis," J Pediatr 146:805-810 (2005).

Nunomura, et al., "Oxidative damage is the earliest event in Alzheimer disease," Journal of neuropatholo.ov and experimental neuroloav 60:759-767 (2001).

Nv et al., N-Suc-[Glu9, Ala11, 15]ET-1 (8-21) increases blood perfusion and enhances paclitaxel delivery to the tumor, 96th Annual Meeting of the American Association for Cancer Research, Abstract 5741 (2005).

O'Donnell et al., Pharmacokinetics of centhaquin citrate in a dog model, J. Pharm. Pharmacol., 68:803-809 (2016).

O'Donnell et al., Pharmacokinetics of centhaquin citrate in a rat model, J. Pharm. Pharmacol., 68:56-62 (2016).

Ogunshola, et al. "Neuronal VEGF expression correlates with angiogenesis in postnatal developina rat brain," Brain research Developmental brain research 119:139-153 (2000).

Ohkawa, et al. "Assay for lipid peroxides in animal tissues by thiobarbituric acid reaction," Analytical biochemistry 95:351-358 (1979).

Ouchi et al., "Central effect of endothelin on blood pressure in conscious rats," Am J Physiol 256:H1747-H1751 (1989).

Pacher et al., Measurement of cardiac function using pressure-volume conductance catheter technique in mice and rats, Nature protocols, 3:1422-1434 (2008).

Pai et al., "Clonidine Poisoning," Pediatrics 58:749-750 (1976).

Pannen et al., "Role of Endothelins and Nitric Oxide in Hepatic Reperfusion Injury in the Rat," Hepatology, 27(3):755-764 (1998).

Paris, et al. "Nilvadipine antagonizes both Abeta vasoactivity in isolated arteries, and the reduced cerebral blood flow in APPsw transaenic mice," Brain research 999:53-61 (2004).

Patel et al., Endothelin receptor mediated constriction and dilatation in feline cerebral resistance arterioles in vivo, Eur. J. Pharmacol., 307:41-8 (1996).

Patel, et al., "Therapeutic potential of endothelin receptor antagonists in experimental stroke," Journal of cardiovascular pharmacology 26 Suppl 3:S412-415 (1995).

Peake et al., Interleukin-6 signalling in juvenile idiopathic arthritis is limited by proteolytically cleaved soluble interleukin-6 receptor, Rheumatology, 45:1485-1489 (2006).

(56)          References Cited

OTHER PUBLICATIONS

Pernow et al., Enhanced vasoconstrictor response to endothelin-B-receptor stimulation in patients with atherosclerosis, Journal of cardiovascular pharmacology, 36:S418-420 (2000).

Pfeifer et al., Role of hemorrhage in the induction of systemic inflammation and remote organ damage: analysis of combined pseudo-fracture and hemorrhagic shock, J. Orthop. Res., 29(2):270-4 (2011).

Philipp et al., "Placental 2-adrenoceptors control vascular development at the interface between mother and embrvo," Nature Genetics 31(3):311-315 (2002).

Phillips, "The challenge of gene therapy and DNA delivery," J. Pharm. Pharmacol., 53(9):1169-74 (2001).

Premaratna et al., Should colloid boluses be prioritized over crystalloid boluses for the management of dengue shock syndrome in the presence of ascites and pleural effusions?, BMC Infect. Dis., 11:52 (2011).

Quinn, "Comparing rat's to human's age: how old is my rat in people years?" Nutrition 21:775-777 (2005).

Radovits et al., "Endothelial dysfunction after hypoxia-reoxygenation: Do in vitro models work," Vascul Pharmacol 51:37-43 (2009).

Rai et al., Evidence for the involvement of ET(B) receptors in ET-1-induced changes in blood flow to the rat breast tumor, Cancer Chemother. Pharmacol., 51(1):21-8 (2003).

Ranjit et al., "Aggressive managemenet of dengue shock syndrome may decrease mortality rate: A suaaested protocol," Pediatr Crit Care Med 6(4):412-9 (2005).

Arai et al., Cloning and expression of a cDNA encoding an endothelin receptor, Nature, 348:730-732 (1990).

Atreya et al., Blockade of interleukin 6 trans signaling suppresses T-cell resistance against apoptosis in chronic intestinal inflammation: evidence in crohn disease and experimental colitis in vivo, Nature medicine, 6(5):583-588 (2000).

Briyal et al., Stimulation of endothelin B receptors by IRL-1620 decreases the progression of Alzheimer's disease, Neuroscience, 301:1-11 (2015).

Bruce et al., Altered neuronal and microglial responses to excitotoxic and ischemic brain injury in mice lacking TNF receptors, Nature medicine, 2(7):788-794 (1996).

Buehler et al., Resuscitative effects of polynitroxylated alphaalpha-cross-linked hemoglobin following severe hemorrhage in the rat, Free radical biology & medicine, 29(8):764-774 (2000).

Chang et al., Plasma endothelin level changes during hemorrhagic shock, The Journal of trauma, 35(6):825-833 (1993).

Chaudry et al., Hemorrhage and resuscitation: immunological aspects, The American journal of physiology, 259:R663-678 (1990).

Davis et al., Base deficit is superior to pH in evaluating clearance of acidosis after traumatic shock, The Journal of trauma, 44(1):114-118 (1998).

Fontanilla et al., Anti-interleukin-6 antibody treatment restores cell-mediated immune function in mice with acute ethanol exposure before burn trauma, Alcoholism, clinical and experimental research, 24(9):1392-1399 (2000).

Gadient et al., Interleukin-1 beta and tumor necrosis factor-alpha synergistically stimulate nerve growth factor (NGF) release from cultured rat astrocytes, Neuroscience letters, 117(3):335-340 (1990).

Gado et al., Role of Interleukin-6 in the pathogenesis of multiple myeloma, Cell biology international, 24(4):195-209 (2000).

Gulati et al., Efficacy of centhaquin as a small volume resuscitative agent in severely hemorrhaged rats, Am. J. Emerg. Med., 31:1315-1321 (2013).

Gulati et al., Human Pharmacokinetics of Centhaquin Citrate, a Novel Resuscitative Agent, Circulation, 134(Suppl 1):A16607-A16607 (2016).

Hama et al., Interleukin-6 as a neurotrophic factor for promoting the survival of cultured basal forebrain cholinergic neurons from postnatal rats, Neuroscience letters, 104:340-344 (1989).

Hercule et al., Cytochrome P450 omega/omega-1 hydroxylasederived eicosanoids contribute to endothelin(A) and endothelin(B) receptor-mediated vasoconstriction to endothelin-1 in the rat preglomerular arteriole, The Journal of pharmacology and experimental therapeutics, 292:1153-1160 (2000).

Kitamura et al., Immunoreactive endothelin in rat kidney inner medulla: marked decrease in spontaneously hypertensive rats, Biochemical and biophysical research communications, 162:38-44 (1989).

Lodge et al., Functional role of endothelin ETA and ETB receptors in venous and arterial smooth muscle, European journal of pharmacology, 287:279-285 (1995).

Maggi et al., Suitability of urethane anesthesia for physiopharmacological investigations in various systems. Part 2: Cardiovascular system, Experientia, 42:292-297 (1986).

Marik et al., The immune response to surgery and trauma: Implications for treatment, The journal of trauma and acute care surgery, 73:801-808 (2012).

Mathison et al., Endothelin ET(B) receptor subtype mediates nitric oxide/cGMP formation in rat adrenal medulla, Brain Res Bull, 45:15-19 (1998).

Mees et al., Inhibition of interleukin-6-transsignaling via gp130-Fc in hemorrhagic shock and sepsis, The Journal of surgical research, 157:235-242 (2009).

Oberholzer et al., Cytokine signaling—regulation of the immune response in normal and critically ill states, Critical care medicine, 28:N3-12 (2000).

Paladino et al., The utility of base deficit and arterial lactate in differentiating major from minor injury in trauma patients with normal vital signs, Resuscitation, 77:363-368 (2008).

Papalexopoulou et al., Centhaquin Effects in a Swine Model of Ventricular Fibrillation: Centhaquin and Cardiac Arrest, Heart Lung and Circulation, 26:856-863 (2017).

Papapanagiotou et al., Centhaquin improves survival in a swine model of hemorrhagic shock, The Journal of surgical research, 200:227-235 (2016).

Sanchez et al., Endothelin A (ET(A)) receptors are involved in augmented adrenergic vasoconstriction and blunted nitric oxide-mediated relaxation of penile arteries from insulin-resistant obese zucker rats, J. Sex Med., 11:1463-1474 (2014).

Sharma et al., Decompensation characterized by decreased perfusion of the heart and brain during hemorrhagic shock: role of endothelin-1, The Journal of trauma, 53:531-536 (2002).

Virdis et al., Vascular inflammation: a role in vascular disease in hypertension?, Current opinion in nephrology and hypertension, 12:181-187 (2003).

White et al., Cytokine enhancement of endothelin ET(B) receptor-mediated contraction in human temporal artery, European journal of pharmacology, 406:117-122 (2000).

Yangs et al., Antirat soluble IL-6 receptor antibody down-regulates cardiac IL-6 and improves cardiac function following trauma-hemorrhage, Journal of molecular and cellular cardiology, 42:620-630 (2007).

Taylor et al., "Toxic Proteins In Neurodegenerative Disease," Science 296:1991-1995 (2002).

Thakali et al., Pharmacological endothelin receptor interaction does not occur in veins from ET(B) receptor deficient rats, Vascul. Pharmacol., 49:6-13 (2008).

Timmermans et al., "Postsynaptic a1- and a2-Adrenoceptors in the Circulatory System of the Pithed Rat: Selective Stimulation of the a2-Type by B-HT 933," Eur J Pharmacol 63:199-202 (1980).

Tirapelli, et al., "Functional characterization and expression of endothelin receptors in rat carotid artery: involvement of nitric oxide, a vasodilator prostanoid and the opening of K+ channels in ETB-induced relaxation," British journal of pharmacology 146:903-912 (2005).

Toda, et al., "Cerebral blood flow regulation by nitric oxide: recent advances," Pharmacological reviews 61:62-97 (2009).

Tolentino, et al. "Role of Centhaauin in the Resuscitation of Hemorrhaaic Shock," Chest. 2011.

Trollmann, et al., "HIF-1-regulated vasoactive systems are differentially involved in acute hypoxic stress responses of the developing brain of newborn mice and are not affected by levetiracetam," Brain research 1199:27-36 (2008).

Troncoso et al., "Hypertensive Urgency with Clonidine and Mirtazepine," Psychosomatics 45:449-450 (2004).

(56) References Cited

OTHER PUBLICATIONS

Tsukahara, et al., "Molecular and functional characterization of the non-isopeptide-selective ETB receptor in endothelial cells," Receptor coupling to nitric oxide synthase. The Journal of biological chemistry 269:21778-21785 (1994).

Tsukuda, et al., "Cognitive deficit in amyloid-β-injected mice was improved by pretreatment with a low dose of telmisartan partly because of peroxisome proliferator-activated receptor-? activation," Hypertension 54:782-787 (2009).

U'Prichard et al., "Binding Characteristics of a Radiolabeled Agonist and Antagonist at Central Nervous System Alpha Noradrenergic Receptors," Mol Pharmacol 13:454-473 (1977).

Vacher et al., "Rigid Analogues of the a2-Adrenergic Blocker Artipamezole: Small Changes, Big Consequences," Journal of Medicinal Chemistry 53(19):6986-95 (2010).

Van Zwieten et al., "The Hypotensive Activity and Side Effects of Methyldopa, Clonidine, and Guanfacine," Hypertension 6:1128-33 (1984).

Vassileva et al., Functional role of ETB receptors in the renal medulla, Hypertension, 41:1359-1363 (2003).

Vazquez-Prado et al., "Activiation of Endothelin ETA Receptors Induces Phosphorylation of a1b-Adrenoreceptors in Rat-1 Fibroblasts," J Biol Chem 272:27330-27337 (1997).

Mdovic et al., Deficiency in endothelin receptor B reduces proliferation of neuronal progenitors and increases apoptosis in postnatal rat cerebellum, Cell Mol. Neurobiol., 28:1129-1138 (2008).

Vincenzi et al., Small volume resuscitation with 3% hypertonic saline solution decrease inflammatory response and attenuates end organ damage after controlled hemorrhagic shock, Am. J. Surg., 198:407-414 (2009).

Viossat, et al., "Elevated tissue endothelin content during focal cerebral ischemia in the rat," Journal of cardiovascular pharmacology 22 Suppl 8:S306-309 (1993).

Vippagunta et al., Crystalline solids, Adv. Drug Deliv. Rev., 48(1):3-26 (May 2001).

Virgintino, et al. "VEGF expression is developmentally regulated during human brain angiogenesis," Histochem Cell Biol 119:227-232 (2003).

Virtanen et al., "Highly Selective and Specific Antagonism of Central and Peripheral a2-Adrenoceptors by Atipamezole," Arch. Int. Pharmacodyn. 297:190-204 (1989).

Watters et al., "Fluid Resuscitation Increases Inflammatory Gene Transcription After Traumatic Injury," J Trauma 61(2):300-309 (2006).

Watts et al., Hypothermic coagulopathy in trauma: effect of varying levels of hypothermia on enzyme speed, platelet function, and fibrinolytic activity, J. Trauma, 44(5):846-54 (1998).

Watts, "5-Hydroxytryptamine-Induced Potentiation of Endothelin-1- and Norepinephrine-Induced Contraction Is Mitogen-Activated Protein Kinase Pathway Dependent," Hypertension 35:244-248 (2000).

Watts, "The love of a lifetime: 5-HT in the cardiovascular system," Am J Physiol Regul Integr Comp Physiol R252-R256 (2009).

Weller, et al., "Cerebral amyloid angiopathy: amyloid beta accumulates in putative interstitial fluid drainage pathways in Alzheimer's disease," The American journal of pathology 153:725-733 (1998).

Wells, "Additivity of Mutational Effects in Proteins," Biochem., 29(37):8509-17 (1990).

Wikipedia article, "Ketoacidosis" (Sep. 10, 2008) downloaded from https://web.archive.org/web/20080910125816/http://en.wikipedia.org/wiki/K-etoacidosis on Oct. 19, 2014.

Wiklund et al., "Inhibition of adrenergic neuroeffector transmission by endothelin in the guinea-pig femoral artery," Acta Physiol Scand 134:311-312 (1988).

Williamson et al., "Pain: a review of three commonly used pain rating scales," J. Clin Nurs. 14:798-804 (2005).

Wills et al., Comparison of three fluid solutions for resuscitation in dengue shock syndrome, N. Engl. J. Med., 353(9):877-89 (2005).

Wise, et al. "New clinical guidelines for stroke published," BMJ 320:823 (2000).

Wu et al., "Recent discovery and development of endothelin receptor antagonists," Exp. Opin. Ther. Patents 10(11):1653-1668 (2000).

Wu et al., Low-volume resuscitation from traumatic hemorrhagic shock with Na+/H+ exchanger inhibitor, Critical care medicine, 37:1994-1999 (2009).

Yagami et al., Effects of an endothelin B receptor agonist on secretory phospholipase A2-IIA-induced apoptosis in cortical neurons, Neuropharmacology, 48(2):291-300 (2005).

Yagami, et al. "Effects of endothelin B receptor agonists on amyloid beta protein (25-35)-induced neuronal cell death," Brain research 948:72-81 (2002).

Yanagisawa et al., A novel potent vasoconstrictor peptide produced by vascular endothelial cells, Nature, 332:411-415 (1988).

Yeager et al., Endothelin-1, the unfolded protein response, and persistent inflammation: role of pulmonary artery smooth muscle cells, American journal of respiratory cell and molecular biology, 46:14-22 (2012).

Yoshizawa, et al. "Cerebrospinal fluid endothelin-1 in Alzheimer's disease and senile dementia of Alzheimer type," Neuropeptides 22:85-88 (1992).

Zacharias et al., "Histone Deacetylase Inhibitors Prevent Apoptosis following Lethal Hemorrhagic Shock in Rodent Kidney Cells," Resuscitation 82(1):105-109 (2011).

Zhang, et al. "A selective endothelin ET(A) receptor antagonist, SB 234551, improves cerebral perfusion following permanent focal cerebral ischemia in rats," Brain research 1045:150-156 (2005).

Zhang, et al. "Astrocytes in Alzheimer's disease express immunoreactivity to the vaso-constrictor endothelin-1," Journal of the neurological sciences 122:90-96 (1994).

Zhang, et al., "Neurorestorative therapies for stroke: underlying mechanisms and translation to the clinic," Lancet Neurol 8:491-500 (2009).

Zhang, et al., "Synergistic effect of an endothelin type A receptor antagonist, S-0139, with rtPA on the neuroprotection after embolic stroke," Stroke; a journal of cerebral circulation 39:2830-2836 (2008).

Zlokovic, "New therapeutic targets in the neurovascular pathway in Alzheimer's disease," Neurotherapeutics : the journal of the American Society for Experimental NeuroTherapeutics 5:409-414 (2008).

Zuccarello, M., et al., "Endothelin B Receptor Antagonists Attenuate Subarachnoid Hemorrhage-Induced Cerebral Vasospasm," Stroke, Journal of the American Heart Association, Sep. 1998, vol. 29, No. 9, pp. 1924-1929.

Diebel et al., Systemic Not Just Mesenteric Lymph Causes Neutrophil Priming After Hemorrhagic Shock, J Trauma, 66:1625-1631 (2009).

Gulati et al., Centhaquin Decreases the Requirement of Norepinephrine, Maintains Blood Pressure and Improves Survival Following Resuscitation of Hemorrhaged Rats, Critical Care Medicine, 39(12):414 (Dec. 2011).

Gulati et al., Poster Presented at Annual Meeting of American Heart Association, Anaheim, CA. (Nov. 12, 2017).

* cited by examiner (To be continued)

(Continuation)

(To be continued)

(To be continued)

(To be continued)

G 1    2    3    4    5

$ET_A$ (46 kDa)

β-tubulin (55 kDa)

Abdominal aorta-$ET_A$

(Continuation)

(To be continued)

(To be continued)

(To be continued)

(Continuation)

ALTERATIONS IN ENDOTHELIN RECEPTORS FOLLOWING HEMORRHAGE AND RESUSCITATION BY CENTHAQUIN

CROSS REFERENCE TO RELATED APPLICATIONS

This application is a U.S. National Phase of International Application No. PCT/US2019, filed May 3, 2019, which claims the priority benefit under 35 U.S.C. § 119(e) of U.S. Provisional Patent Application No. 62/666,675, filed May 3, 2018, and Indian Application No. 201841019588, filed May 25, 2018, the disclosures of which are incorporated herein by reference in their entirety.

FIELD OF THE INVENTION

The present disclosure is related to methods and compositions for treating or preventing kidney injury or failure, comprising administering an endothelin B ($ET_B$) receptor agonist and/or an $\alpha_2$ adrenergic agent.

INCORPORATION BY REFERENCE OF MATERIALS SUBMITTED ELECTRONICALLY

This application contains, as a separate part of the disclosure, a Sequence Listing in computer readable form (Filename: 50000A_Seqlisting.txt; Size: 673 bytes; Created: May 2, 2019), which is incorporated by reference in its entirety.

BACKGROUND

Hemorrhagic shock often leads to multiple organ failure due to inadequate blood circulation, perfusion and oxygenation as a result of rapid and excessive blood loss (Wu et al. 2009). Multiple compensatory mechanisms to preserve oxygenation and tissue blood flow are initiated with the onset of hemorrhage. Despite resuscitation with intravenous fluids to restore circulation and oxygen delivery, patients may still undergo irreversible loss of blood perfusion, coagulopathy, hypothermia, acidosis, immune suppression, systemic inflammation, oxidative stress, multiple organ failure, and death (Acosta et al. 1998; Jacob and Kumar 2014). Deaths from hemorrhagic shock typically occur very early, mostly within the first 6 hours of admission (Shackford et al. 1993).

Endothelin (ET), an endogenous 21 amino acid peptide, was first isolated from porcine aortic endothelial cells nearly 3 decades ago (Yanagisawa et al. 1988). There are 3 distinct isopeptides: ET-1, ET-2, and ET-3, which are present in various mammalian tissues performing a myriad of physiological and pathological roles such as regulation of blood pressure and perfusion, apoptosis and cellular proliferation and migration (Ehrenreich et al. 2000; Inoue et al. 1989; Vidovic et al. 2008; Yanagisawa et al. 1988). The ET peptides produce their biological effects through activation of G-protein-coupled receptors: $ET_A$ and $ET_B$ (Arai et al. 1990). However, ET-1 and its receptors are not limited to the vascular system.

SUMMARY OF THE INVENTION

In some aspects, the present disclosure is directed to use of the $ET_B$ receptor agonist, IRL-1620, and an adrenergic agent, centhaquin, in the treatment of acute kidney failure. In particular, it has unexpectedly been found that overexpression or stimulation of $ET_B$ receptors significantly increases renal blood perfusion.

In further aspects, the disclosure is directed to administration of a specific agonist for $ET_B$ receptors alone or in combination with centhaquin to an individual in need thereof. In some embodiments, administration of an $ET_B$ receptor agonist alone or in combination with centhaquin prevents or treats acute kidney injury.

In some aspects, the disclosure provides a method of preventing or treating kidney injury or failure by administering a therapeutically effective amount of an endothelin B ($ET_B$) receptor agonist to an individual in need thereof. In some embodiments, the $ET_B$ receptor agonist is selected from the group consisting of N-Succinyl-[Glu$^9$, Ala$^{11,15}$] endothelin 1 (IRL-1620), BQ-3020, [Ala$^{1,3,11,15}$]-endothelin, sarafotoxin S6c, and endothelin 3. In further embodiments, the $ET_B$ receptor agonist is administered at a dose ranging from about 0.0001 mg/kg to about 0.5 mg/kg. In some embodiments, the method comprises administering multiple doses of the $ET_B$ receptor agonist. In still further embodiments, the administering comprises a single dose of the $ET_B$ receptor agonist. In some embodiments, the method further comprises administering a therapeutically effective amount of centhaquin or a salt thereof to the individual.

In some embodiments, the kidney injury or failure is acute. In further embodiments, the kidney failure results from exposure to radiocontrast media, a non-steroidal anti-inflammatory drug (NSAID), an antibiotic, a chemotherapeutic agent, nivolumab-induced acute granulomatous tubulointerstitial nephritis or a nephrotoxic drug. In some embodiments, the acute kidney failure is caused by or is associated with critical illness, reduced cardiac output, trauma, reduced blood oxygenation, systemic toxicity caused by reaction to injury in another organ, systemic hypotension resulting from cardiorenal syndrome, cardiac surgery or acute decompensated heart failure, a reduction in circulating volume due to hemorrhage, septic shock, hypovolemic shock, severe dengue, a surgical procedure, rhabdomyolysis or a reduction in local renal blood flow resulting from hepatorenal syndrome or liver transplant, or dehydration caused by diarrhea, vomiting, diuretics or excessive sweating.

In some embodiments, kidney glomerular filtration rate of the individual is improved. In further embodiments, serum creatinine level of the individual is reduced.

In some aspects, the disclosure provides a composition comprising (a) an endothelin-B ($ET_B$) receptor agonist, (b) centhaquin or a salt thereof, and optionally (c) an excipient.

In further aspects, the disclosure provides an article of manufacture comprising: (a) a packaged composition comprising an endothelin-B ($ET_B$) receptor agonist and centhaquin or a salt thereof; (b) an insert providing instructions for a simultaneous or sequential administration of the $ET_B$ receptor agonist and the centhaquin or salt thereof to treat a patient; and (c) a container for (a) and (b). In some embodiments, the endothelin-B ($ET_B$) receptor agonist is N-Succinyl-[Glu$^9$, Ala$^{11,15}$] endothelin 1 (IRL-1620).

In some aspects, the disclosure provides a method of treating an individual suffering acute kidney function decline comprising administering to the individual a therapeutically effective amount of a composition comprising centhaquin or a salt thereof. In some embodiments, the acute kidney function decline is associated with acute kidney failure. In some embodiments, the causes of acute decline in kidney functions are prerenal due to decreased blood flow to the kidney, intrinsic where the tissues within the kidneys are directly damaged, and postrenal where the urine flow is blocked. In some embodiments, the acute kidney failure is caused by or is associated with critical illness, reduced cardiac output, trauma, reduced blood oxygenation, systemic toxicity caused by reaction to injury in another organ, systemic hypotension resulting from cardiorenal syndrome, cardiac surgery or acute decompensated heart failure, a reduction in circulating volume due to hemorrhage, septic shock, hypovolemic shock, severe dengue, a surgical procedure, rhabdomyolysis or a reduction in local renal blood flow resulting from hepatorenal syndrome or liver transplant, nephrotoxicity resulting from drugs, radiocontrast media, a non-steroidal anti-inflammatory drug (NSAID), an antibiotic, or a chemotherapeutic agent, or dehydration caused by diarrhea, vomiting, diuretics or excessive sweating.

In some aspects, the disclosure provides a method of treating an individual suffering from kidney injury comprising administering an effective amount of a composition comprising centhaquin or a salt thereof. In some embodiments, the kidney injury results from an ischemic event or an ischemic reperfusion event. In further embodiments, the salt is citrate, pyruvate, or lactate. In some embodiments, centhaquin or salt thereof is administered at a dose of about 0.0001 mg/kg to about 1.0 mg/kg. In further embodiments, centhaquin or salt thereof is administered in single or multiple doses.

BRIEF DESCRIPTION OF THE FIGURES

FIG. 9 shows results of the phase I study of centhaquin as a resuscitative agent for hypovolemic shock due to excessive blood loss in which systolic and diastolic blood pressure were determined when the patient was inducted in the study (baseline) and at the time of discharge from hospital (end of the study). An interim analysis showed that blood pressure increase in centhaquin treated patients was more than that observed in control cohort. These results indicated that centhaquin is an effective resuscitative agent and improved the outcome of patients of hypovolemic shock.

DETAILED DESCRIPTION

Figure 1:
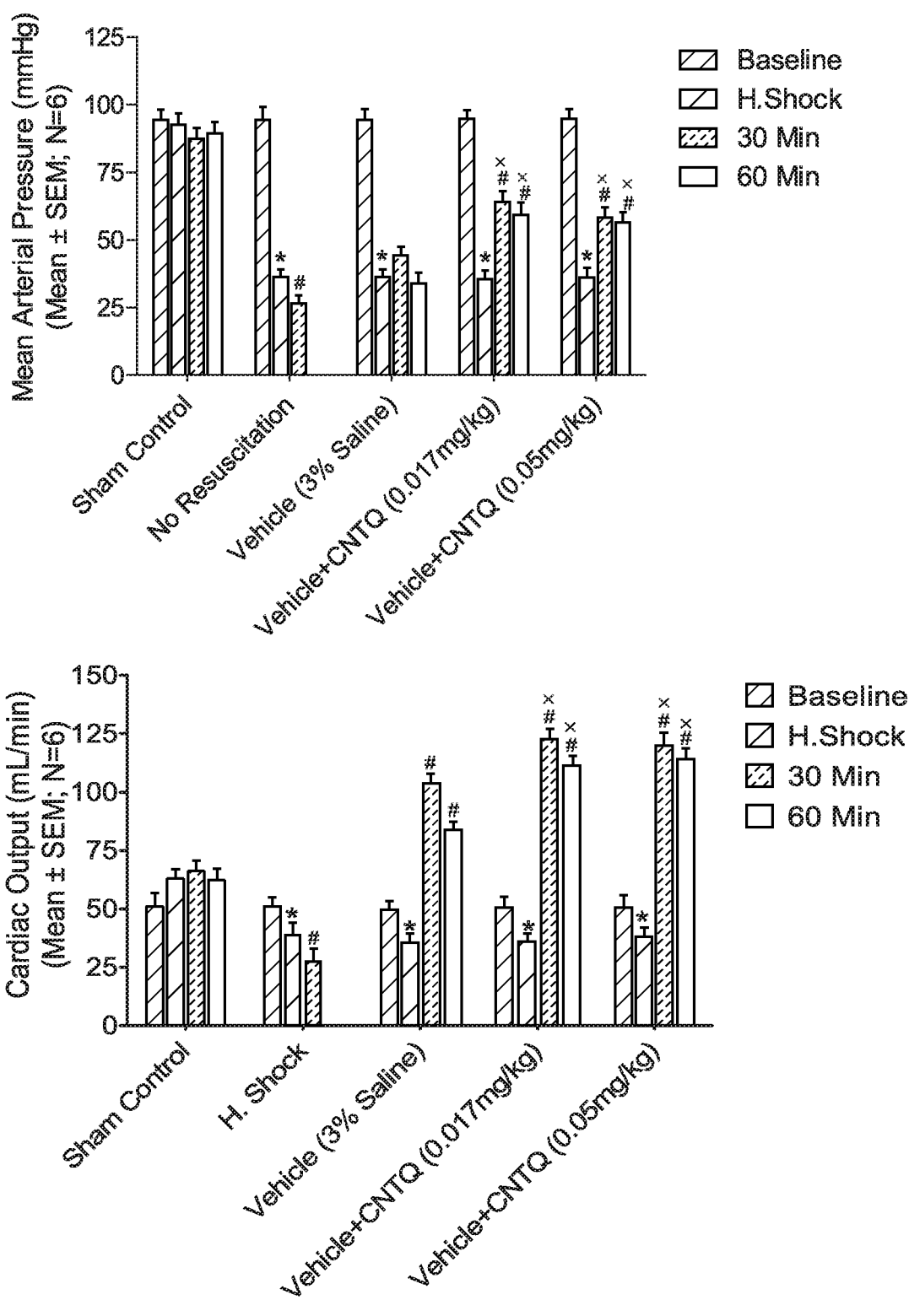
FIG. 1 shows the effect of hemorrhage on mean arterial pressure, heart rate, cardiac output and systemic vascular resistance in sham and hemorrhaged rats. Hemorrhaged rats were resuscitated with hypertonic saline or centhaquin. The values are expressed as mean±S.E.M. (n=5). *p<0.05 compared to baseline, #p<0.05 compared to hemorrhage, xp<0.05 compared to vehicle treated group.
Figure 1:
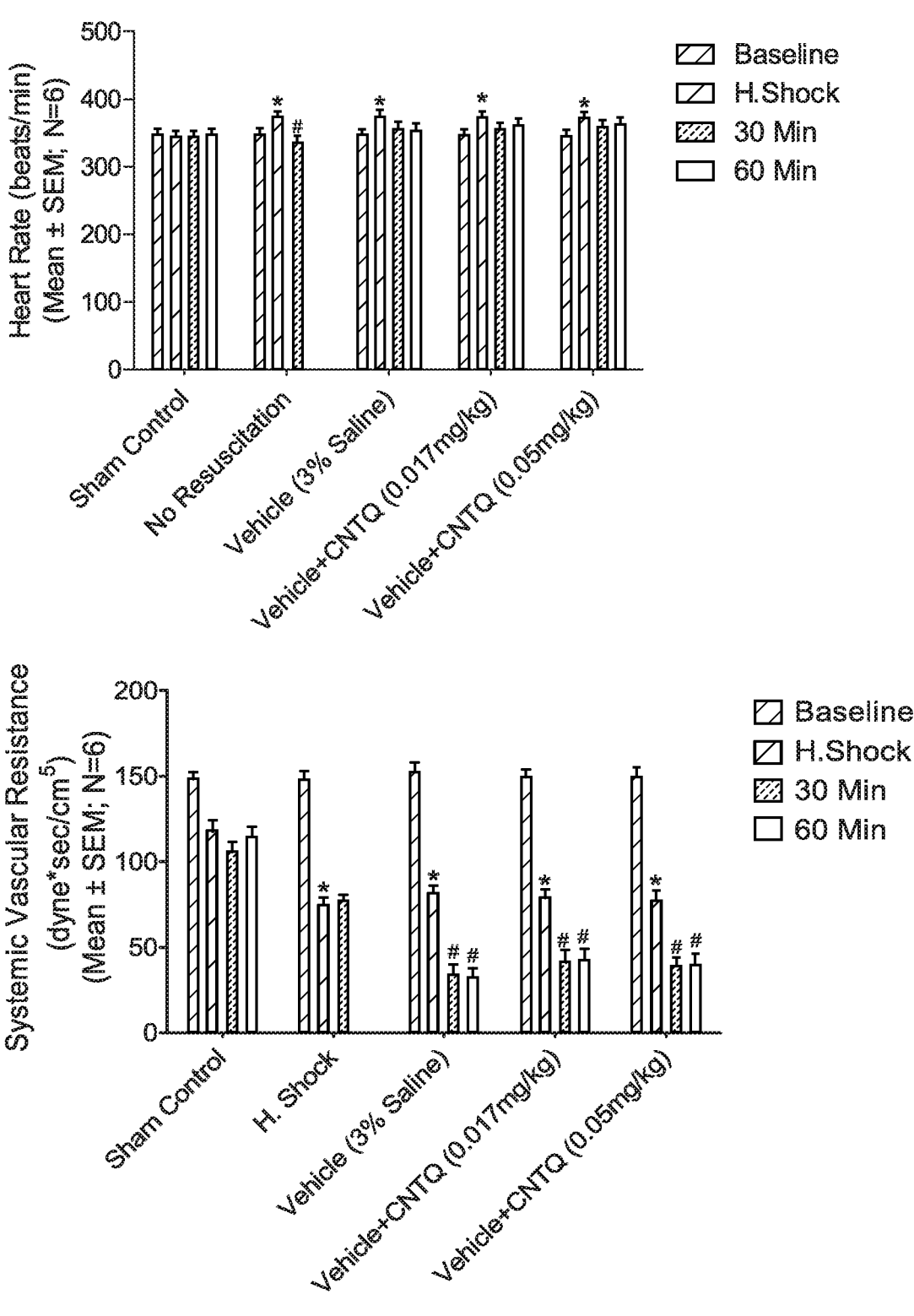

It has been established that low doses of centhaquin (2-[2-(4-(3-methyphenyl)-1-piperazinyl)]ethyl-quinoline) citrate, significantly decreased blood lactate, and increased mean arterial pressure (MAP), pulse pressure (PP) and cardiac output (CO) in hemorrhagic shock (Gulati et al. 2012; Gulati et al. 2013; Lavhale et al. 2013; Papapanagiotou et al. 2016). Comparative studies (see Example 2) were performed between centhaquin and status quo resuscitative agents grouped into 3 different categories: (a) fluids such as Lactated Ringer's, hypertonic saline; (b) adrenergic agents such as norepinephrine, and (c) fresh blood. Results using (i) a rat model of fixed pressure blood loss, (ii) a rabbit model of uncontrolled bleeding with trauma, and (iii) a pig model of massive blood loss indicate that centhaquin is highly effective in reducing the mortality following hypovolemic shock (Gulati et al. 2012; Gulati et al. 2013; Lavhale et al. 2013; Papapanagiotou et al. 2016). Unlike other resuscitative agents (vasopressors), centhaquin increased MAP by increasing stroke volume (SV) and CO; and decreased heart rate and systemic vascular resistance (SVR).

Elevated plasma ET-1 levels during hemorrhagic shock along with a decrease in blood flow to the kidneys and the lungs have been previously reported (Chang et al. 1993; Edwards et al. 1994). A decrease in pulmonary and renal blood flow following hemorrhagic shock, causing reduced clearance of ET-1, may be responsible for an increase in circulating plasma ET-1 which plays an important role in maintaining vascular tone and tissue blood perfusion (Chang et al. 1993). Circulating ET-1 may regulate cardiovascular system following hemorrhagic shock by acting on $ET_A$ receptors, as a vasoconstrictor and on $ET_B$ receptors as a vasodilator to maintain vascular tone (Bourque et al. 2011; Cardillo et al. 2000; Helmy et al. 2001; Sandoo et al. 2010).

Centhaquin is currently in clinical development as a resuscitative agent for hemorrhagic shock. Without wishing to be bound by theory, the proposed mechanism is that centhaquin acts on venous $\alpha_{2B}$ adrenergic receptors to produce constriction and increase venous return to the heart and stimulate central $\alpha_{2A}$ adrenergic receptors to produce a decrease in SVR. However, adrenergic receptors have been shown to be modulated by endothelin (ET) receptors (Gulati 1992; Gulati and Srimal 1993; Lavhale et al. 2010; Sanchez et al. 2014) therefore, it is possible that ET receptors may be involved in the mechanism of action of centhaquin in hemorrhagic shock.

Kidney Injury/Failure

Acute renal failure is the sudden loss of the kidney's ability to filter wastes without losing electrolytes. Most often, acute renal failure (also termed acute kidney injury or AKI) is caused by reduced blood flow to the kidneys (prerenal acute renal failure), though about 20% of the cases are due to infections or toxins affecting the kidneys directly (intrinsic ARF), and about 10% are due to blockages downstream of the kidneys (postrenal obstruction). Acute kidney injury (AKI) has a high prevalence in critical care patients. Early detection might prevent patients from developing chronic kidney disease and requirement for renal replacement therapy. In the majority of hospitalized patients, acute renal failure is caused by acute tubular necrosis, which results from ischemic and/or nephrotoxic insults. Renal hypoperfusion is caused by hypovolemic, cardiogenic and septic shock, by administration of vasoconstrictive drugs or renovascular injury. Nephrotoxins include exogenous toxins such as contrast media and aminoglycosides as well as endogenous toxin such as myoglobin. Studies indicate that apoptosis in renal tissue is prominent in most human cases of acute renal failure, with the principal site of apoptotic cell death being the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum. It has been suggested that apoptotic tubule cell death may be more predictive of functional changes than necrotic cell death (Komarov et al. 1999; Supavekin et al. 2003). An individual at risk for developing ischemic acute renal failure includes individuals with diabetes, underlying renal insufficiency, nephritic syndrome, elderly, atherosclerotic disease, nephrotoxic agent recipients, sepsis, hypotensive individuals, hypoxic individuals, pre-surgery, myoglobinuria-hematuria, pregnancy associated acute renal failure, and liver disease.

The acute kidney injury is characterized by at least one condition selected from the group consisting of an increase in serum creatinine by at least 50% over baseline, an absolute increase in serum creatinine of at least 0.3 mg/dL over baseline, a reduction in glomerular filtration rate of at least 25% compared to baseline, and a decrease in urine output to 0.5 ml per kilogram of body weight or less per hour persisting for at least 6 hours.

The incidence of community acquired acute renal failure (ARF) is only about 100 cases per million population with a mortality rate of 7%. The published incidence of ARF ranges from 1 to 13% of all hospital admissions ($34 \times 10^6$/year in the US) and 20 to 30% of all ICU admissions ($4.4 \times 10^6$/year in the US). Most cases of ARF are acquired in the hospital as a result of complications from other illnesses or interventions. The most common causes are sepsis, hypovolemia, surgery, imaging contrast agents, chemotherapy drugs, NSAIDS, and some antibiotics.

An acute kidney injury may involve a pre-renal kidney injury caused by or associated with a reduced cardiac output leading to reduced overall blood flow to the kidneys, trauma, reduced blood oxygenation, systemic toxicity caused by reaction to injury in another organ, systemic hypotension resulting from cardiorenal syndrome or acute decompensated heart failure, a reduction in circulating volume due to hemorrhage, a surgical procedure, or a reduction in local renal blood flow resulting from hepatorenal syndrome.

In a study, acute kidney injury developed in 52.6% (n=8270) of the entire cohort and in 39.8% of the young adult age group (16-25 years). For the young adult age group, diabetes, surgical reason for admission, severity of illness, hypotension, and certain medications (vancomycin and calcineurin inhibitors) were all independently associated with acute kidney injury. Acute kidney injury was a significant predictor for longer length of stay, intensive care unit mortality, and mortality after discharge. Therefore, acute kidney injury is a common event and is associated with an increased length of stay and a high risk of mortality (Fuhrman et al. 2018).

Using the 2001 National Hospital Discharge Survey, Liangos et al. (2006) found that 1.9% of all hospital discharges showed a code for ARF, which corresponds to a U.S. incidence of 646,000. The mortality rate was 21.3%. The authors validated the study by examining all the 13,237 patients discharged from St. Elizabeth's (Boston) during 2001. It was noted that 2.6% of the patients were coded for ARF, but lab values showed that 12% of the patients had experienced ARF. Thus, ARF is coded on only about 20% of occurrences (presumably the most serious cases) (Liangos et al. 2006).

The treatment of acute renal failure is to give fluids to reverse hypovolemia and flush toxins while waiting for the kidneys to recover. In some instances, the patients retain too much water or their electrolyte balance suffers to such an extent that they require dialysis. The most common causes of death in acute renal failure patients are heart failure, sepsis, and respiratory failure. Patients who recover from acute renal failure show increased odds of death and chronic kidney disease over the following 5 and 10 years. Dozens of new treatments and drugs that showed promise in animals have been tested clinically in acute renal failure patients, but none have demonstrated benefits in randomized clinical trials. Some of the treatments tested include diuretics to increase urine flow, dopamine and atrial natriuretic peptide (ANP) to increase blood flow to the kidneys, many cytoprotective agents to preserve tubule epithelial cells such as free radical scavengers, heat shock proteins, hemeoxygenase, xanthine oxidase inhibitors, prostaglandins, and calcium channel blockers and several growth factors to speed the recovery of the proximal tubules (Allgren et al. 1997; Hirschberg et al. 1999).

Acute kidney injury has been reported after cardiac surgery; liver transplant; severe dengue; septic shock; hypovolemic shock; nephrotoxic drugs such as intravenous radiographic contrast, vancomycin, piperacillin-tazobactam combined with vancomycin, colistin, nivolumab-induced acute granulomatous tubulointerstitial nephritis, anti-cancer drugs, cisplatin-induced acute kidney injury; critically ill patients with solid tumors; Lithiasis-induced acute kidney injury; rhabdomyolysis.

Studies have been conducted to determine the effect of centhaquin on renal medullary blood flow and the results showed that severe hemorrhage produced a decrease in renal medullary blood flow and worsening renal perfusion leading to ischemia and renal failure (Gulati et al. 2016a; Gulati et al. 2017). It is known that the outer renal medulla has a higher metabolic demand and where about 33% of the filtered sodium chloride is reabsorbed by the thick ascending limb of loop of Henle (Cowley 2008). Hence this region is highly prone to hypoxic or ischemic injury following excessive hemorrhage.

Endothelin

Endothelin (ET) is an endogenous peptide which acts on two distinct G-protein-coupled receptors, $ET_A$ and $ET_B$, and performs numerous functions throughout the body (Arai et al. 1990; Goto et al. 1989). The elevated plasma ET-1 levels during hemorrhagic shock along with a decrease in blood flow to the kidneys and the lungs have been previously reported (Chang et al. 1993; Edwards et al. 1994). A decrease in pulmonary and renal blood flow following hemorrhagic shock, causing reduced clearance of ET-1, may be responsible for an increase in circulating plasma ET-1 which plays an important role in maintaining vascular tone and tissue blood perfusion (Chang et al. 1993). Circulating ET-1 may regulate cardiovascular system following hemorrhagic shock by acting on $ET_A$ receptors, as a vasoconstrictor and on $ET_B$ receptors as a vasodilator to maintain vascular tone (Bourque et al. 2011; Cardillo et al. 2000; Helmy et al. 2001; Sandoo et al. 2010). It is therefore of interest to investigate the effect of hemorrhagic shock and resuscitation with centhaquin on changes in $ET_A$ and $ET_B$ receptors in various tissues. In addition, it is known that hemorrhagic shock and resuscitation contribute towards an increased risk of systemic inflammatory response (Chaudry et al. 1990) and ET-1 plays a pivotal role in inflammation following sepsis and hemorrhagic shock (Kowalczyk et al. 2015).

Endothelin B ($ET_B$) Receptor Agonist

The disclosure contemplates the use of an endothelin B ($ET_B$) receptor agonist in the compositions and methods disclosed herein. In various embodiments, the $ET_B$ receptor agonist is selected from the group consisting of N-Succinyl-[Glu$^9$, Ala$^{11,15}$] endothelin 1 (IRL-1620), BQ-3020, [Ala$^{1,3,11,15}$]-endothelin, sarafotoxin S6c, and endothelin 3.

IRL-1620 [N-Succinyl-[Gu$^9$, Ala$^{11,15}$] endothelin 1] is an analog of ET-1 with amino acid sequence Suc-Asp-Glu-Glu-Ala-Val-Tyr-Phe-Ala-His-Leu-Asp-Ile-Ile-Trp (SEQ ID NO: 1), molecular weight of 1821.9. IRL-1620 is a potent and specific agonist for the $ET_B$ receptors, with Ki values for $ET_A$ and $ET_B$ receptors of 1.9 µM and 16 pM, respectively, making it approximately 120,000 times more selective for $ET_B$ over $ET_A$ receptors. IRL-1620 has been used in numerous studies to determine the biological actions of $ET_B$ receptors in the pulmonary, hepatic, renal, gastrointestinal, dermatological and endocrine systems (Bauer et al. 2000; Fellner and Arendshorst 2007; Khan et al. 2006; Lawrence et al. 1995; Mathison and Israel 1998; Mazzoni et al. 1999).

According to the disclosure, the $ET_B$ receptor agonist (e.g., IRL-1620) may be administered at a dose ranging from 0.0001 to 0.5 mg/kg. In further embodiments, the endothelin-B receptor agonist is administered at a dose ranging from about 0.0001 to about 0.5 mg/kg, or from about 0.0001 to about 0.4 mg/kg, or from about 0.0001 to about 0.3 mg/kg, or from about 0.0001 to about 0.2 mg/kg, or from about 0.0001 to about 0.1 mg/kg, or from about 0.001 to about 0.5 mg/kg, or from about 0.001 to about 0.4 mg/kg, or from about 0.001 to about 0.3 mg/kg, or from about 0.001 to about 0.2 mg/kg, or from about 0.001 to about 0.1 mg/kg, or from about 0.01 to about 0.5 mg/kg, or from about 0.01 to about 0.4 mg/kg, or from about 0.01 to about 0.3 mg/kg, or from about 0.01 to about 0.2 mg/kg, or from about 0.01 to about 0.1 mg/kg, or from about 0.0005 to about 0.5 mg/kg, or from about 0.0005 to about 0.4 mg/kg, or from about 0.0005 to about 0.3 mg/kg, or from about 0.0005 to about 0.2 mg/kg, or from about 0.0005 to about 0.1 mg/kg. In additional embodiments, the $ET_B$ receptor agonist (e.g., IRL-1620) is administered at a dose of at least about 0.0001 mg/kg, or at least about 0.0002 mg/kg, or at least about 0.0005 mg/kg, or at least about 0.001 mg/kg, or at least about 0.002 mg/kg, or at least about 0.005 mg/kg, or at least about 0.007 mg/kg, or at least about 0.01 mg/kg, or at least about 0.02 mg/kg, or at least about 0.03 mg/kg, or at least about 0.04 mg/kg, or at least about 0.05 mg/kg, or at least about 0.06 mg/kg, or at least about 0.07 mg/kg, or at least about 0.08 mg/kg, or at least about 0.09 mg/kg, or at least about 0.1 mg/kg, or at least about 0.2 mg/kg, or at least about 0.3 mg/kg, or at least about 0.4 mg/kg. In still further embodiments, the $ET_B$ receptor agonist (e.g., IRL-1620) is administered at a dose of less than about 0.0001 mg/kg, or less than about 0.0002 mg/kg, or less than about 0.0005 mg/kg, or less than about 0.001 mg/kg, or less than about 0.002 mg/kg, or less than about 0.005 mg/kg, or less than about 0.007 mg/kg, or less than about 0.01 mg/kg, or less than about 0.02 mg/kg, or less than about 0.03 mg/kg, or less than about 0.04 mg/kg, or less than about 0.05 mg/kg, or less than about 0.06 mg/kg, or less than about 0.07 mg/kg, or less than about 0.08 mg/kg, or less than about 0.09 mg/kg, or less than about 0.1 mg/kg, or less than about 0.2 mg/kg, or less than about 0.3 mg/kg, or less than about 0.4 mg/kg, or less than about 0.5 mg/kg. In some embodiments, the $ET_B$ receptor agonist (e.g., IRL-1620) is administered at a dose of about 0.1 to about 0.6 μg/kg, or about 0.1 to about 0.5 μg/kg, or about 0.1 to about 0.4 μg/kg, or about 0.1 to about 0.3 μg/kg. In further embodiments, the $ET_B$ receptor agonist (e.g., IRL-1620) is administered at a dose of about 0.1, 0.2, 0.3, 0.4, 0.5, 0.6, 0.7, 0.8, 0.9, or 1.0 μg/kg.

The $ET_B$ receptor agonist (e.g., IRL-1620), in various embodiments, is administered to a patient repeatedly at intervals of 1 to 6 hours. In some embodiments, the $ET_B$ receptor agonist (e.g., IRL-1620) is administered to the patient every 1 to 5 hours, or every 1 to 4 hours, or every 1 to 2 hours, or every hour, or every 2 hours, or every 3 hours, or every 4 hours, or every 5 hours, or every 6 hours. In further embodiments, the $ET_B$ receptor agonist (e.g., IRL-1620) is administered to the patient every two to five days, or every three to five days, or every two days, or every three days, or every four days, or every five days. In some embodiments, $ET_B$ receptor agonist (e.g., IRL-1620) is administered one, two, three, four, or five times per day.

Centhaquin

Centhaquin, an alpha-2 receptor agonist and cardiovascular active agent, has been shown to produce a positive inotropic effect and increased ventricular contractions of the isolated, perfused rabbit heart (Bhatnagar et al. 1985). Direct or indirect positive inotropic effect of centhaquin may lead to an increase in cardiac output (CO). In a study conducted in a swine model of hemorrhagic shock it was found that centhaquin (0.015 mg/kg), when administered in the fluid resuscitation phase, augments CO, reduces systemic vascular resistance (SVR), requires smaller volume of fluids for resuscitation, and results in significantly better survival compared to Lactated Ringer's (LR) (Papalexopoulou et al. 2017; Papapanagiotou et al. 2016).

In another study, centhaquin administered in one-fifth the volume of blood loss, maintained mean arterial pressure (MAP) of hemorrhaged rats for alonger length of time and improved the survival (Gulati et al. 2013). In a rat model of hemorrhagic shock, centhaquin significantly improved CO, decreased blood lactate and improved survival (Gulati et al. 2012; Lavhale et al. 2013). Centhaquin has a half-life of about one hour and a high volume of distribution (Gulati et al. 2016; O'Donnell et al. 2016a; O'Donnell et al. 2016b). Successful chemistry, manufacturing and control along with mice, rat and dog toxicological studies led to successful completion of a human Phase I study of experimental centhaquin. The study was conducted in 24 human subjects and centhaquin was found to be safe and was well tolerated (Gulati et al. 2016). At present multi-centric Phase II studies are ongoing (CTRI/2017/03/008184) in humans with hemorrhagic shock.

It is contemplated that, in addition to centhaquin, other $\alpha_2$ adrenergic agents are useful in the methods of the disclosure. For example and without limitation, the disclosure contemplates the use of an $\alpha_2$ adrenergic agent selected from the group consisting of centhaquin, clonidine, guanfacine, guanabenz, guanoxabenz, guanethidine, xylazine, tizanidine, methyldopa, fadolmidine, amidephrine, amitraz, anisodamine, apraclonidine, brimonidine, cirazoline, detomidine, dexmedetomidine, epinephrine, ergotamine, etilefrine, indanidine, lofexidine, medetomidine, mephentermine, metaraminol, methoxamine, mivazerol, naphazoline, norepinephrine, norfenefrine, octopamine, oxymetazoline, phenylpropanolamine, rilmenidine, romifidine, synephrine, talipexole, salts thereof, and a combination thereof.

Salts of the $\alpha_2$ adrenergic agents also can be used in the present compositions and methods. Examples of suitable salts include, but are not limited to, acid addition salts formed with inorganic acids such as nitric, boric, hydrochloric, hydrobromic, sulfuric, and phosphoric, and organic acids such as oxalic, maleic, succinic, tartaric, and citric. Nonlimiting examples of salts of $\alpha_2$ adrenergic agents include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, undecanoate, lactate, citrate, tartate, gluconate, methanesulfonate, ethanedisulfonate, benzene sulfonate, and p-toluenesulfonate salts.

Preferred salts are salts of organic acids, such as citrate, tartrate, malate, succinate, oxalate, fumarate, maleate, ascorbate, lactate, gluconate, diglyconate, and aspartate, for example. A more preferred salt is a citrate salt, a lactate salt, or a tartrate salt.

Centhaquin, as the free base, may be administered in an amount of 0.001 to less than 0.05 mg per kg of weight of the individual being treated (mg/kg), preferably about 0.003 to about 0.04 mg/kg, and more preferably about 0.005 to about 0.03 mg/kg. More particularly, centhaquin, as the free base, is administered at mg/kg doses of 0.001, 0.002, 0.003, 0.004, 0.005, 0.006, 0.007, 0.008, 0.009, 0.010, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, or 0.049, and all ranges and subranges therein.

Centhaquin also can be administered in the form of salt, e.g., centhaquin citrate, to achieve the benefits of the present methods. Centhaquin citrate is administered in an amount of about 0.0001 to about 1.5 mg/kg, preferably about 0.0002 to about 0.8 mg/kg, and more preferably about 0.0004 to about 0.5 mg/kg. In some embodiments, centhaquin citrate is administered in an amount of about 0.0001 to about 1.0 mg/kg. More particularly, centhaquin citrate can be administered at mg/kg doses (as centhaquin citrate) of about or at least about any of the following doses: 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.010, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.05, 0.051, 0.052, 0.053, 0.054, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, or 1.5, and all ranges and subranges therein.

In some embodiments, the $\alpha_2$ adrenergic agent (e.g., centhaquin or a salt thereof) is coadministered with a resuscitation fluid. The resuscitation fluid can be a colloid solution, a crystalloid solution, blood, a blood component or a blood substitute. Nonlimiting examples of colloid solutions and crystalloid solutions are Ringer's Lactate, saline, hypertonic saline, an albumin solution, a dextran solution, a hydroxyethyl starch solution, a gelatin solution, and a starch solution. Examples of a blood component are plasma, red blood cells, white blood cells, platelets, clotting factors, proteins, and hormones. The blood substitute can be a hemoglobin-based blood substitute or a perflourocarbon-based substitute.

The resuscitation fluid can administered in a volume amount of up to three times the volume amount of fluid, e.g., blood, plasma, water, lost by an individual. In some embodiments, the resuscitation fluid is administered in a volume amount less than and up to the volume amount of fluid lost by the individual, e.g., a volume amount of 5%, preferably 10% or 20%, and up to 100% of the volume amount of lost fluid.

Compositions/Administration

In some aspects, the disclosure provides a composition for treating kidney injury or kidney failure comprising a therapeutically effective amount of an $ET_B$ receptor agonist (e.g., IRL-1620), wherein the therapeutically effective amount is about from about 0.0001 mg/kg to about 0.5 mg/kg. In some embodiments, the composition further comprises a therapeutically effective amount of centhaquin or salt thereof, wherein the therapeutically effective amount of centhaquin or salt thereof is administered at a dose of about 0.0001 mg/kg to about 1.0 mg/kg. In some embodiments, the centhaquin salt is centhaquin citrate.

In some aspects, the disclosure provides a composition for treating acute kidney function decline or kidney injury comprising a therapeutically effective amount of centhaquin or a salt thereof, wherein the therapeutically effective amount of centhaquin or salt thereof is administered at a dose of about 0.0001 mg/kg to about 1.0 mg/kg. In some embodiments, the centhaquin salt is centhaquin citrate.

The pharmaceutical compositions of the disclosure include those wherein the active ingredients are administered in an effective amount to achieve their intended purpose. More specifically, a "therapeutically effective amount" means an amount effective to treat or prevent kidney injury or failure, or to treat acute kidney function decline. Determination of a therapeutically effective amount is well within the capability of those skilled in the art, especially in light of the detailed disclosure provided herein.

A "therapeutically effective dose" refers to the amount of the active agents that results in achieving the desired effect. Toxicity and therapeutic efficacy of such active agents can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. A high therapeutic index is preferred. The data obtained from such data can be used in formulating a range of dosage for use in humans. The dosage of the active agents preferably lies within a range of circulating concentrations that include the $ED_{50}$ with little or no toxicity. The dosage can vary within this range depending upon the dosage form employed, and the route of administration utilized.

For administration to a human in the methods disclosed herein, oral dosages of centhaquin are about 0.01 to about 200 mg daily for an average adult patient (70 kg), typically divided into two to three doses per day. Thus, for a typical adult patient, individual tablets or capsules contain about 0.1 to about 200 mg centhaquin in a suitable pharmaceutically acceptable vehicle or carrier, for administration in single or multiple doses, once or several times per day. Dosages for intravenous, buccal, or sublingual administration typically are about 0.1 to about 10 mg/kg per single dose as required. In practice, the physician determines the actual dosing regimen that is most suitable for an individual patient, and the dosage varies with the age, weight, and response of the particular patient. The above dosages are exemplary of the average case, but there can be individual instances in which higher or lower dosages are merited, and such are within the scope of this disclosure.

As discussed in further detail herein above, dosages of an $ET_B$ receptor agonist (e.g., IRL-1620) are about 0.1 to about 0.6 µg/kg for an average adult patient, typically administered one, two, or three times per day. In some embodiments, the dose of the $ET_B$ receptor agonist (e.g., IRL-1620) is about 0.3 µg/kg, administered one, two, or three times per day. Dosages of the $ET_B$ receptor agonist (e.g., IRL-1620) are in a suitable pharmaceutically acceptable vehicle or carrier. In practice, the physician determines the actual dosing regimen that is most suitable for an individual patient, and the dosage varies with the age, weight, and response of the particular patient. The above dosages are exemplary of the average case, but there can be individual instances in which higher or lower dosages are merited, and such are within the scope of this disclosure.

The active agents of the present disclosure can be administered alone, or in admixture with a pharmaceutical carrier selected with regard to the intended route of administration and standard pharmaceutical practice. Pharmaceutical compositions for use in accordance with the present disclosure thus can be formulated in a conventional manner using one or more physiologically acceptable carriers comprising excipients and auxiliaries that facilitate processing of the active agents into preparations that can be used pharmaceutically.

These pharmaceutical compositions can be manufactured in a conventional manner, e.g., by conventional mixing, dissolving, granulating, dragee-making, emulsifying, encapsulating, entrapping, or lyophilizing processes. Proper formulation is dependent upon the route of administration chosen. When a therapeutically effective amount of the active agents are administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% of an active agent of the present invention, and preferably from about 25% to about 90% of an active agent of the present invention. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.5% to about 90% by weight of active agents, and preferably about 1% to about 50% of an active agents.

When a therapeutically effective amount of the active agents is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present disclosure, an isotonic vehicle.

Suitable active agents can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the active agents with a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

The active agents can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents, such as suspending, stabilizing, and/or dispersing agents.

Pharmaceutical compositions for parenteral administration include aqueous solutions of the active agent in water-soluble form. Additionally, suspensions of the active agents can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a composition of the disclosure can be in powder form for constitution with a suitable vehicle, e.g., sterile pyrogen-free water, before use.

The active agents also can be formulated in rectal compositions, such as suppositories or retention enemas, e.g., containing conventional suppository bases. In addition to the formulations described previously, the active agents also can be formulated as a depot preparation. Such long-acting formulations can be administered by implantation (for example, subcutaneously or intramuscularly) or by intramuscular injection. Thus, for example, the active agents can be formulated with suitable polymeric or hydrophobic materials (for example, as an emulsion in an acceptable oil) or ion exchange resins, or as sparingly soluble derivatives, for example, as a sparingly soluble salt.

In particular, the active agents can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. An active agent also can be injected parenterally, for example, intravenously, intramuscularly, subcutaneously, intrathecally, intracisternally, or intracoronarily. For parenteral administration, the active agent is best used in the form of a sterile aqueous solution which can contain other substances, for example, salts, or monosaccharides, such as mannitol or glucose, to make the solution isotonic with blood.

For veterinary use, the active agents are administered as a suitably acceptable formulation in accordance with normal veterinary practice. The veterinarian can readily determine the dosing regimen and route of administration that is most appropriate for a particular animal.

EXAMPLES

The following examples investigated the effect of hemorrhagic shock and resuscitation with centhaquin on endothelin ($ET_A$ and $ET_B$) receptors in various tissues along with concentration of plasma ET-1 and inflammatory makers in a rat model of hemorrhagic shock.

Endothelin-1 (ET-1) acts on $ET_A$ and $ET_B$ receptors and has been implicated in hemorrhagic shock (shock). The effect of shock and resuscitation on $ET_A$ and $ET_B$ receptor expression was studied utilizing hypertonic saline (saline) or centhaquin. Rats were anesthetized, a pressure catheter was placed in the left femoral artery; blood was withdrawn from the right femoral artery to bring mean arterial pressure (MAP) to 35 mmHg for 30 minutes, resuscitation was performed and 90 minutes later sacrificed to collect samples for biochemical estimations. Resuscitation with centhaquin decreased blood lactate and increased MAP.

Protein levels of $ET_A$ or $ET_B$ receptor were unaltered in the brain, heart, lung and liver following shock or resuscitation. In the abdominal aorta, shock produced an increase (140%) in $ET_A$ expression which was attenuated by saline and centhaquin; $ET_B$ expression was unaltered following shock but was increased (79%) by centhaquin. In renal medulla, $ET_A$ expression was unaltered following shock, but was decreased (−61%) by centhaquin; shock produced a decrease (−34%) in $ET_B$ expression which was completely attenuated by centhaquin and not saline. Shock induced changes in $ET_A$ and $ET_B$ receptors in the aorta and renal medulla are reversed by centhaquin and may be contributing to its efficacy.

Example 1

Methods

Animals. Male Sprague-Dawley rats (340 to 380 g) (Envigo, Indianapolis, IN) were housed for at least 4 days in a room with controlled temperature (23±1° C.), humidity (50±10%) and light (6:00 A.M. to 6:00 P.M.) before being used. Food and water were made available continuously. Animal care and use for experimental procedures were approved by the Institutional Animal Care and Use Committee of the Midwestern University. All anesthetic and surgical procedures were in compliance with the guidelines established by the Animal Care Committee.

Drugs and Chemicals. Centhaquin citrate (PMZ-2010) was synthesized at Pharmazz India Private Limited, Greater Noida, India. Urethane (ethyl carbamate) (Sigma-Aldrich St Louis, MO, USA), Hypertonic Saline Injection, USP (Hospira, Inc, Lake forest IL, USA) and Heparin Sodium Injection, USP (APP Pharmaceuticals, LLC, Schaumburg, IL, USA) were used. Endothelin-1 Enzyme Immunometric Assay Kit (Catalog No. 900-020A, Assay Designs, Inc., Ann Arbor, MI, USA), IL-6 ELISA kit (Catalog No. KRC0061, Invitrogen Corporation, Carlsbad, CA), IL-10 ELISA kit (Catalog No. KRC0101, Invitrogen Corporation, Carlsbad, CA) and TNFα ELISA kit (Catalog No. ER3TNFA, Thermo Scientific, Rockford, IL) were used for various estimations.

Determination of cardiovascular response. The animals were anesthetized with urethane dissolved in isotonic saline. Urethane was administered in a dose of 1.5 g per kg body weight via intraperitoneal injection. Urethane was selected as an anesthetic agent, because it produces long lasting (8-10 hours) anesthesia with minimal cardiovascular and respiratory system depression. It produces a level of surgical anesthesia characterized by preservation of cardiovascular reflexes (Maggi and Meli 1986). Briefly, anaesthetized rats were immobilized on a surgical board equipped with controlled heating pad. Blood $PO_2$, $Pco_2$ and pH, were maintained using a tracheotomy cannula connected to a rodent ventilator (Model 683, Harvard Apparatus Inc., Holliston, MA). The right carotid artery was exposed to measure the left ventricular performance. Surgical suture (Deknatel, Research Triangle Park, NC) was secured around the proximal end of the carotid artery and an ultra-miniature pressure-volume (P-V) catheter SPR-869 (Millar Instruments, Houston, TX) was inserted through a tiny incision made near the proximal end of the artery. The P-V terminal of the catheter was connected to MPVS-300 P-V unit through PEC-4D and CEC-4B cables and advanced into the left ventricle to obtain the P-V signals. The signals were continuously aquired ($1000\ S^{-1}$) using the MPVS-300 P-V unit (AD Instruments, Mountain View, CA, USA) and PowerLab 16/30 data acquisition system (AD Instruments). MAP and HR were measured by cannulating the left femoral artery with pressure catheter SPR-320 (Millar Instruments), connected to the ML221 bridge amplifier (AD Instruments) through AEC-10C connector and the signals were acquired ($1000\ S^{-1}$) using PowerLab 16/30 data acquisition system (Gulati et al. 2012; Pacher et al. 2008). The left femoral vein was cannulated using PE 50 tubing (Clay Adams, Parsipanny, NJ) and secured for resuscitation.

Determination of arterial blood gases and base deficit. Baseline arterial blood pH, $Po_2$, $Pco_2$, $Na^+$, $K^+$ and lactate were monitored prior to induction of shock, 30 minutes after induction of shock, and 30 and 60 minutes following vehicle or centhaquin resuscitation. Blood samples (0.15 ml) were drawn from the arterial cannula using blood gas sampling syringes (Innovative Medical Technologies, Inc. Leawood, K S) and analyzed using a pHOx Ultra analyzer (Nova Biomedical Corporation, Waltham, MA). The base deficit was calculated using the formula (Davis et al. 1998; Paladino et al. 2008):

$$SBD=0.9287\times[HCO_3^--24.4+14.83\times(pH-7.4)]$$

Induction of Hemorrhagic Shock. Hemorrhage was induced by withdrawing blood from the femoral artery at a rate of approximately 0.5 to 1 mL/min until a MAP of 35 mmHg was reached. This MAP was maintained for 30 min by further withdrawal of blood, if necessary. The hemorrhagic shock model used in the present study is a well-established rodent model of manageable pressure hemorrhage (Buehler et al. 2000; Gulati et al. 1997a; Gulati and Sen 1998). The volume of blood loss was about approximately 8.0 ml in each rat and was similar in various groups, amounting to approximately 40% of the total blood. Measured hematocrit levels were similar in various groups. The duration of blood withdrawal was approximately 15 minutes.

Experimental design. To determine the resuscitative effect of centhaquin on cardiovascular system and plasma cytokines in hemorrhagic shock, rats were randomly divided into five groups, Group 1: Sham control (Non-hemorrhaged) (n=5), Group 2: Hemorrhage with no resuscitation (n=5); Group 3: Hemorrhage followed by resuscitation with 3% hypertonic saline (vehicle) (n=5); Group 4: Hemorrhage followed by resuscitation with vehicle plus centhaquin (0.017 mg/kg) (n=5); and Group 5: Hemorrhage followed by resuscitation with vehicle plus centhaquin (0.05 mg/kg) (n=5). Resuscitation was started 30 min after induction of hemorrhagic shock as an intravenous infusion (1 mL/min) through femoral vein using an infusion pump (Harvard Apparatus Infusion/Withdrawal Pump, Millis, MA). The blood samples, for biochemical estimations, were collected at 30 minutes of resuscitation and cardiovascular parameters were monitored till 60 minutes after which the animal was sacrificed. The volume of resuscitative solution was kept equal to the volume of blood loss. Although, this does not represent a typical human resuscitation, but this volume was selected to minimize confounding factors and allow a more accurate determination of resuscitative effect of centhaquin.

Determination of ET-1 level in the blood plasma. In order to analyze the change in plasma ET-1 level after hemorrhage followed by centhaquin resuscitation, blood samples were collected from rats of various groups 30 minutes after resuscitation and were collected into chilled EDTA tubes (1 $mg\cdot ml^{-1}$ of blood) containing aprotinin (500 $KIU\cdot mL^{-1}$ of blood). The blood samples were centrifuged at 1,600×g for 15 minutes at 0° C. and plasma ET-1 level was estimated using enzyme immunoassay. Briefly, plasma samples and standards were added to wells coated with a monoclonal antibody specific for ET-1. The plate was then washed after 24 hours of incubation and horseradish peroxidase (HRP) labeled monoclonal antibody was then added. After 30 minutes incubation the plate was washed and a solution of 3,3',5,5' tetramethylbenzidine substrate was added which generates a blue color. Hydrochloric acid (1N) was added to stop the substrate reaction and the resulting yellow color was read at 450 nm using DTX 800 Multimode detector and the data was analyzed with Multimode Detection Software (Beckman Coulter, Inc., Harbor Boulevard, Fullerton, CA). The measured optical density is directly proportional to the concentration of ET-1 (Lavhale et al. 2010).

Estimation of $ET_A$ and $ET_B$ receptor expression. Expression of $ET_A$ and $ET_B$ receptors was determined using the western blotting technique (Briyal et al. 2015; Leonard and Gulati 2013) with some modifications. After completion of cardiovascular experiments animals were sacrificed and the organs (brain, heart, liver, lung, kidney and abdominal aorta) were immediately dissected out, flash frozen on dry ice, and stored at −80° C. for further analysis. The tissue was homogenized with 10×(w/v) RIPA lysis buffer (20 mM Tris-HCl pH 7.5, 120 mM NaCl, 1.0% TritonX-100, 1.0% sodium deoxycholate, 0.1% sodium dodecyl sulfate (SDS), 10% glycerol, 1 mM disodium ethylene diamine tetraacetic acid (EDTA), 1 mM ethylene glycol-bis(β-aminoethyl ether)-N,N,N',N'-tetraacetic acid tetrasodium salt (EGTA), phosphatase inhibitors and Complete Mini Protease inhibitor cocktail tablet (Roche Diagnostics, Indianapolis, IN). Proteins were isolated in solubilized form and concentrations were measured by Folin-Ciocalteu's phenol reagent (Lowry et al. 1951). Solubilized protein (60 µg) was denatured in Laemmli sample buffer (Bio-Rad Laboratories, Hercules, CA), resolved on 10% sodium dodecyl sulfate-polyacrylamide gel electrophoresis (SDS-PAGE) and then transferred onto the nitrocellulose membrane followed by blocking the membrane with SuperBlock® Blocking Buffer in tris-buffered saline (TBS) (ThermoFisher Scientific, Hanover Park, IL). The membranes were washed three times with 1×TBS-Tween (TBST) and incubated with rabbit polyclonal anti-$ET_A$ receptor (ab85163, Abcam, Cambridge, MA, 1:1000) or anti-$ET_B$ receptor (ab117529, Abcam, Cambridge, MA, 1:1000) or mouse monoclonal anti-β-actin (a1978, Sigma-Aldrich, St. Louis, MO) antibodies, followed by horseradish peroxidase (HRP)-conjugated secondary antibodies goat anti-rabbit (sc2004, Santa Cruz Biotechnology, Dallas, TX, 1:2000) or goat anti-mouse (ab98693, Abcam, Cambridge, MA, 1:10,000) and visualized by SuperSignal® West Pico Chemiluminescent Substrate (ThermoFisher Scientific, Hanover Park, IL) using the ChemiDoc™ MP Imaging System (Bio-Rad Laboratories, Hercules, CA) and then analyzed using ImageJ (NIH) software.

Determination of IL-6, IL-10 and TNF-α levels in the blood plasma. Plasma levels of IL-6, IL-10 and TNF-α were estimated using commercially available rat enzyme-linked immunosorbent assay kits: IL-6 (Invitrogen Corporation, with a lower detection limit of 5 pg/ml; highly specific for rat IL-6 with no cross-reactivity with other cytokines), IL-10 (Invitrogen Corporation, with a lower detection limit of 5 pg/ml; highly specific for rat IL-10 with no cross-reactivity with other cytokines) and TNF-α ELISA kit (Thermo Scientific, with a lower detection limit of 15 pg/ml; highly specific for rat TNF-α with no cross-reactivity with other cytokines) were used for various estimations. All assays were performed using plasma samples that have not been thawed previously according to the protocols provided by the manufacturers.

Statistical Analysis. A Power Analysis was conducted using GraphPad Instat-2.00. The power was set to 80% (beta=0.8) and the level of significance (alpha) used was 0.05. Power Analysis indicated that a sample size of 5 for cardiovascular and 4 for biochemical estimation per group was sufficient to achieve a power of 80%, when level of significance alpha=0.05. Data are presented as mean±S.E.M. The significance of differences was estimated by one-way analysis of variance followed by a post hoc test (Bonferroni's method). A P value of less than 0.05 was considered to be significant. The statistical analysis was processed with GraphPad Prism 7.00 (GraphPad, San Diego, CA, USA).

Results

Effect of centhaquin on arterial blood pH, $pO_2$, $pCO_2$, hematocrit, blood lactate and base-deficit of hemorrhaged rats. A significant reduction in blood pH was observed in rats following hemorrhage, which was further decreased following administration of hypertonic saline. Centhaquin administration (0.017 and 0.05 mg/kg) significantly prevented the reduction of pH in hemorrhaged rats. Hemorrhage produced a significant decrease in $pCO_2$ and increase in $pO_2$ which was not affected by resuscitation with hypertonic saline or centhaquin (Table 1).

There was no change in percent hematocrit in control rats throughout the experimental period, while hematocrit lowered significantly ($p < 0.001$) after hemorrhage. Hemorrhaged rats, when resuscitated with hypertonic saline or with 0.017 and 0.05 mg/kg doses of centhaquin showed no change in hematocrit after treatment.

There was no change in blood lactate levels in control rats throughout the experimental period, while lactate levels were significantly increased ($p < 0.001$) following hemorrhage. Hemorrhaged rats, when resuscitated with 0.017 and 0.05 mg/kg doses of centhaquin showed a significant decrease ($p < 0.001$) in blood lactate levels compared to the hypertonic saline group (Table 1). There was no change in base deficit of control rats during the experimental period. Base deficit significantly ($p < 0.001$) increased after induction of hemorrhage, which was not affected by resuscitation with hypertonic saline. Rats resuscitated with 0.017 and 0.05 mg/kg doses of centhaquin, on the other hand, showed a significant decrease ($p < 0.001$) in base deficit (−12.0±0.2 and −11.6±0.5, respectively) compared to hypertonic saline (−16.3±1.3) (Table 1). Hemorrhaged rats that were not resuscitated could not survive till 60 min and hence no data could be obtained at that time point.

TABLE 1

Effect of centhaquin on hematocrit, arterial blood pH, $pCO_2$, $pO_2$, lactate and base deficit levels in hemorrhaged rats.

| | Time | Sham Control | Hemorrhage (No resuscitation) | Hemorrhage (3% saline) | Hemorrhage (centhaquin; 0.017 mg/kg) | Hemorrhage (centhaquin; 0.05 mg/kg) |
|---|---|---|---|---|---|---|
| Hematocrit (%) | Baseline | 36.0 ± 2.4 | 38.3 ± 0.8 | 38.3 ± 0.8 | 36.8 ± 1.3 | 39.3 ± 1.6 |
| | H. Shock | 38.3 ± 0.8 | 24.7 ± 2.4* | 22.2 ± 1.5* | 24.8 ± 1.5* | 22.2 ± 0.7* |
| | 60 min | 36.5 ± 1.5 | | 19.5 ± 1.8 | 21.5 ± 1.8 | 21.3 ± 1.3 |
| pH | Baseline | 7.40 ± 0.01 | 7.36 ± 0.01 | 7.37 ± 0.01 | 7.38 ± 0.01 | 7.38 ± 0.01 |
| | H. Shock | 7.39 ± 0.01 | 7.22 ± 0.02* | 7.17 ± 0.03* | 7.23 ± 0.02* | 7.25 ± 0.03* |
| | 60 min | 7.38 ± 0.01 | | 7.13 ± 0.02 | 7.24 ± 0.02$^\Delta$ | 7.28 ± 0.01$^\Delta$ |
| $PCO_2$ (mmHg) | Baseline | 32.5 ± 2.1 | 33.6 ± 1.1 | 33.3 ± 1.2 | 33.8 ± 1.2 | 34.5 ± 2.1 |
| | H. Shock | 29.3 ± 2.1 | 15.8 ± 0.7* | 15.9 ± 1.1* | 15.9 ± 0.9* | 16.3 ± 1.5* |
| | 60 min | 30.8 ± 2.2 | | 27.8 ± 2.8$^\#$ | 26.0 ± 1.6$^\#$ | 27.3 ± 1.9$^\#$ |
| $pO_2$ (mmHg) | Baseline | 122.2 ± 4.3 | 125.9 ± 5.7 | 120.3 ± 1.2 | 125.5 ± 1.9 | 120.2 ± 1.2 |
| | H. Shock | 121.7 ± 3.9 | 142.6 ± 1.3* | 140.3 ± 5.6* | 145.6 ± 1.9* | 142.8 ± 1.8* |
| | 60 min | 112.3 ± 3.9 | | 128.3 ± 4.8 | 131.3 ± 5.4$^\#$ | 121.3 ± 4.6$^\#$ |

TABLE 1-continued

Effect of centhaquin on hematocrit, arterial blood pH,
pCO$_2$, pO$_2$, lactate and base deficit levels in hemorrhaged rats.

| | Time | Sham Control | Hemorrhage (No resuscitation) | Hemorrhage (3% saline) | Hemorrhage (centhaquin; 0.017 mg/kg) | Hemorrhage (centhaquin; 0.05 mg/kg) |
|---|---|---|---|---|---|---|
| Lactate | Baseline | 1.9 ± 0.2 | 1.8 ± 0.1 | 1.9 ± 0.1 | 1.5 ± 0.2 | 1.8 ± 0.1 |
| (mmol/L) | H. Shock | 1.7 ± 0.1 | 7.4 ± 0.2* | 7.3 ± 0.2* | 7.6 ± 0.3* | 7.4 ± 0.4* |
| | 60 min | 1.2 ± 0.1 | | 3.7 ± 0.2$^{\#}$ | 1.9 ± 0.1$^{\#\Delta}$ | 1.7 ± 0.2$^{\#\Delta}$ |
| Base-deficit | Baseline | −2.7 ± 0.4 | −2.4 ± 0.3 | −2.4 ± 0.4 | −2.9 ± 0.3 | −2.8 ± 0.3 |
| (mEq/L) | H. Shock | −2.9 ± 0.5 | −15.7 ± 1.5* | −16.1 ± 0.6* | −15.3 ± 0.4* | −15.4 ± 0.9* |
| | 60 min | −3.9 ± 0.4 | | −16.3 ± 1.3 | −12.0 ± 0.2$^{\#\Delta}$ | −11.6 ± 0.5$^{\#\Delta}$ |
| ET-1 | 60 min | 13.6 ± 0.9 | 21.8 ± 0.9* | 25.3 ± 1.35* | 37.9 ± 3.0*$^{\#\Delta}$ | 38.3 ± 2.7*$^{\#\Delta}$ |

The values are expressed as mean ± S.E.M.
*p < 0.05 compared to baseline;
$^{\#}$p < 0.05 compared to hemorrhage;
$^{\Delta}$p < 0.05 compared to vehicle treated group.

Effect of centhaquin on mean arterial pressure and heart rate of hemorrhaged rats. Control rats did not show any change in MAP during the experimental period. MAP significantly decreased (p<0.001) in all the treatment groups after induction of hemorrhage. Hemorrhaged rats, resuscitated with hypertonic saline, did not show any improvement in MAP at either 30 or 60 minutes post resuscitation. Rats resuscitated with centhaquin (0.017 and 0.05 mg/kg) showed a significant increase (p<0.01) in MAP for at least 60 min post resuscitation (FIG. 1). Prior to hemorrhage, the baseline HR was approximately 345 beats/min in all groups. Hemorrhage produced a slight increase in HR (approximately 372 beats/min). In rats resuscitated with hypertonic saline HR dropped to 353±11 beats/min at 60 minutes, while in rats resuscitated with centhaquin in the doses of 0.017 and 0.05 mg/kg HR was 361±10 and 363±10, respectively (FIG. 1). No significant difference was observed in HR following resuscitation with hypertonic saline or centhaquin.

Effect of centhaquin on cardiac output and systemic vascular resistance of hemorrhaged rats. CO significantly decreased following hemorrhage in all the groups. Hemorrhaged rats resuscitated with hypertonic saline and centhaquin both produced a significant increase in CO (FIG. 1). Centhaquin resuscitation significantly increased CO at 30 and 60 min post resuscitation as compared to hypertonic saline alone. SVR decreased from 148±5 to 77±3 dyne*sec/cm$^5$ following hemorrhage, and it further decreased at 30 and 60 minutes of resuscitation with both hypertonic saline or centhaquin treatments (FIG. 1).

Effect of centhaquin on plasma ET-1 level of hemorrhaged rats. The baseline plasma ET-1 levels were 13.6±0.87 pg·ml$^{-1}$. After hemorrhage, ET-1 levels were significantly increased to 21.8±0.87 pg·ml$^{-1}$ (p<0.001). In rats treated with hypertonic saline, ET-1 levels were 25.3±1.35 pg·ml$^{-1}$, with no significant change compared to the untreated hemorrhagic shock group. However, in rats treated with centhaquin (0.017 and 0.05 mg/kg), the ET-1 levels were significantly increased (37.9±3.03 and 38.3±2.7 pg·ml$^{-1}$, respectively) compared to hemorrhaged rats resuscitated with hypertonic saline.

Figure 2:
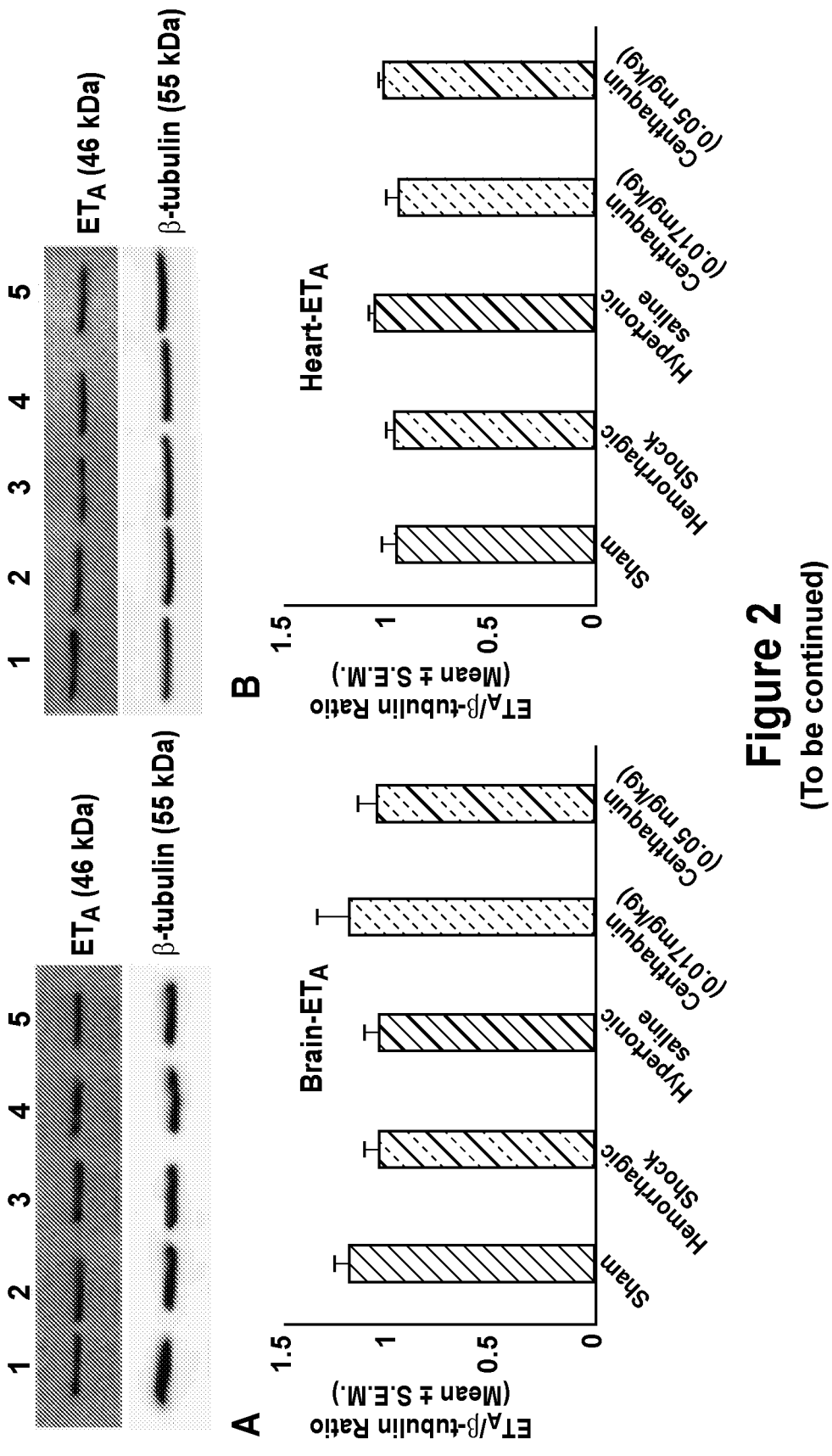
FIG. 2 depicts the effect of hemorrhage on the expression of $ET_A$ receptors in sham and hemorrhaged rats. Hemorrhaged rats were resuscitated with hypertonic saline or centhaquin. Lane 1—Sham; Lane 2—Hemorrhagic shock; Lane 3—Hypertonic saline (vehicle); Lane 4—Vehicle+centhaquin (0.017 mg/kg); Lane 5—Vehicle+centhaquin (0.05 mg/kg). The values are expressed as mean±S.E.M. (n=4). *p<0.05 compared to sham, #p<0.05 compared to hemorrhage or hypertonic saline.
Figure 2:
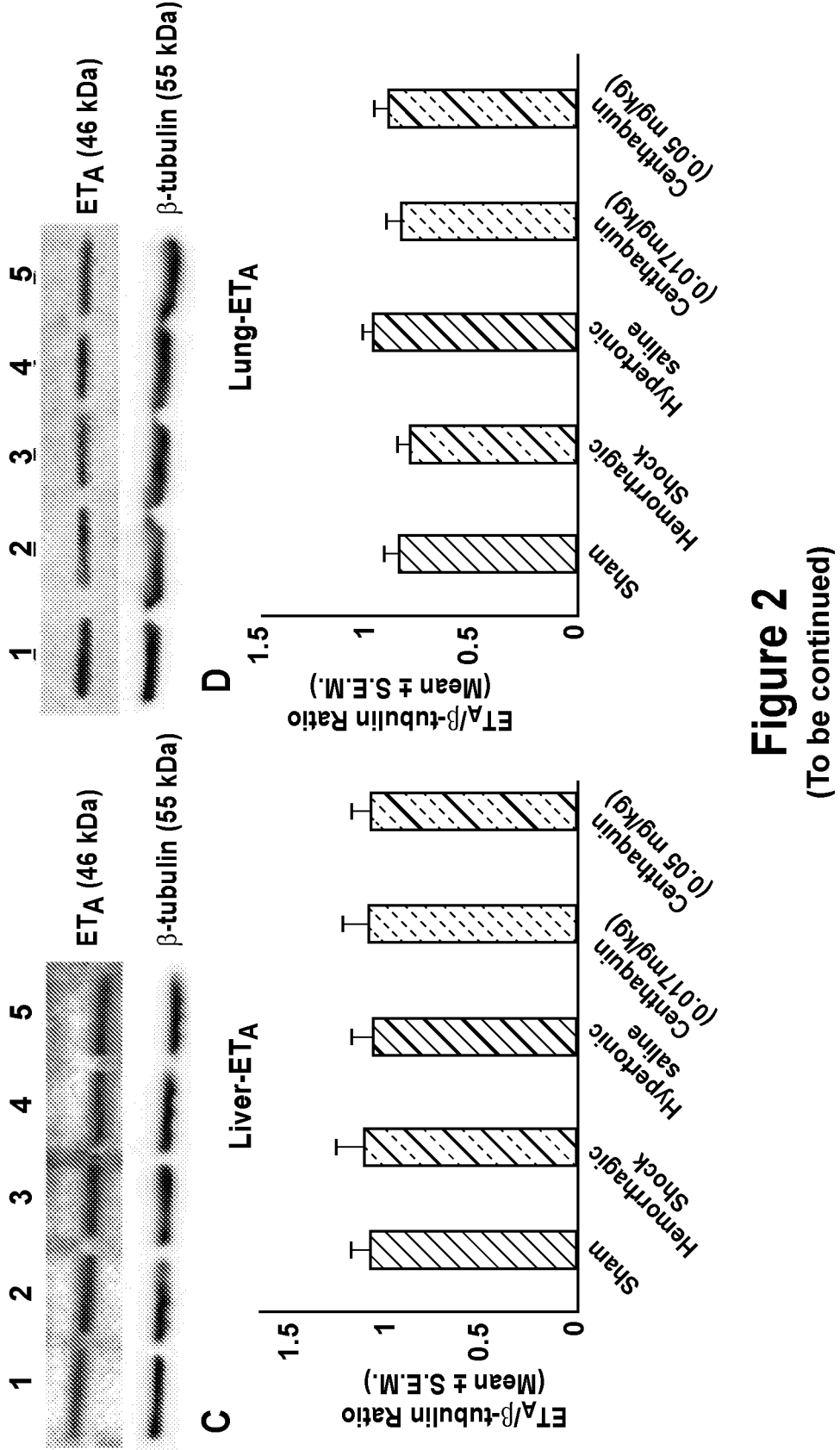
Figure 2:
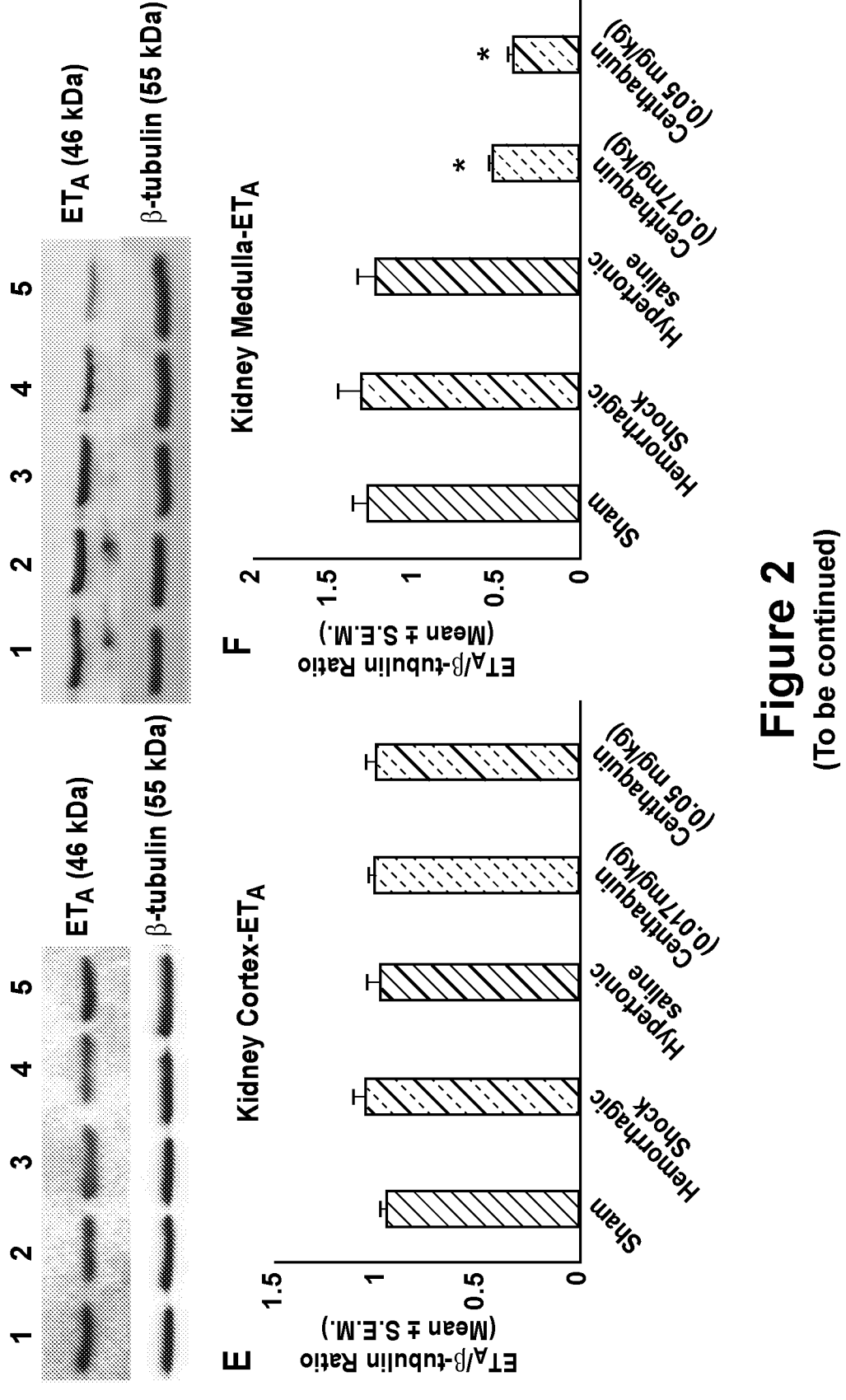
Figure 2:
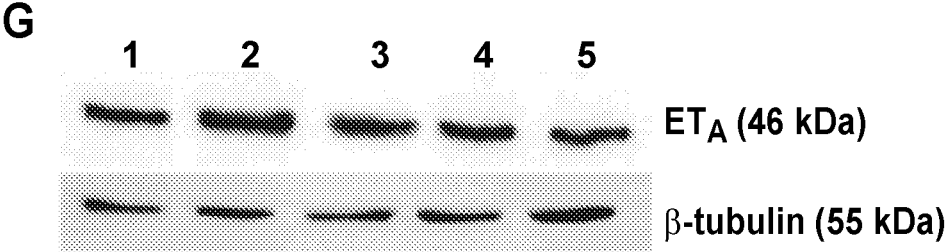
Figure 2:
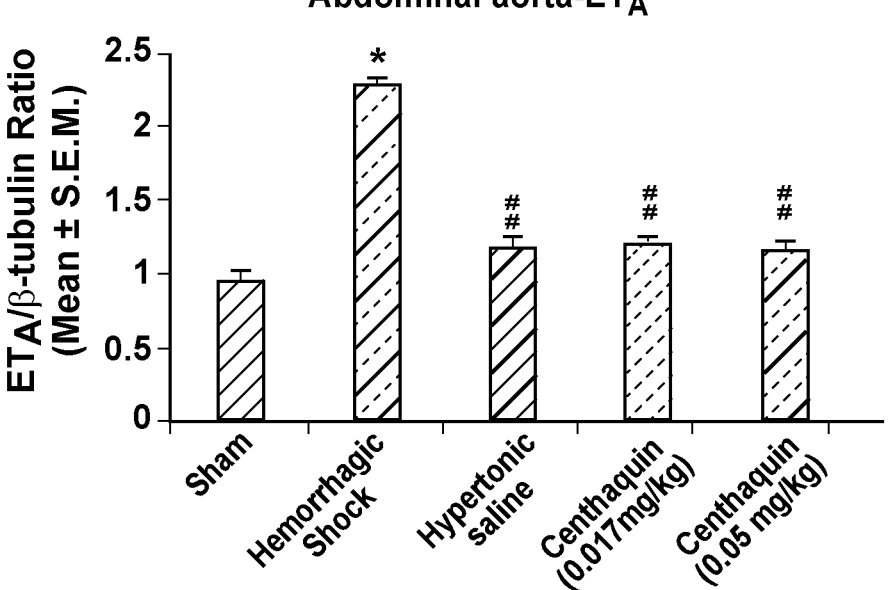

Effect of centhaquin on the expression of ET$_A$ receptors in hemorrhaged rats. There was no change in the expression of ET$_A$ receptors in the brain, heart, liver, lungs and kidney cortex (FIG. 2). A significant (p<0.0001) increase in the expression of ET$_A$ receptors was observed following hemorrhagic shock in the abdominal aorta. The expression of ET$_A$ receptors in the abdominal aorta of hemorrhaged rats increased by 140% compared to sham group. In hemorrhaged rats treated with hypertonic saline and hypertonic saline+centhaquin (0.017 and 0.05 mg/kg), a significant decrease (−48.8, −47.6 and −49.2%, respectively) in ET$_A$ expression was observed in the abdominal aorta compared to hemorrhaged rats with no treatment (FIG. 2). No change in ET$_A$ expression was observed in the renal medulla following hemorrhagic shock in rats. However, rats treated with centhaquin (0.017 and 0.05 mg/kg) presented with a significant decrease (−61.3% and −70.5%, respectively) in the expression of ET$_A$ receptors compared to hemorrhagic shock (FIG. 2).

Figure 3:
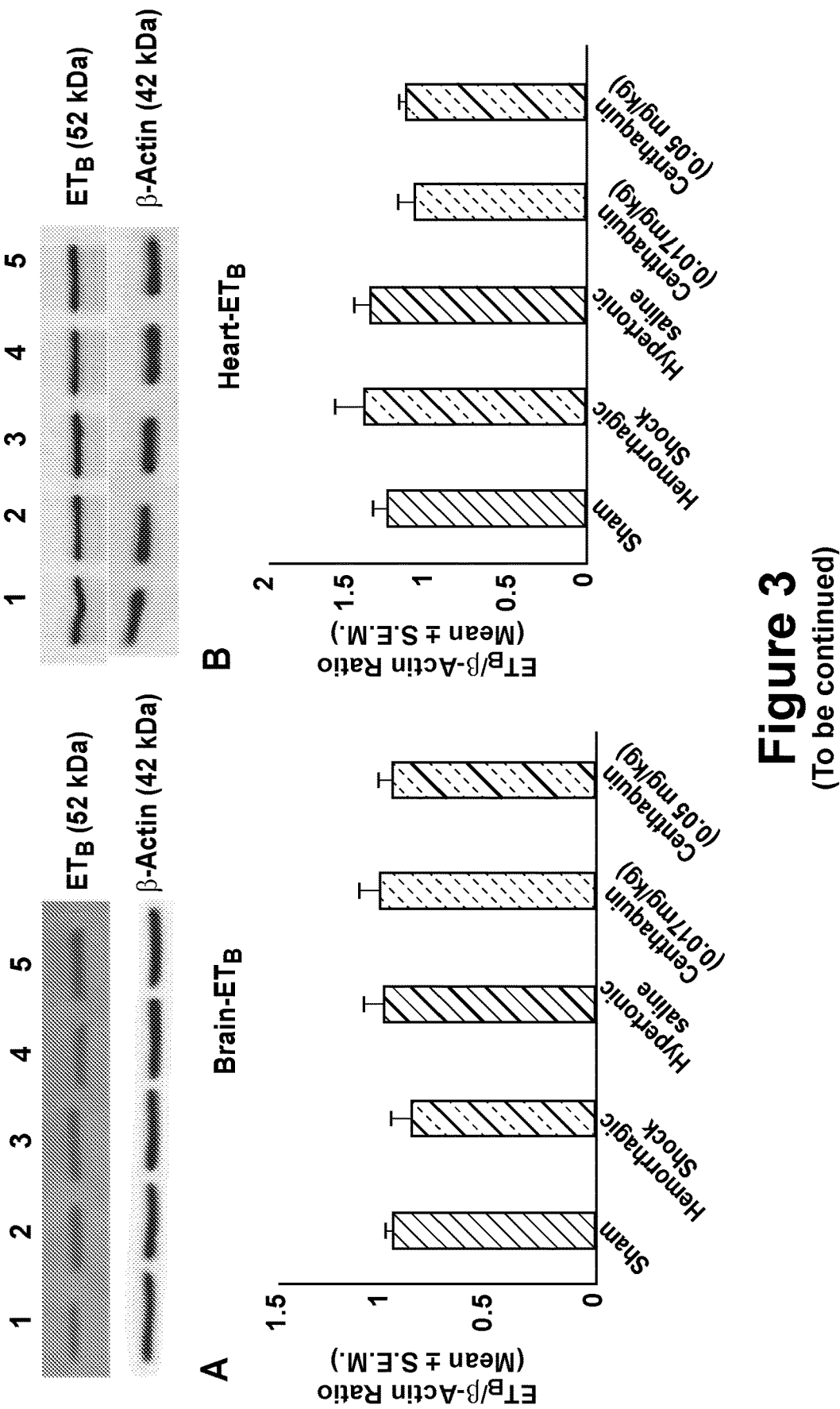
FIG. 3 shows the effect of hemorrhage on the expression of $ET_B$ receptors in sham and hemorrhaged rats. Hemorrhaged rats were resuscitated with hypertonic saline or centhaquin. Lane 1—Sham; Lane 2—Hemorrhagic shock; Lane 3—Hypertonic saline (vehicle); Lane 4—Vehicle+centhaquin (0.017 mg/kg); Lane 5—Vehicle+centhaquin (0.05 mg/kg). The values are expressed as mean±S.E.M. (n=4). *p<0.05 compared to sham, #p<0.05 compared to hemorrhage or hypertonic saline.
Figure 3:
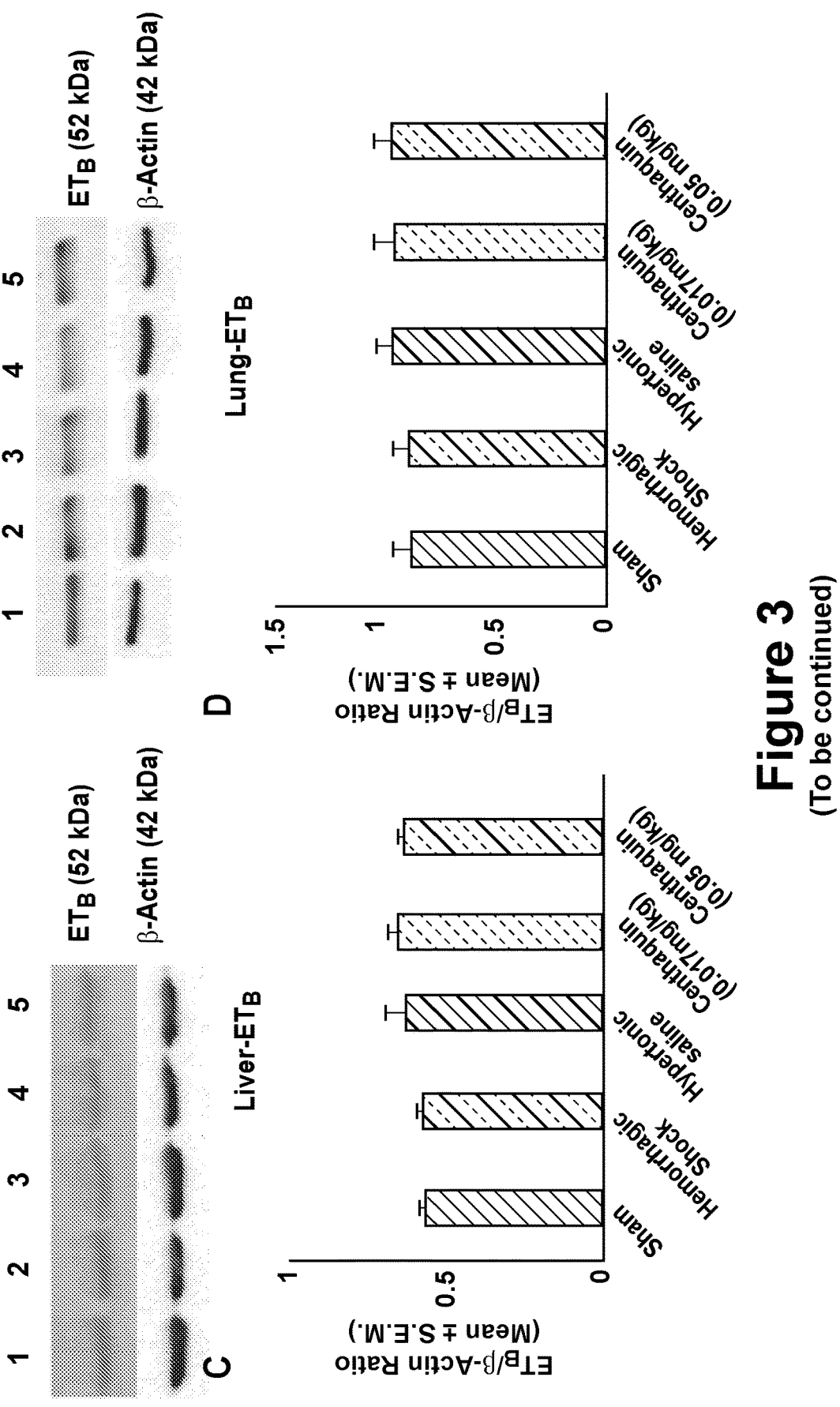
Figure 3:
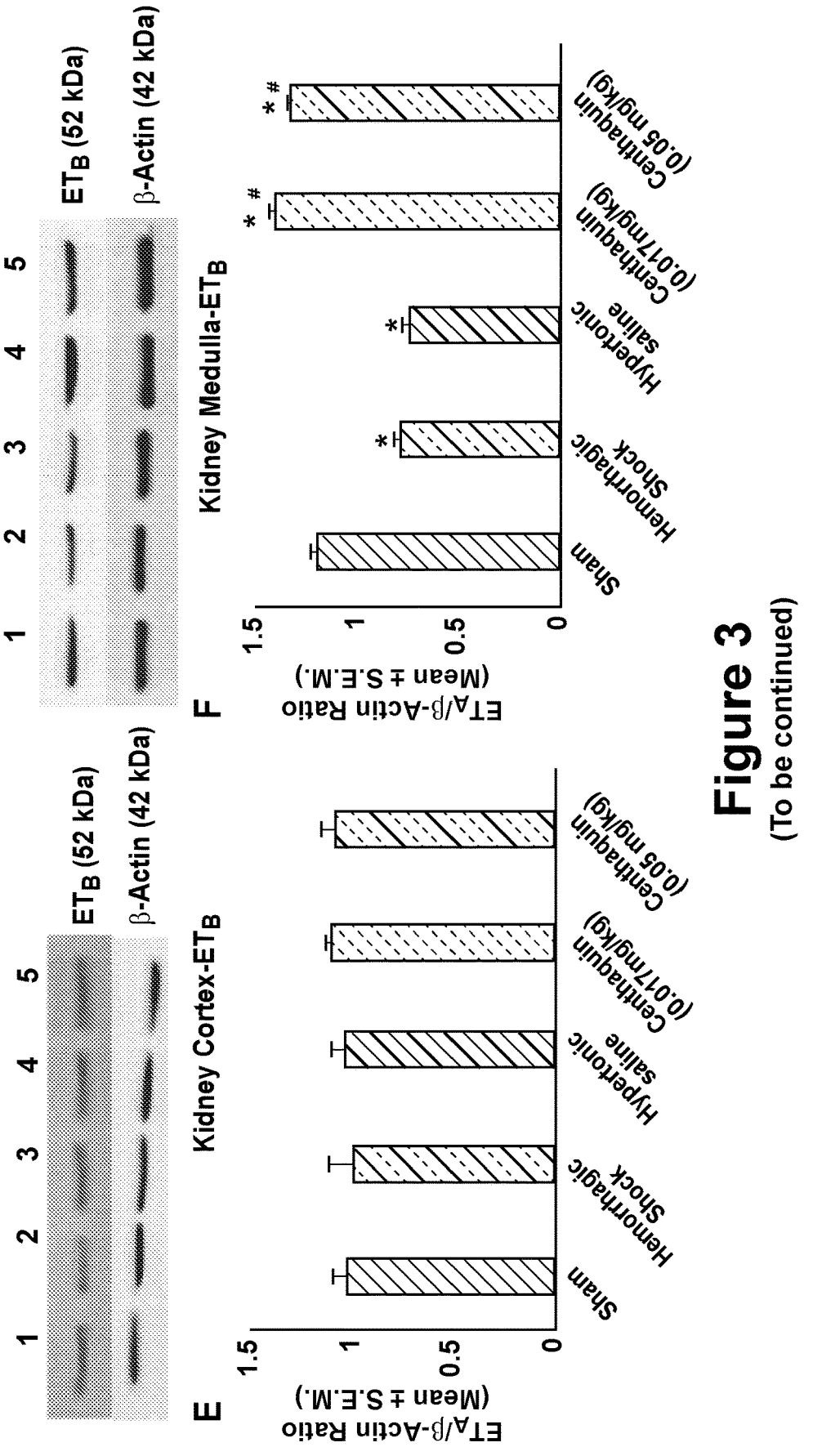
Figure 3:
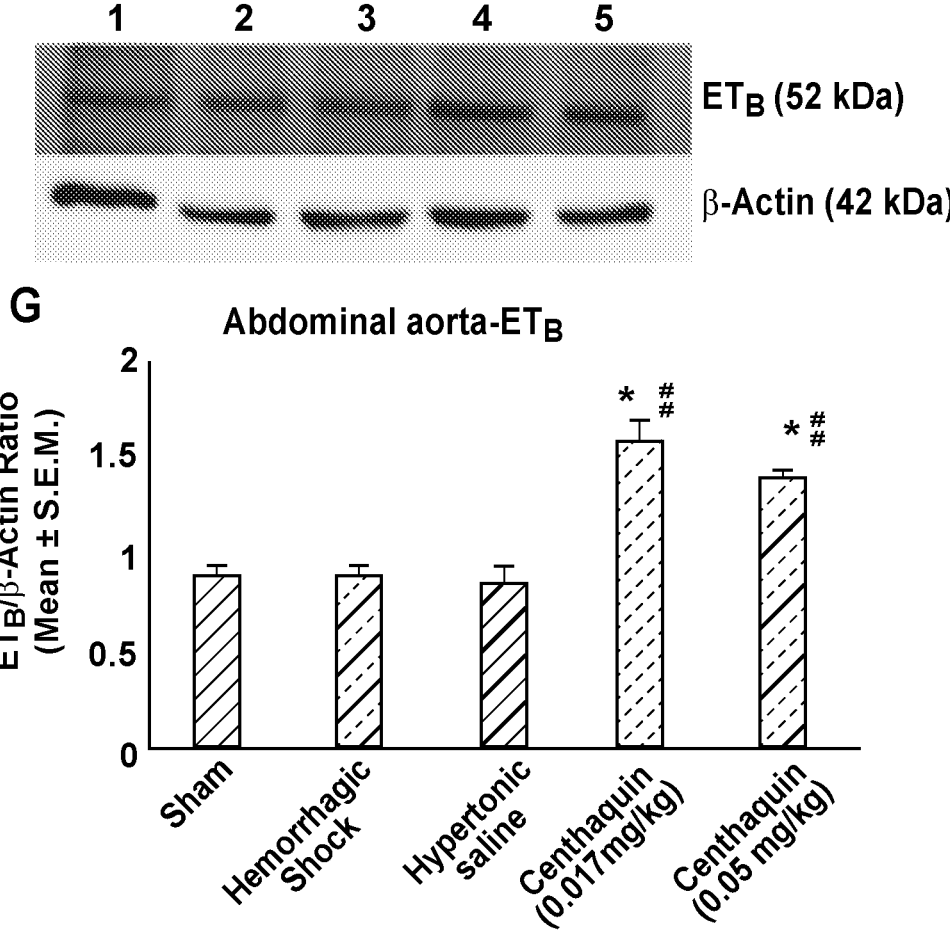

Effect of centhaquin on the expression of ET$_B$ receptors in hemorrhaged rats. There was no change in the expression of ET$_B$ receptors in brain, heart, liver, lungs and kidney cortex (FIG. 3). No change in ET$_B$ expression was observed in the abdominal aorta following hemorrhagic shock in rats. However, the expression of ET$_B$ receptors in abdominal aorta of rats treated with centhaquin (0.017 and 0.05 mg/kg) significantly increased (79.7% and 57.4%, respectively) compared untreated hemorrhaged rats (FIG. 3). A significant (p<0.0001) decrease (−34%) in the expression of ET$_B$ receptors was observed following hemorrhagic shock in kidney medulla compared to the sham group. In hemorrhaged rats treated with centhaquin (0.017 and 0.05 mg/kg), a significant increase (76.6% and 69.4%, respectively) in ET$_B$ expression was observed in the kidney medulla compared to untreated hemorrhaged rats (FIG. 3).

Figure 4:
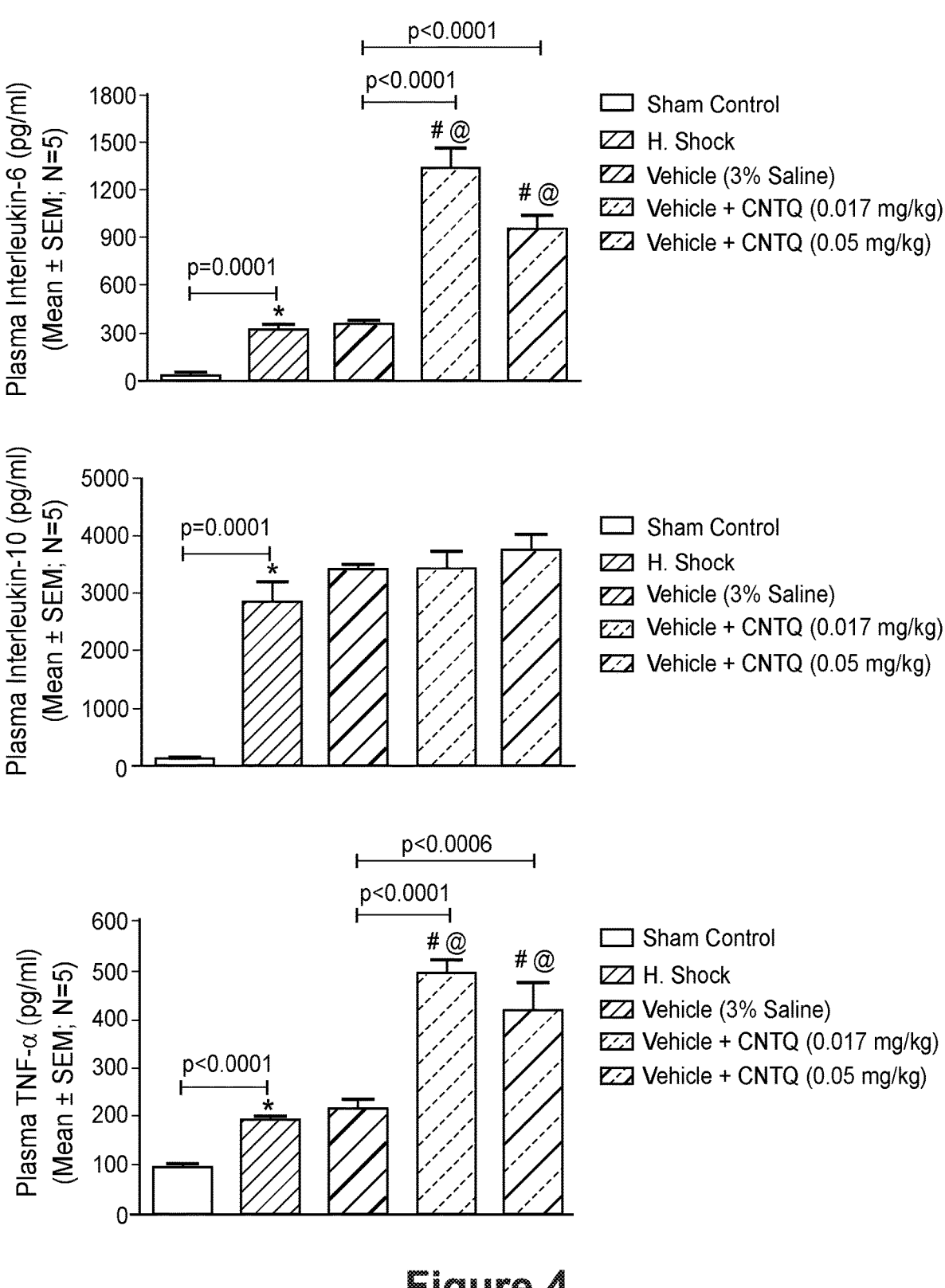
FIG. 4 shows the effect of hemorrhage on plasma TNF-α, IL-6 and IL-10 in sham and hemorrhaged rats. Hemorrhaged rats were resuscitated with hypertonic saline or centhaquin. The values are expressed as mean±S.E.M. (n=5). *p<0.05 compared to sham, #p<0.05 compared to hemorrhage, @p<0.05 compared to hypertonic saline.

Effect of centhaquin on plasma IL-6, IL-10 and TNF-α levels of hemorrhaged rats. To further evaluate whether centhaquin treatment affected the inflammatory response, we measured a select panel of cytokines in rat plasma. Overall, the levels of plasma IL-6, IL-10 and TNF-α were increased in all hemorrhaged rats with or without resuscitation with hypertonic saline and centhaquin. TNF-α and IL-6 levels were higher after hemorrhagic shock and resuscitation with hypertonic saline compared with sham control. Centhaquin further increased (p<0.01) the levels of TNF-α and IL-6 as compared to hypertonic saline alone. There was no statistically significant difference in plasma IL-10 between rats after hemorrhagic shock and resuscitation with hypertonic saline or centhaquin (FIG. 4).

Discussion

Centhaquin significantly decreased blood lactate and restored MAP and enhanced the resuscitative effect of hypertonic saline, confirming previous findings (Gulati et al. 2012; Gulati et al. 2013; Lavhale et al. 2013; Papapanagiotou et al. 2016). The effect of hemorrhagic shock and resuscitation using hypertonic saline alone or with centhaquin on $ET_A$ and $ET_B$ receptors expression in different tissues, plasma ET-1 levels and inflammatory markers were determined. It was found that $ET_A$ and $ET_B$ receptors in the abdominal aorta and renal medulla are involved in its resuscitative action. No change in $ET_A$ or $ET_B$ receptor levels were observed in the brain, heart, lung and liver following hemorrhagic shock or resuscitation with either hypertonic saline or centhaquin.

Vascular $ET_A$ receptors have been well established to have a strong vasoconstrictor effect (Schneider et al. 2007). Hemorrhage produced an increase in the expression of $ET_A$ receptors in the abdominal aorta. Resuscitation with hypertonic saline and centhaquin significantly reversed the hemorrhage-induced increase in $ET_A$ receptor expression in the abdominal aorta. However, $ET_B$ receptors were unaltered following hemorrhagic shock, but were increased by centhaquin treatment. It is possible that following hemorrhagic shock an increase in the expression of vasoconstrictor $ET_A$ receptors in the blood vessels occurs to maintain vascular tone and MAP. However, an increase in circulating ET-1 along with increased vascular $ET_A$ receptors may produce undesired vasoconstriction and reduce tissue perfusion.

On the other hand, an increase in plasma ET-1 levels following hemorrhagic shock has been reported to be acting as a compensatory mechanism to maintain blood pressure (Chang et al. 1993; Edwards et al. 1994; Gulati et al. 1997b; Sharma et al. 2002). It was also found that a precursor of ET-1 improved the resuscitative effect of hemoglobin based blood-substitute diaspirin cross-linked hemoglobin in severely hemorrhaged rats (Gulati et al. 1995). In normal rats ET-1 produces a biphasic response: an initial transient decrease followed by a sustained increase in blood pressure (Gardiner et al. 1994; Yanagisawa et al. 1988), however, in hemorrhaged rats, ET-1 produced a monophasic effect where only an increase in blood pressure was observed along with improved survival (Jochem et al. 2003). The resuscitative effect of ET-1 in hemorrhaged rats was mediated through $ET_A$ receptors since it was blocked by BQ123, a specific $ET_A$ receptor antagonist (Jochem et al. 2003). Without wishing to be bound by theory, vascular $ET_A$ receptors are increased following hemorrhagic shock as part of compensatory mechanism which is reversed upon resuscitation with either hypertonic saline or centhaquin. $ET_B$ receptors in the abdominal aorta were unaltered following hemorrhagic shock, but increased by centhaquin and not by hypertonic saline resuscitation. Since vascular $ET_B$ receptors produce vasodilation (Arai et al. 1990; Cardillo et al. 2000; Yanagisawa et al. 1988) therefore centhaquin induced increase in the expression of vascular $ET_B$ receptors may contribute towards an increase in tissue blood perfusion thereby decreasing blood lactate levels of hemorrhaged rats.

ET receptors crosstalk with each other and with adrenergic. The effect of $ET_B$ receptor desensitization is revealed in the presence of $ET_A$ receptor blockade (Mickley et al. 1997). On the other hand, $ET_B$ receptors are capable of altering the pharmacology of $ET_A$ receptors. It has been shown that venous $ET_A$ receptor blockade inhibited ET-1 induced contraction to a larger degree when $ET_B$ receptors were blocked (Thakali et al. 2008). Crosstalk between $ET_A$ and $ET_B$ receptors has been shown to take place in several different blood vessels in rodents (Lodge et al. 1995; Thakali et al. 2008) and all of these vessels possess contractile $ET_A$ and $ET_B$ receptors and suggest that pharmacological $ET_A$ and $ET_B$ receptor interaction require the presence of contractile $ET_B$ receptors (Thakali et al. 2008). It has been shown that $ET_A$ receptors modulate the cardiovascular responses of adrenergic agent such as clonidine (Gulati 1992; Gulati and Srimal 1993; Lavhale et al. 2013). Since centhaquin acts on adrenergic receptors, it is possible that changes in expression of $ET_A$ receptors is responsible for some of the resuscitative effects of centhaquin.

It is demonstrated herein that in the renal medulla, $ET_A$ receptor levels were unaltered following hemorrhagic shock, but were decreased by centhaquin, whereas $ET_B$ receptor expression decreased following hemorrhagic shock, which was completely attenuated by centhaquin and not with hypertonic saline. In the kidney, ET-1 produces vasoconstriction and decreases glomerular filtration rate which is mediated through $ET_A$ receptors (Harris et al. 1991; Kon et al. 1989). A decrease in the expression of $ET_A$ receptors induced by centhaquin could reduce the vasoconstrictor effect of ET-1 in the renal medulla. The outer renal medulla is the site where extensive reabsorption of sodium chloride takes place by the thick ascending limb of loop of Henle making outer renal medulla a site for high metabolic activity and demand for better blood perfusion (Cowley 2008). Hence this region is highly prone to hypoxic or ischemic injury following excessive hemorrhage. It is possible that centhaquin, by decreasing the concentration of $ET_A$ receptors, prevents the renal medullary region from ischemic injury following hemorrhagic shock. On the other hand, $ET_B$ receptor stimulation has been found to increase renal medullary blood flow mediated through vasodilators such as NO, cyclo-oxygenase and cytochrome p-450 metabolites (Hercule and Oyekan 2000; Vassileva et al. 2003). As shown herein, hemorrhagic shock decreased renal medullary $ET_B$ receptor expression which was not affected by resuscitation with saline but was attenuated by centhaquin. The results provided herein show that severe hemorrhage produces a decrease in the expression of $ET_B$ receptors in the renal medulla which may contribute towards a decrease in blood flow to the renal medulla causing ischemia and renal failure. Since resuscitation with centhaquin did not produce any decrease in renal medullary $ET_B$ receptor expression, it is possible that hemorrhage induced renal medullary ischemic effects could be attenuated by centhaquin. Therefore, centhaquin induced changes in $ET_A$ and $ET_B$ receptors both may be contributing to prevent the renal medulla from ischemic injury following hemorrhagic shock.

The renal medullary $ET_B$ receptors also play a role in the control of sodium and water excretion (Kohan et al. 2011; Schneider et al. 2007). $ET_B$ receptors in the epithelium of the renal medullary collecting ducts, are mainly responsible for inhibition of ET-1 action on sodium and water reabsorption (Kitamura et al. 1989; Kohan et al. 2011). The diuretic and natriuretic response to ET-1 was found to be attenuated by an $ET_B$ receptor antagonist (Hoffman et al. 2000). Patients with excessive blood loss presenting with anuria or oliguria warrant emergency medical attention because acute kidney failure is the main cause of death in such patients (Rossaint et al. 2006). It is possible that a decrease in the expression of renal medullary $ET_B$ receptors may contribute towards oliguria which could be attenuated by centhaquin. It may be speculated that centhaquin could be a novel pharmacological intervention to reduce renal injury mediated by hemorrhagic shock. These findings are preliminary and only suggestive, they need to be extensively investigated in animal studies. Studies are needed to investigate the effect of centhaquin on renal blood flow and whether those changes can be antagonized by specific $ET_A$ and $ET_B$ receptor antagonists.

In the present study it was found that hemorrhage increased the plasma concentration of ET-1, TNF-α, IL-6 and IL-10. Resuscitation with hypertonic saline did not alter plasma ET-1, TNF-$\alpha$, IL-6 or IL-10; however, centhaquin significantly increased plasma ET-1, TNF-$\alpha$ and IL-6 without affecting plasma IL-10 concentration. In a study conducted in mongrel dogs an increase in plasma ET-1 levels was observed following hemorrhage which co-related with the amount of blood loss (Chang et al. 1993). ET-1 increases superoxide anion production and cytokine secretion (Kowalczyk et al. 2015; Virdis and Schiffrin 2003), along with activation of transcription factors such as NF-$\kappa$B and expression of pro-inflammatory cytokines such as TNF-$\alpha$, IL-1, and IL-6. Cytokines, reciprocally, have been shown to modulate the secretion of ET-1 (Breuiller-Fouche et al. 2005; Yeager et al. 2012).

Hemorrhagic shock compromises the metabolic, cellular and inflammatory responses which can lead to multiple organ failure (Bonanno 2011; Gutierrez et al. 2004; Marik and Flemmer 2012). The response is typically characterized by release of pro-inflammatory cytokines such as IL-6 or TNF-$\alpha$ appearing immediately following hemorrhagic shock (Mees et al. 2009). This is followed by a sustained release of anti-inflammatory cytokines such as IL-10 which may contribute towards immune depression (Oberholzer et al. 2000). The overall impact of excessive IL-6 and TNF-$\alpha$ production in hemorrhage is still controversial. The present findings confirm increases in plasma levels of TNF-$\alpha$, IL-6 and IL-10 after hemorrhage. Resuscitation with hypertonic saline did not alter plasma TNF-$\alpha$, IL-6 or IL-10; however, centhaquin significantly increased plasma TNF-$\alpha$ and IL-6 without affecting plasma IL-10 concentration. Previous investigations have shown that an increased expression of $ET_B$ receptors may correlate with an increase in certain pro-inflammatory cytokines (Breuiller-Fouche et al. 2005; Pernow et al. 2000; White et al. 2000). It is demonstrated herein that centhaquin resuscitation increased $ET_B$ receptor expression in the abdominal aorta and renal medulla along with elevating plasma TNF-$\alpha$ and IL-6 concentration. Studies have suggested that a robust early TNF-$\alpha$ response is associated with survival in trauma victims and early elevation of plasma TNF-$\alpha$ serves either to limit organ damage or to induce reparative processes (Namas et al. 2009). Cytokine IL-6 seems to play a significant role in the systemic response to inflammation. Although several studies have shown beneficial effect of blockage of IL-6 in arthritis (Peake et al. 2006), multiple myeloma (Gado et al. 2000) and Crohn's disease (Atreya et al. 2000), inhibition of IL-6 has not been found to be beneficial in hemorrhagic shock (Mees et al. 2009). IL-6 plays a dual role in the inflammatory response to injury, often classified as pro-inflammatory locally and anti-inflammatory systemically. Studies have shown the beneficial effects of IL-6 deficiency in experimental paradigms of thermal injury, sepsis, and hemorrhage (Fontanilla et al. 2000; Mommsen et al. 2011; Yang et al. 2007). In contrast, other studies demonstrate that IL-6 administration prevents epithelial cell and cardio-myocyte apoptosis induced by hemorrhage (Alten et al. 2008; Moran et al. 2009). Systemic infusion of IL-6 following hemorrhagic shock reduces inflammation and injury in the liver and lung (Meng et al. 2000). Studies have also shown the beneficial effects of TNF-$\alpha$. Mice lacking TNF receptors have larger infarcts in ischemic brain injury (Bruce et al. 1996). TNF-$\alpha$ release in the hippocampus may promote neuroprotection and activate repair processes of the cerebral microvasculature as well as mediate neuronal plasticity (Kim et al. 2014; Sriram and O'Callaghan 2007). Several experimental studies suggest that both cytokines display protective actions in the brain (Bruce et al. 1996; Gadient et al. 1990; Hama et al.

1989; Kossmann et al. 1996). While centhaquin did increase IL-6 and TNF-$\alpha$ in the present study, more markers for inflammation are being examined in order to fully understand the influence of centhaquin on inflammation, both in normal and hemorrhaged animals, as these cytokines have the capacity to perform both pro- and anti-inflammatory functions.

Endothelin-1 (ET-1) acts on $ET_A$ and $ET_B$ receptors and has been implicated in hemorrhagic shock (shock). The effect of shock and resuscitation on $ET_A$ and $ET_B$ receptor expression was studied herein utilizing hypertonic saline (saline) or centhaquin. Rats were anesthetized, a pressure catheter was placed in the left femoral artery; blood was withdrawn from the right femoral artery to bring mean arterial pressure (MAP) to 35 mmHg for 30 minutes, resuscitation was performed and 90 minutes later sacrificed to collect samples for biochemical estimations. Resuscitation with centhaquin decreased blood lactate and increased MAP. Protein levels of $ET_A$ or $ET_B$ receptor were unaltered in the brain, heart, lung and liver following shock or resuscitation. In the abdominal aorta, shock produced an increase (140%) in $ET_A$ expression which was attenuated by saline and centhaquin; $ET_B$ expression was unaltered following shock but was increased (79%) by centhaquin. In renal medulla, $ET_A$ expression was unaltered following shock, but was decreased (−61%) by centhaquin; shock produced a decrease (−34%) in $ET_B$ expression which was completely attenuated by centhaquin and not saline. Shock induced changes in $ET_A$ and $ET_B$ receptors in the aorta and renal medulla are reversed by centhaquin and may be contributing to its efficacy.

In summary, centhaquin significantly improved resuscitation following hemorrhagic shock (HS) in rats. The administration of centhaquin following HS resulted in a decrease in the expression of vasoconstrictor $ET_A$ receptor and an increase in the expression of vasodilator $ET_B$ receptors, the mechanism for these alterations remains to be determined. Similarly, the significance of elevation in cytokines following hemorrhagic shock and resuscitation with centhaquin is contemplated that these changes improve tissue blood perfusion.

Centhaquin has been shown to have significant resuscitative effect following extensive hemorrhage in rat, rabbits and swine models. Hemorrhage decreases the expression of $ET_B$ receptors and it is contemplated that resuscitation with centhaquin attenuates this effect through the increased expression of $ET_B$ receptors. Specifically, centhaquin-induced increase in $ET_B$ receptor expression in the renal medulla could lead to a vasodilatory effect and promote diuresis and natriuresis, preventing injury to the renal medulla.

Example 2

The following example establishes that low doses of centhaquin (2-[2-[4-(3-methyphenyl)-1-piperazinyl)]ethyl-quinoline) citrate, significantly decreased blood lactate, and increased mean arterial pressure (MAP), pulse pressure (PP) and cardiac output (CO) in hemorrhagic shock (Gulati et al. 2012; Gulati et al. 2013; Lavhale et al. 2013; Papapanagiotou et al. 2016). Comparative studies were performed between centhaquin and status quo resuscitative agents grouped into 3 different categories: (a) fluids such as Lactated Ringer's, hypertonic saline; (b) adrenergic agents such as norepinephrine, and (c) fresh blood. Our results using (i) a rat model of fixed pressure blood loss, (ii) rabbit model of uncontrolled bleeding with trauma, and (iii) a pig model of massive blood loss indicate that centhaquin is highly effective in reducing the mortality following hypovolemic shock (Gulati et al. 2012; Gulati et al. 2013; Lavhale et al. 2013; Papapanagiotou et al. 2016). Unlike other resuscitative agents (vasopressors), centhaquin increased MAP by increasing stroke volume (SV) and CO; and decreased heart rate and systemic vascular resistance (SVR). Centhaquin is currently in clinical development as a resuscitative agent for hemorrhagic shock.

Hemorrhagic shock is a major cause of morbidity and mortality following trauma, particularly during the early stages of injury (Wu et al. 2009). Most of the deaths due to hemorrhagic shock occur in the first 6 hours after trauma (Shackford et al. 1993) and many of these deaths can be prevented (Acosta et al. 1998). Shock is accompanied by circulatory failure, which is mainly responsible for mortality and morbidity. The current recommended fluid therapy of using large volumes of lactated Ringer (LR) solution is effective in restoring hemodynamic parameters but presents logistic and physiological limitations (Vincenzi et al. 2009). Resuscitation with a large volume of crystalloids has been associated with secondary abdominal compartment syndrome, pulmonary edema, cardiac dysfunction, and paralytic ileus (Balogh et al. 2003). A secondary sequelae of circulatory failure in hemorrhagic shock is renal failure, which may be exacerbated by large volume fluid resuscitation. The incidence of acute kidney injury and renal failure following hemorrhagic shock is extremely high, with many requiring renal replacement therapy. The pathophysiology of renal failure in hemorrhagic shock is a result of splanchnic and renal vasoconstriction that directs blood flow to the heart and brain but may lead to ischemic injury of the kidney. Injury of tubular cells is most prominent in the straight portion of the proximal tubules and in the thick ascending limb of the loop of Henle, especially as it dips into the relatively hypoxic medulla. Changes in the proximal tubular cells are apical blebs and loss of the brush border membrane followed by a loss of polarity and integrity of the tight junctions. On a cellular level, ischemia causes depletion of adenosine triphosphate (ATP), an increase in cytosolic calcium, free radical formation, metabolism of membrane phospholipids, and abnormalities in cell volume regulation.

Methods

Animal Studies. Male Sprague-Dawley rats (340 to 380 g) (Envigo, Indianapolis, IN) were housed for at least 4 days in a room with controlled temperature (23±1° C.), humidity (50±10%) and light (6:00 A.M. to 6:00 P.M.) before being used. Food and water were made available continuously. Animal care and use for experimental procedures were approved by the Institutional Animal Care and Use Committee of the Midwestern University. All anesthetic and surgical procedures were in compliance with the guidelines established by the Animal Care Committee.

Drugs and Chemicals. Centhaquin citrate (PMZ-2010) was synthesized at Pharmazz India Private Limited, Greater Noida, India. Urethane (ethyl carbamate) (Sigma-Aldrich St Louis, MO, USA), Saline Injection, USP (Hospira, Inc, Lake forest IL, USA) and Heparin Sodium Injection, USP (APP Pharmaceuticals, LLC, Schaumburg, IL, USA) were used.

Determination of cardiovascular response. The animals were anesthetized with urethane dissolved in isotonic saline. Urethane was administered in a dose of 1.5 g per kg body weight via intraperitoneal injection. Urethane was selected as an anesthetic agent, because it produces long lasting (8-10 hours) anesthesia with minimal cardiovascular and respiratory system depression. It produces a level of surgical anesthesia characterized by preservation of cardiovascular reflexes (Maggi and Meli 1986). Briefly, anaesthetized rats were immobilized on a surgical board equipped with controlled heating pad. Blood $PO_2$, $Pco_2$ and pH, were maintained using a tracheotomy cannula connected to a rodent ventilator (Model 683, Harvard Apparatus Inc., Holliston, MA). MAP and HR were measured by cannulating the left femoral artery with pressure catheter SPR-320 (Millar Instruments), connected to the ML221 bridge amplifier (AD Instruments) through AEC-10C connector and the signals were acquired ($1000 S^{-1}$) using PowerLab 16/30 data acquisition system (Gulati et al. 2012; Pacher et al. 2008). A Perimed laser Doppler flow probe was placed in the renal medulla to measure blood perfusion and data was captured on PowerLab 16/30 data acquisition system. The left femoral vein was cannulated using PE 50 tubing (Clay Adams, Parsipanny, NJ) and secured for resuscitation.

Determination of arterial blood gases and base deficit. Baseline arterial blood pH, $PO_2$, $Pco_2$, $Na^+$, $K^+$ and lactate were monitored prior to induction of shock, 30 minutes after induction of shock, and 30 and 60 minutes following vehicle or centhaquin resuscitation. Blood samples (0.15 ml) were drawn from the arterial cannula using blood gas sampling syringes (Innovative Medical Technologies, Inc. Leawood, KS) and analyzed using a pHOx Ultra analyzer (Nova Biomedical Corporation, Waltham, MA). The base deficit was calculated using the formula (Davis et al. 1998; Paladino et al. 2008):

$$SBD=0.9287\times[HCO_3^--24.4+14.83\times(pH-7.4)]$$

Induction of Hemorrhagic Shock. Hemorrhage was induced by withdrawing blood from the femoral artery at a rate of approximately 0.5 to 1 mL/min until a MAP of 35 mmHg was reached. This MAP was maintained for 30 minutes by further withdrawal of blood, if necessary. The hemorrhagic shock model used in the present study is a well-established rodent model of manageable pressure hemorrhage (Buehler et al. 2000; Gulati et al. 1997; Gulati and Sen 1998). The volume of blood loss was about approximately 8.0 ml in each rat and was similar in various groups, amounting to approximately 40% of the total blood. Measured hematocrit levels were similar in various groups. The duration of blood withdrawal was approximately 15 minutes.

Experimental design. To determine the resuscitative effect of centhaquin on cardiovascular system in hemorrhagic shock, rats were randomly divided into three groups: Hemorrhaged rats were administered 100% shed blood volume of either normal saline (vehicle); 100% shed blood volume of either normal saline plus centhaquin (0.01 mg/kg) or 100% shed blood volume of either normal saline plus centhaquin (0.10 mg/kg) during the first 10 minutes of resuscitation. Additional experiments were also carried out where the amount of norepinephrine (a very commonly used vasopressor during resuscitation) required to maintain MAP at 70 mmHg in normal saline (NS) or centhaquin (0.01 mg/kg) treated rats (volume equal to blood loss) was determined.

Statistical Analysis. A Power Analysis was conducted using GraphPad Instat-2.00. The power was set to 80% (beta=0.8) and the level of significance (alpha) used was 0.05. Power Analysis indicated that a sample size of 5 for cardiovascular and 4 for biochemical estimation per group was sufficient to achieve a power of 80%, when level of significance alpha=0.05. Data are presented as mean±S.E.M. The significance of differences was estimated by one-way analysis of variance followed by a post hoc test (Bonferroni's method). A P value of less than 0.05 was considered to be significant. The statistical analysis was processed with GraphPad Prism 7.00 (GraphPad, San Diego, CA, USA).

Results

Effect of centhaquin on arterial blood pH, $pO_2$, $pCO_2$, hematocrit, blood lactate and base-deficit of hemorrhaged rats. A significant reduction in blood pH was observed in rats following hemorrhage, which was further decreased following administration of saline. Centhaquin administration (0.01 and 0.10 mg/kg) significantly prevented the reduction of pH in hemorrhaged rats. Hemorrhage produced a significant decrease in $pCO_2$ and increase in $pO_2$ which was not affected by resuscitation with saline or centhaquin.

There was no change in percent hematocrit in control rats throughout the experimental period, while hematocrit lowered significantly after hemorrhage. Hemorrhaged rats, when resuscitated with saline or with centhaquin showed no change in hematocrit after treatment.

There was no change in blood lactate levels in control rats throughout the experimental period, while lactate levels were significantly increased following hemorrhage. Hemorrhaged rats, when resuscitated with centhaquin showed a decrease in blood lactate levels compared to the saline group.

Effect of centhaquin on mean arterial pressure (MAP) of hemorrhaged rats. Control rats did not show any change in MAP during the experimental period. MAP significantly decreased in all the treatment groups after induction of hemorrhage. Hemorrhaged rats, resuscitated with saline, showed only transient improvement in MAP post resuscitation. Rats resuscitated with centhaquin (0.01 and 0.10 mg/kg) showed a significant increase (p<0.01) in MAP post resuscitation.

Effect of centhaquin on renal blood perfusion of hemorrhaged rats. Hemorrhaged rats were resuscitated with vehicle (saline) or centhaquin low dose (0.01 mg/kg) or high improving renal blood flow of hemorrhaged rats subjected to 20 minutes of renal artery occlusion.

Figure 7:
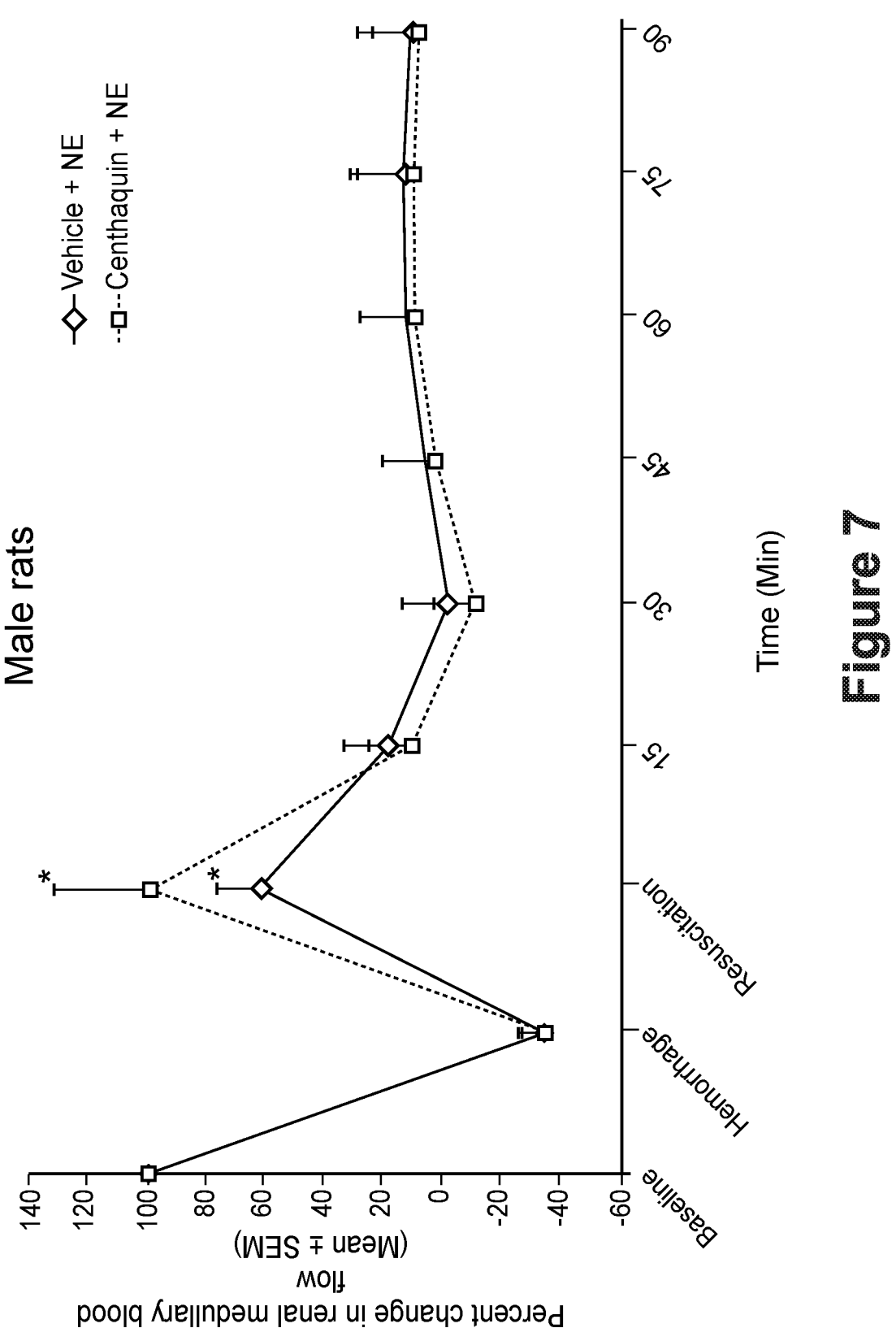
FIG. 7 shows results of experiments in which male rats were anaesthetized with urethane, the femoral vein was cannulated for drug administration, the femoral artery was cannulated for measuring mean arterial pressure (MAP), and a laser Doppler flow probe was placed in the renal medulla to measure blood perfusion. Induction of hemorrhagic shock was initiated by withdrawing blood to maintain the MAP at 35 mmHg for 30 minutes. Norepinephrine infusion was carried out to bring and maintain the MAP to 70 mmHg. The effect of centhaquin on cardiovascular functions were measured before the induction of shock, 30 minutes after shock (hemorrhage) and 15, 30, 45, 60, 75 and 90 minutes after resuscitation. Centhaquin improved renal blood perfusion of hemorrhaged male rats compared to vehicle control following resuscitation. The adverse effects of norepinephrine induced vasoconstriction can be attenuated by centhaquin.
Figure 8:
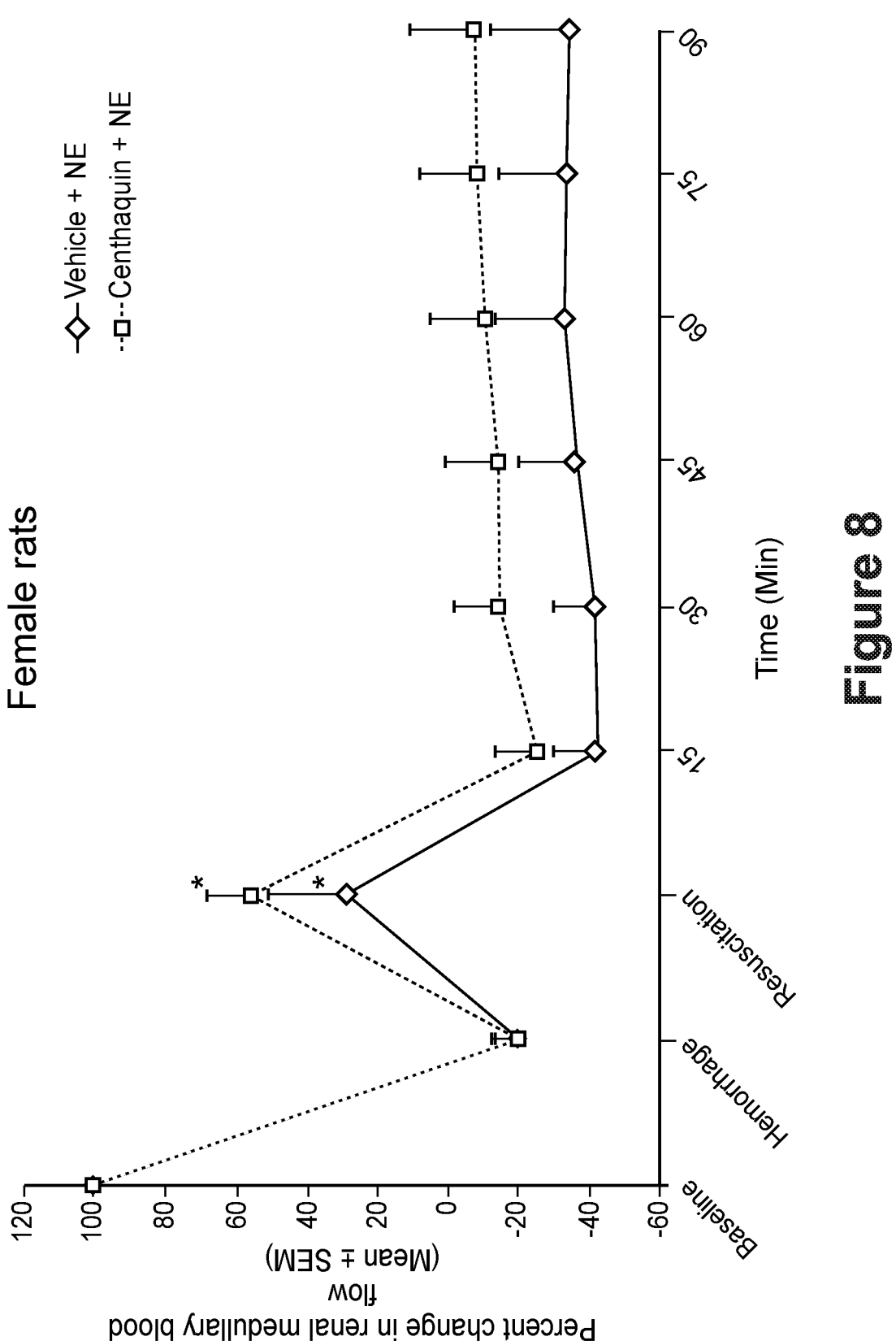
FIG. 8 shows results of experiments in which female rats were anaesthetized with urethane, the femoral vein was cannulated for drug administration, the femoral artery was cannulated for measuring mean arterial pressure (MAP), and a laser Doppler flow probe was placed in the renal medulla to measure blood perfusion. Induction of hemorrhagic shock was initiated by withdrawing blood to maintain the MAP at 35 mmHg for 30 minutes. Norepinephrine infusion was carried out to bring and maintain the MAP to 70 mmHg. The effect of centhaquin on cardiovascular functions were measured before the induction of shock, 30 minutes after shock (hemorrhage) and 15, 30, 45, 60, 75 and 90 minutes after resuscitation. Centhaquin improved renal blood perfusion of hemorrhaged female rats compared to vehicle control following resuscitation and an improved blood perfusion was observed till the end of experiment. The adverse effects of norepinephrine induced vasoconstriction can be attenuated by centhaquin.

Male rats were anaesthetized with urethane. The femoral vein was cannulated for drug administration, femoral artery was cannulated for measuring mean arterial pressure (MAP) and a laser Doppler flow probe was placed in the renal medulla to measure blood perfusion. Induction of hemorrhagic shock was initiated by withdrawing blood to maintain the MAP at 35 mmHg for 30 minutes. Norepinephrine infusion was carried out to bring and maintain the MAP to 70 mmHg. The effect of centhaquin on cardiovascular functions were measured before the induction of shock, 30 minutes after shock (hemorrhage) and 15, 30, 45, 60, 75 and 90 minutes after resuscitation. Centhaquin improved renal blood perfusion of hemorrhaged male rats compared to vehicle control following resuscitation. The adverse effects of norepinephrine induced vasoconstriction can be attenuated by centhaquin (FIG. 7). Similarly, centhaquin improved renal blood perfusion of hemorrhaged female rats compared to vehicle control following resuscitation and an improved blood perfusion was observed till the end of experiment (FIG. 8). The adverse effects of norepinephrine induced vasoconstriction can be attenuated by centhaquin.

Example 3

A prospective, multi-centric, randomized, double-blind, parallel, saline controlled phase II study of PMZ-2010 (centhaquin) as a resuscitative agent for hypovolemic shock due to excessive blood loss (CTRI/2017/03/008184) is being conducted. All subjects received standard treatment for shock (the type of treatment and care the enrolling institution would provide). Patients were randomly assigned to either control cohort (N=7) that received standard treatment along with normal saline or PMZ-2010 cohort (N=12) that received standard treatment along with PMZ-2010. Interim analysis showed comparable demographics of patients in both cohorts (Table 2).

TABLE 2

An interim analysis showing comparable demographics of patients in both cohorts of the phase II study.
Patient Demographics (Mean ± SEM)

Figure 5:
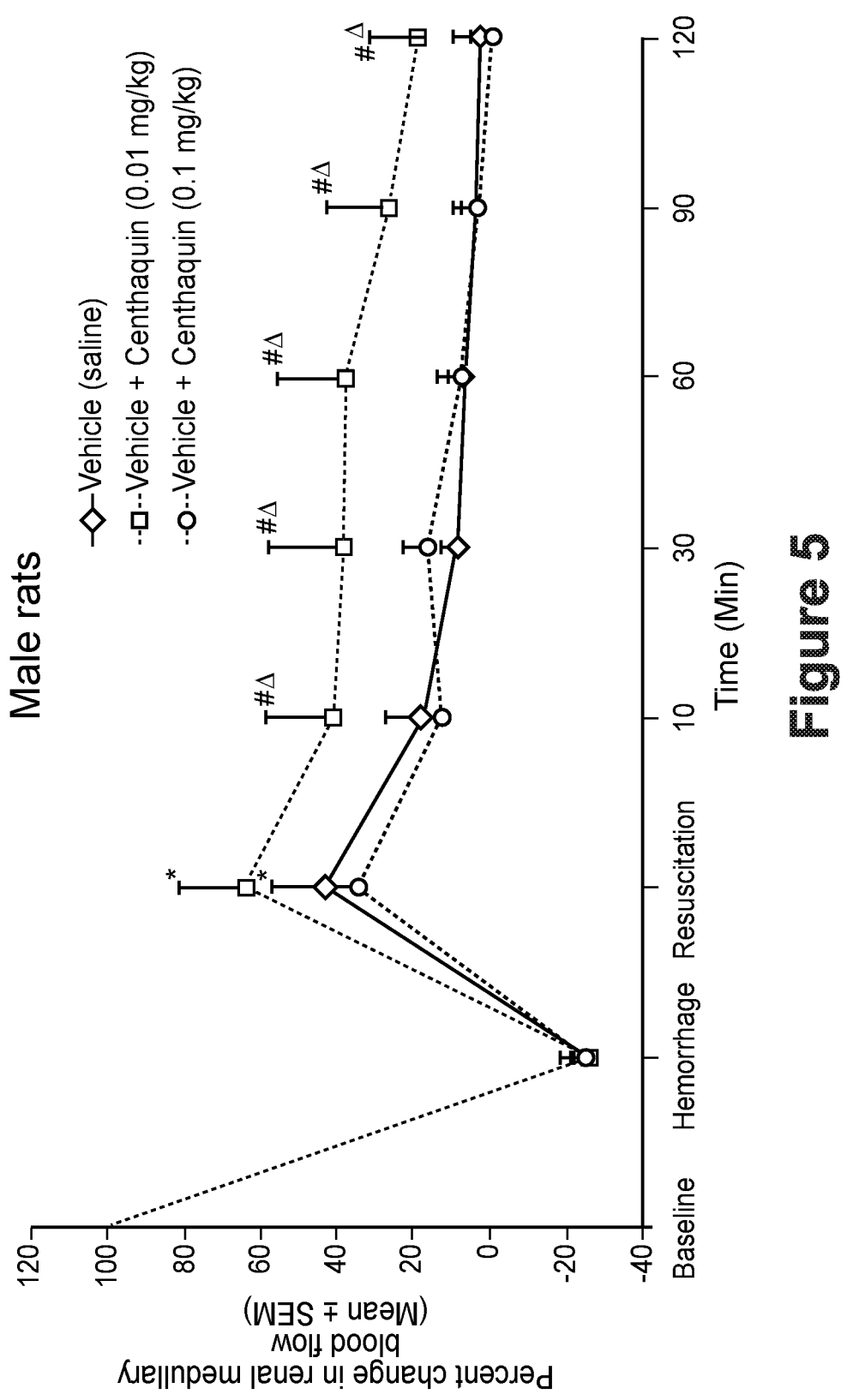
FIG. 5 shows the effect of hemorrhage on renal blood perfusion in male rats with massive blood loss. Hemorrhaged rats were resuscitated with vehicle (saline) or centhaquin low dose (0.01 mg/kg) or high dose (0.1 mg/kg). The values are expressed as mean±S.E.M. (n=5). *p<0.05 compared to hemorrhage, #p<0.05 compared to vehicle (saline).
Figure 6:
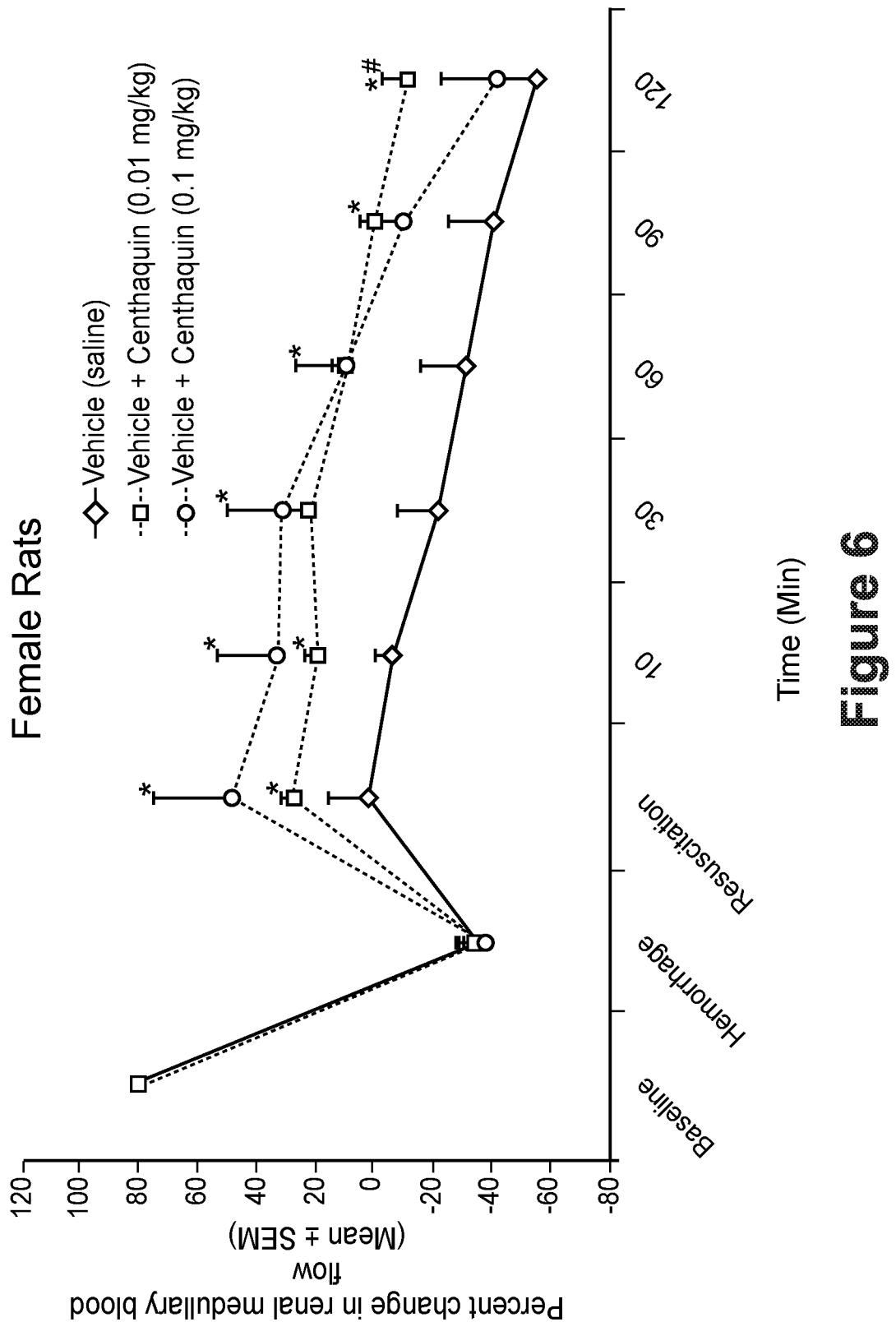
FIG. 6 shows the effect of hemorrhage on renal blood perfusion in female rats with massive blood loss. Hemorrhaged rats were resuscitated with vehicle (saline) or centhaquin low dose (0.01 mg/kg) or high dose (0.1 mg/kg). The values are expressed as mean±S.E.M. (n=5). *p<0.05 compared to hemorrhage, #p<0.05 compared to vehicle (saline).
Figure 9:
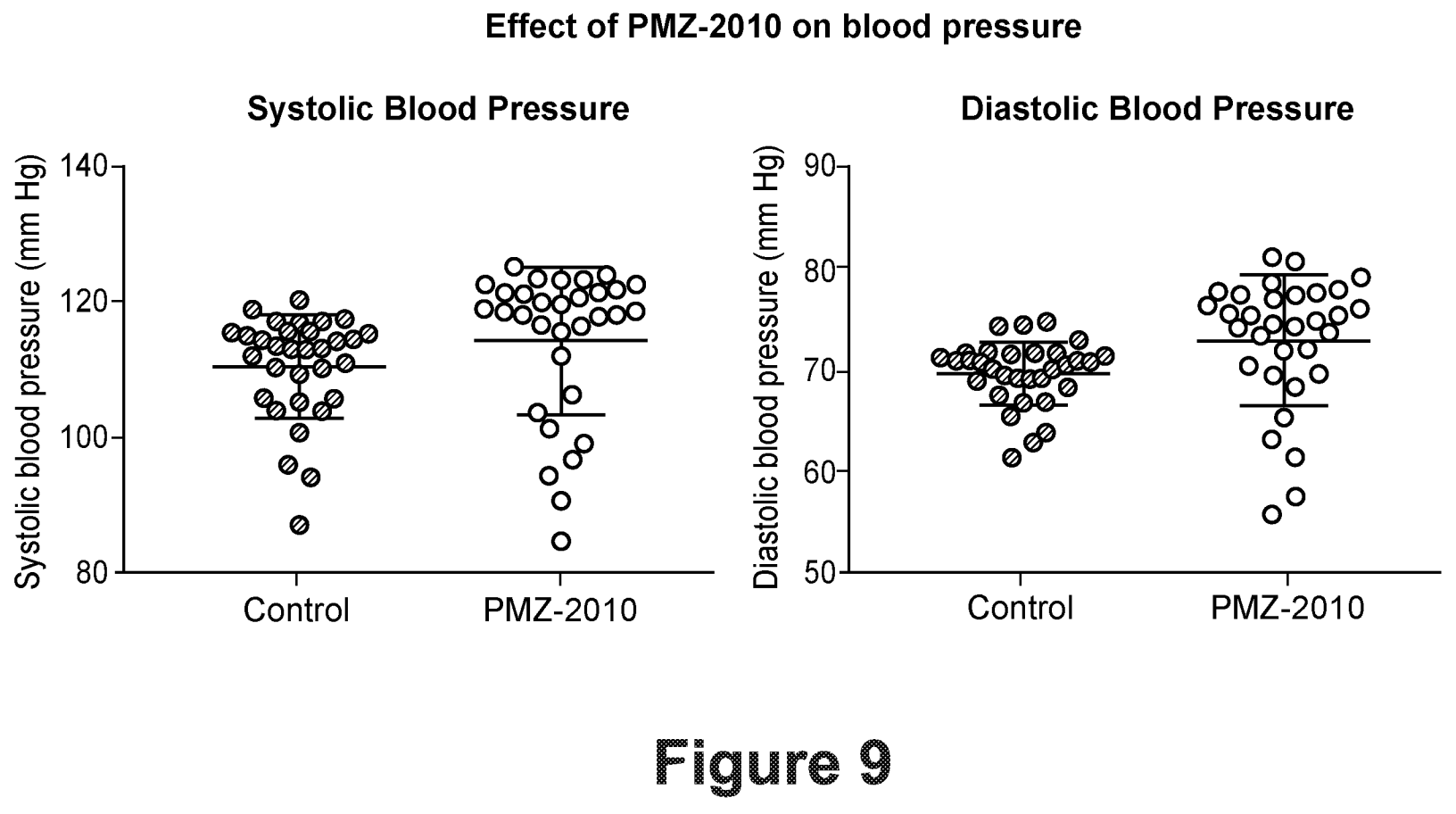

| Group | Gender | Age (Years) | Body Weight (Kg) | Height (Cm) | BMI (Kg/m2) | BSA (m2) |
|---|---|---|---|---|---|---|
| Normal Saline (N = 7) | (5M/2F) | 37.00 ± 6.41 | 64.29 ± 5.01 | 167.86 ± 2.24 | 22.96 ± 1.24 | 1.74 ± 0.07 |
| PMZ-2010 (N = 12) | (11M/1F) | 41.08 ± 3.59 | 65.42 ± 3.88 | 166.50 ± 2.57 | 23.46 ± 0.99 | 1.73 ± 0.06 | dose (0.1 mg/kg). The effect of centhaquin on renal blood perfusion was measured before the induction of shock, 30 minutes after shock (hemorrhage) and 10, 30, 60, 90 and 120 minutes after resuscitation. Low doses of centhaquin significantly improved renal blood perfusion of hemorrhaged male rats compared to equal volume of saline. This improved renal medullary blood perfusion is indicative of a use of centhaquin to prevent or treat injury to the kidneys (FIG. 5). Centhaquin significantly improved renal blood perfusion of hemorrhaged female rats compared to equal volume of saline (FIG. 6). A low dose of 0.02 mg/kg of centhaquin was also found to be effective in increasing the renal blood flow of hemorrhaged rats subjected to 20 minutes of renal artery occlusion. A ten times higher dose of 0.2 mg/kg centhaquin did not have the same efficacy in increasing renal blood flow as a low dose of 0.02 mg/kg centhaquin. Hence, a low dose (0.02 mg/kg) of centhaquin was more effective than a high dose (0.2 mg/kg) of centhaquin in The investigational drug PMZ-2010 met its primary endpoint of safety and no adverse event was reported. The number of doses required in PMZ-2010 treated were less than those required in control cohort (Table 3). Of the total hospital stay, PMZ-2010 treated patients spent only 39.3% time in intensive care unit compared to 57.3% of control. Time spent on ventilator was only 0.85±0.71 days in patients from PMZ-2010 group while it was 5.09±3.14 days in patients from control group. Total fluids needed in the first 48 hours of resuscitation was 19.9% less in PMZ-2010 treated patients; similarly, total blood products administered in the first 48 hours was 23.4% less in PMZ-2010 treated group compared to control. Systolic blood pressure increased by 34.5% from baseline (at the time of inclusion) until 48 hours after resuscitation in the control group while an increase of 45.2% was observed in PMZ-2010 treated group (FIG. 9). Similarly, diastolic blood pressure increased by 15.4% in the control group while 34.9% in PMZ-2010 treated group 48 hours after resuscitation (FIG. 9). Total amount of vasopressors needed in first 48 hours of resuscitation were 18.4±12.1 mg in the control group, while only 1.3±1.2 mg was needed in PMZ-2010 treated patients. Blood lactate levels decreased by 47% in control and 63% in PMZ-2010 treated patients. Interim analysis of a small number of patients indicated that PMZ-2010 improved numerous parameters that are indicative of its effectiveness as a resuscitative agent.

TABLE 3

Patients in the phase II study were randomly assigned to either control cohort that received standard treatment along with normal saline or PMZ-2010 cohort that received standard treatment along with PMZ-2010. An interim analysis as per approved protocol showed that number of doses required in PMZ-2010 treated were less than those required in control cohort. Although statistically not significant, there is a trend showing that resuscitation was more effective than standard treatment and required about 25% less doses. Number of Doses of Study Drug Administered in First 48 hours (Mean ± SEM)

| Group | Gender | Total Number of doses administered | Number of doses per patient |
|---|---|---|---|
| Normal Saline (N = 7) | (5M/2F) | 10 doses in 7 patients | 1.43 ± 0.43 |
| PMZ-2010 (N = 12) | (11M/1F) | 13 doses in 12 patients | 1.08 ± 0.08 |

Figure 10:
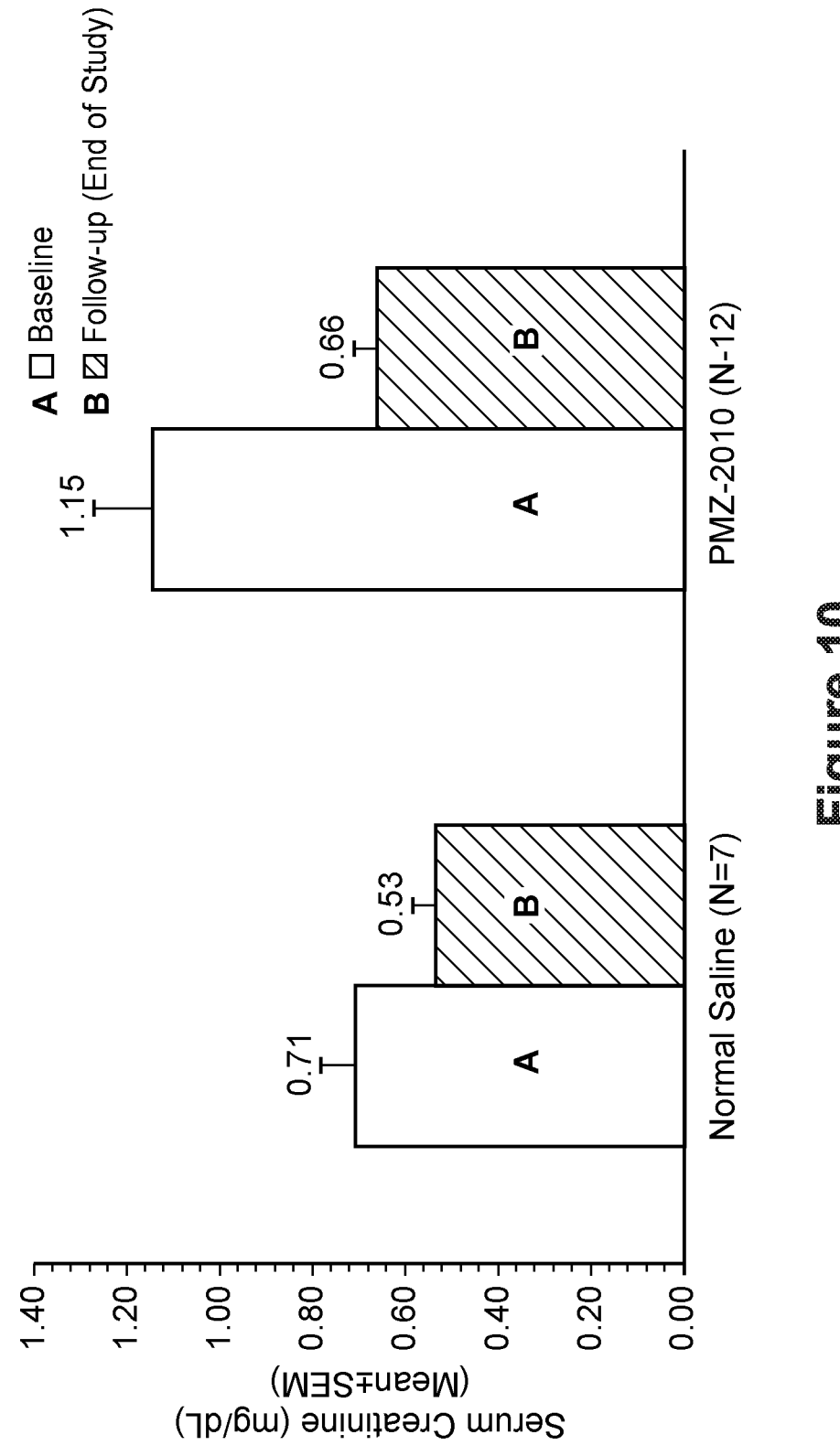
FIG. 10 shows results of the phase II study of centhaquin as a resuscitative agent for hypovolemic shock due to excessive blood loss in which all subjects received standard of care along with standard shock treatment. Patients were then randomly assigned to either control cohort that received standard treatment along with normal saline or centhaquin cohort that received standard treatment along with centhaquin. Serum creatinine levels were determined when the patient was inducted in the study (baseline) and at the time of discharge from hospital (end of the study). An interim analysis as per approved protocol showed that serum creatinine level decreased by 25.35% in control cohort and by 42.61% in centhaquin treated patients. The data indicated that reduction of serum creatinine levels by centhaquin is 17.26% more compared to standard treatment.

Serum creatinine levels were determined when the patient was inducted in the study (baseline) and at the time of discharge from hospital (end of the study). An interim analysis as per approved protocol showed that serum creatinine level decreased by 25.35% in control cohort and by 42.61% in PMZ-2010 treated patients. The data indicated that reduction of serum creatinine levels by PMZ-2010 is 17.26% more compared to standard treatment. See FIG. 10.

Figure 11:
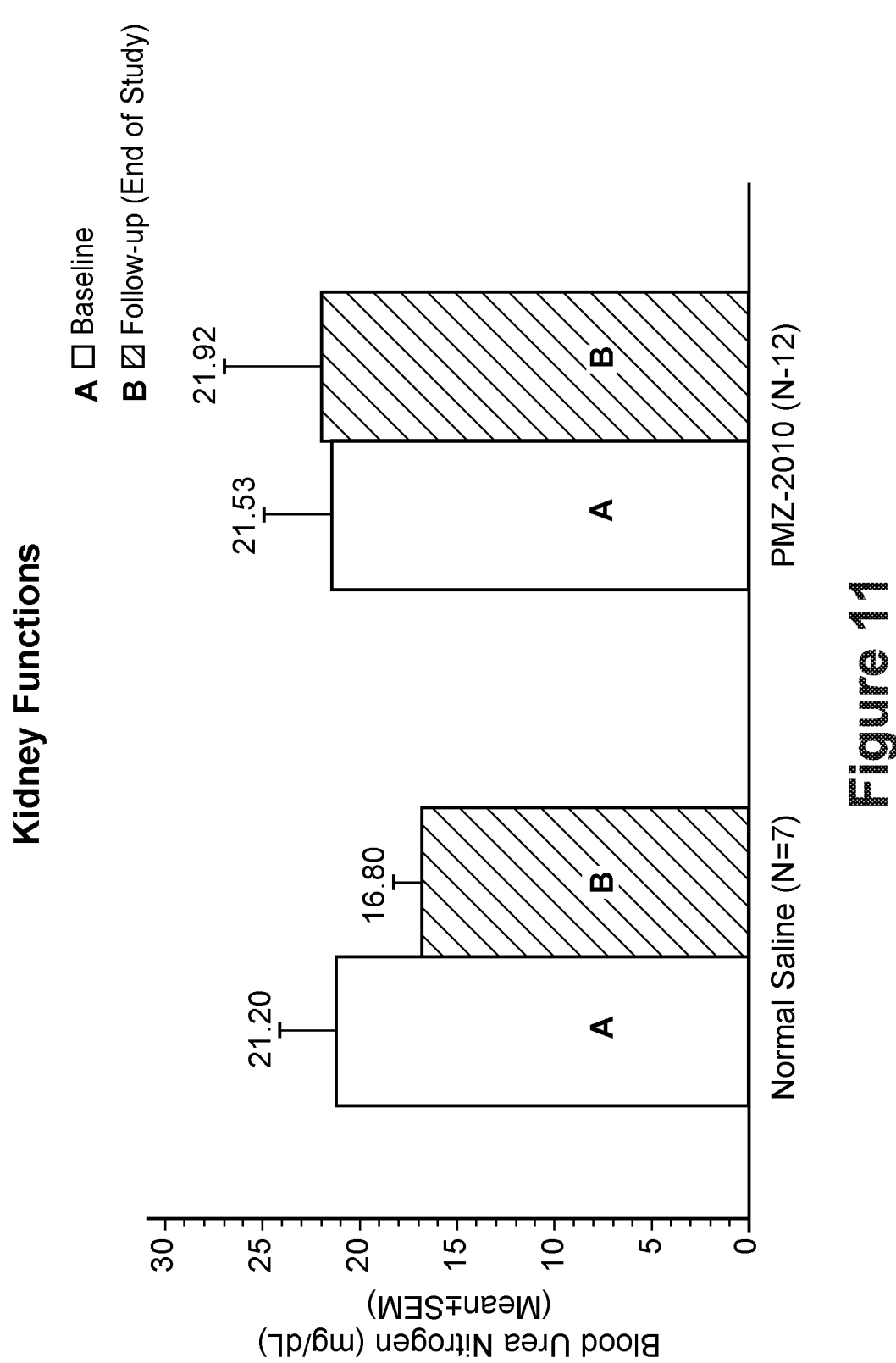
FIG. 11 shows results of the phase II study of centhaquin as a resuscitative agent for hypovolemic shock due to excessive blood loss in which all subjects received standard of care along with standard shock treatment. Patients were then randomly assigned to either control cohort that received standard treatment along with normal saline or centhaquin cohort that received standard treatment along with centhaquin. Blood urea nitrogen was determined when the patient was inducted in the study (baseline) and at the time of discharge from hospital (end of the study). An interim analysis as per approved protocol showed that blood urea nitrogen was similar in control cohort and centhaquin treated patients.

Blood urea nitrogen was determined when the patient was inducted in the study (baseline) and at the time of discharge from hospital (end of the study). An interim analysis as per approved protocol showed that blood urea nitrogen was similar in control cohort and PMZ-2010 treated patients. See FIG. 11.

Figure 12:
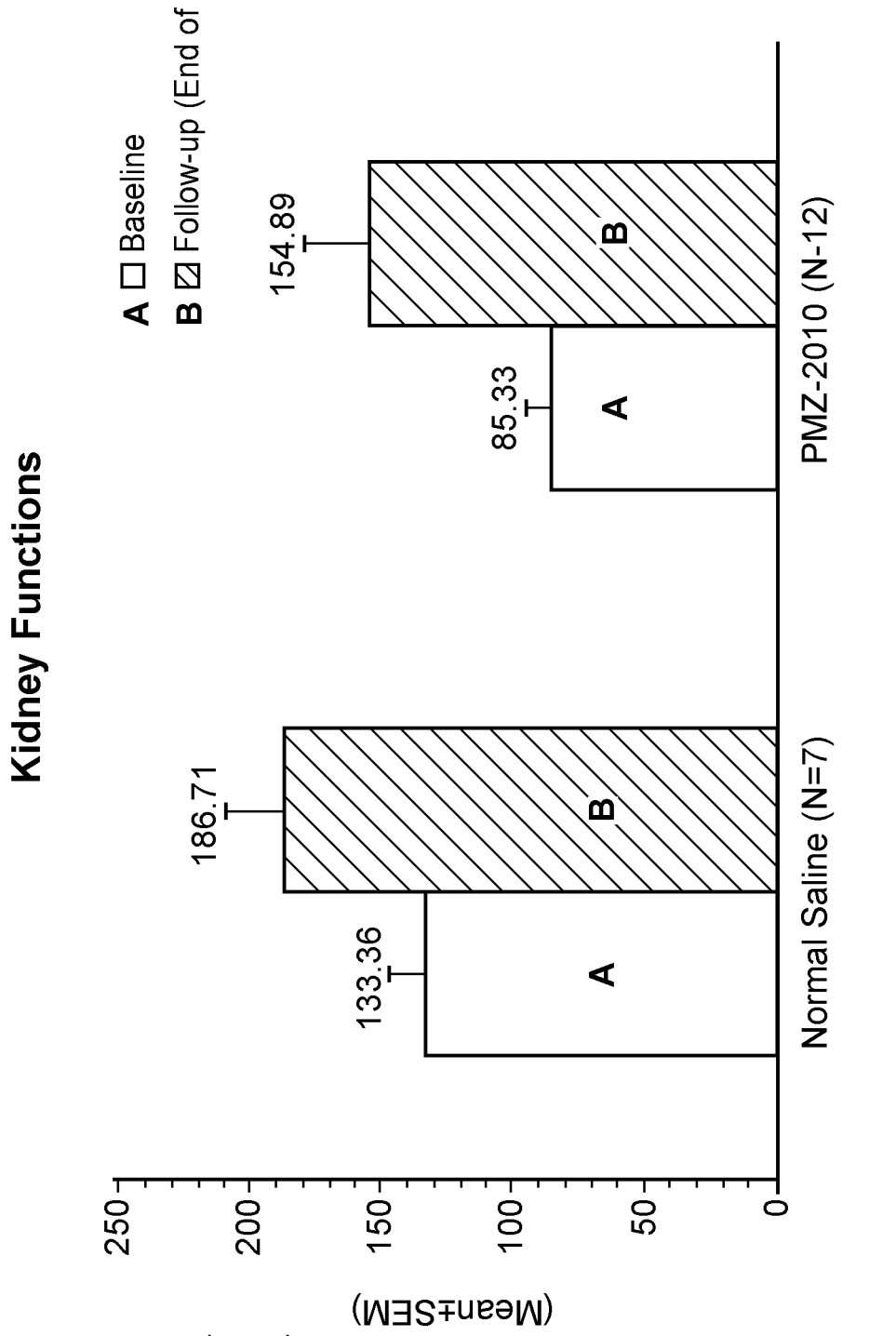
FIG. 12 shows results of the phase II study of centhaquin as a resuscitative agent for hypovolemic shock due to excessive blood loss in which all subjects received standard of care along with standard shock treatment. Patients were then randomly assigned to either control cohort that received standard treatment along with normal saline or centhaquin cohort that received standard treatment along with centhaquin. Glomerular filtration rate was determined when the patient was inducted in the study (baseline) and at the time of discharge from hospital (end of the study). An interim analysis as per approved protocol showed that glomerular filtration rate increased by 40.00% in control cohort and by 81.52% in centhaquin treated patients. The data indicated that an increase in glomerular filtration rate by centhaquin is 41.52% more compared to standard treatment.

Glomerular filtration rate was determined when the patient was inducted in the study (baseline) and at the time of discharge from hospital (end of the study). An interim analysis as per approved protocol showed that glomerular filtration rate increased by 40.00% in control cohort and by 81.52% in PMZ-2010 treated patients. The data indicated that an increase in glomerular filtration rate by PMZ-2010 is 41.52% more compared to standard treatment. See FIG. 12.

Discussion

The principal feature of acute renal failure is an abrupt decline in glomerular filtration rate (GFR), resulting in the retention of nitrogenous wastes (urea, creatinine). In the general world population 170-200 cases of severe acute renal failure per million population occur annually. To date, there is no specific treatment for acute renal failure. Several drugs have been found to ameliorate toxic and ischemic experimental acute renal failure, as manifested by lower serum creatinine levels, reduced histological damage and faster recovery of renal function in different animal models. These include anti-oxidants, calcium channel blockers, diuretics, vasoactive substances, growth factors, anti-inflammatory agents and more. However, those drugs that have been studied in clinical trials showed no benefit, and their use in acute renal failure has not been approved. The foregoing example demonstrates the use of centhaquin and its salts to prevent and/or treat patients with acute renal failure.

Centhaquin has been shown to have significant resuscitative effect following extensive hemorrhage in rat, rabbits and swine models. Centhaquin was found to be an effective resuscitative agent and induced an increase in blood flow to the renal medulla and decrease serum creatinine levels in patients with hypovolemic shock. In addition, centhaquin increased glomerular filtration rate in patients with hypovolemic shock. It is contemplated that centhaquin and its salts will lead to a vasodilator effect and promote diuresis and natriuresis, and improve renal functions by increasing the glomerular filtration rate and decrease serum creatinine levels.

REFERENCES

ACOSTA J A, YANG J C, WINCHELL R J, SIMONS R K, FORTLAGE D A, HOLLINGSWORTH-FRIDLUND P and HOYT D B: Lethal injuries and time to death in a level I trauma center. Journal of the American College of Surgeons 186: 528-533, 1998.

ALLGREN R L, MARBURY T C, RAHMAN S N, WEISBERG L S, FENVES A Z, LAFAYETTE R A, SWEET R M, GENTER F C, KURNIK B R, CONGER J D and SAYEGH M H: Anaritide in acute tubular necrosis. Auriculin Anaritide Acute Renal Failure Study Group. *N Engl J Med* 336: 828-834, 1997.

ALTEN J A, MORAN A, TSIMELZON A I, MASTRANGELO M A, HILSENBECK S G, POLI V and TWEARDY D J: Prevention of hypovolemic circulatory collapse by IL-6 activated Stat3. PloS one 3: e1605, 2008.

ARAI H, HORI S, ARAMORI I, OHKUBO H and NAKANISHI S: Cloning and expression of a cDNA encoding an endothelin receptor. Nature 348: 730-732, 1990.

ATREYA R, MUDTER J, FINOTTO S, MULLBERG J, JOSTOCK T, WIRTZ S, SCHUTZ M, BARTSCH B, HOLTMANN M, BECKER C, STRAND D, CZAJA J, SCHLAAK J F, LEHR H A, AUTSCHBACH F, SCHURMANN G, NISHIMOTO N, YOSHIZAKI K, ITO H, KISHIMOTO T, GALLE P R, ROSE-JOHN S and NEURATH M F: Blockade of interleukin 6 trans signaling suppresses T-cell resistance against apoptosis in chronic intestinal inflammation: evidence in crohn disease and experimental colitis in vivo. Nature medicine 6: 583-588, 2000.

BALOGH Z, MCKINLEY B A, HOLCOMB J B, MILLER C C, COCANOUR C S, KOZAR R A, VALDIVIA A, WARE D N and MOORE F A: Both primary and secondary abdominal compartment syndrome can be predicted early and are harbingers of multiple organ failure. The Journal of trauma 54: 848-859; discussion 859-861, 2003.

BAUER M, BAUER I, SONIN N V, KRESGE N, BAVEJA R, YOKOYAMA Y, HARDING D, ZHANG J X and CLEMENS M G: Functional significance of endothelin B receptors in mediating sinusoidal and extrasinusoidal effects of endothelins in the intact rat liver. Hepatology 31: 937-947, 2000.

BHATNAGAR M, PANDE M, DUBEY M P and DHAWAN B N: Effect of centhaquine on spontaneous and evoked norepinephrine release from isolated perfused rabbit heart. *Arzneimittelforschung* 35: 693-697, 1985.

BONANNO F G: Physiopathology of shock. Journal of emergencies, trauma, and shock 4: 222-232, 2011.

BOURQUE S L, DAVIDGE S T and ADAMS M A: The interaction between endothelin-1 and nitric oxide in the vasculature: new perspectives. American journal of physiology Regulatory, integrative and comparative physiology 300: R1288-1295, 2011.

BREUILLER-FOUCHE M, MORINIERE C, DALLOT E, OGER S, REBOURCET R, CABROL D and LEROY M J: Regulation of the endothelin/endothelin receptor system by interleukin-1{beta} in human myometrial cells. Endocrinology 146: 4878-4886, 2005.

BRIYAL S, NGUYEN C, LEONARD M and GULATI A (2015) Stimulation of endothelin B receptors by IRL-1620 decreases the progression of Alzheimer's disease, in Neuroscience pp 1-11.

BRUCE A J, BOLING W, KINDY M S, PESCHON J, KRAEMER P J, CARPENTER M K, HOLTSBERG F W and MATTSON M P: Altered neuronal and microglial responses to excitotoxic and ischemic brain injury in mice lacking TNF receptors. Nature medicine 2: 788-794, 1996.

BUEHLER P W, MEHENDALE S, WANG H, XIE J, M A L, TRIMBLE C E, HSIA C J and GULATI A: Resuscitative effects of polynitroxylated alphaalpha-cross-linked hemoglobin following severe hemorrhage in the rat. Free radical biology & medicine 29: 764-774, 2000.

CARDILLO C, KILCOYNE C M, CANNON R O, 3R D and PANZA J A: Interactions between nitric oxide and endothelin in the regulation of vascular tone of human resistance vessels in vivo. Hypertension 35: 1237-1241, 2000.

CHANG H, W U G J, WANG S M and HUNG C R: Plasma endothelin level changes during hemorrhagic shock. The Journal of trauma 35: 825-833, 1993.

CHAUDRY I H, AYALA A, ERTEL Wand STEPHAN R N: Hemorrhage and resuscitation: immunological aspects. The American journal of physiology 259: R663-678, 1990.

COWLEY A W, J R.: Renal medullary oxidative stress, pressure-natriuresis, and hypertension. Hypertension 52: 777-786, 2008.

DAVIS J W, KAUPS K L and PARKS S N: Base deficit is superior to pH in evaluating clearance of acidosis after traumatic shock. The Journal of trauma 44: 114-118, 1998.

EDWARDS J D, DOVGAN P S, ROWLEY J M, AGRAWAL D K, THORPE P E and ADRIAN T E: Endothelin-1 levels in ischaemia, reperfusion, and haemorrhagic shock in the canine infrarenal aortic revascularisation model. European journal of vascular surgery 8: 729-734, 1994.

EHRENREICH H, NAU T R, DEMBOWSKI C, HASSELBLATT M, BARTH M, HAHN A, SCHILLING L, SIREN A L and BRUCK W: Endothelin b receptor deficiency is associated with an increased rate of neuronal apoptosis in the dentate gyrus. Neuroscience 95: 993-1001, 2000.

FELLNER S K and ARENDSHORST W: Endothelin-A and -B receptors, superoxide, and Ca2+ signaling in afferent arterioles. Am J Physiol Renal Physiol 292: F175-184, 2007.

FONTANILLA C V, FAUNCE D E, GREGORY M S, MESSINGHAM K A, DURBIN E A, DUFFNER L A and KOVACS E J: Anti-interleukin-6 antibody treatment restores cell-mediated immune function in mice with acute ethanol exposure before burn trauma. Alcoholism, clinical and experimental research 24: 1392-1399, 2000.

FUHRMAN D Y, KANE-GILL S, GOLDSTEIN S L, PRIYANKA P and KELLUM J A: Acute kidney injury epidemiology, risk factors, and outcomes in critically ill patients 16-25 years of age treated in an adult intensive care unit. Ann Intensive Care 8: 26, 2018.

GADIENT R A, CRON K C and OTTEN U: Interleukin-1 beta and tumor necrosis factor-alpha synergistically stimulate nerve growth factor (NGF) release from cultured rat astrocytes. Neuroscience letters 117: 335-340, 1990.

GADO K, DOMJAN G, HEGYESI H and FALUS A: Role of INTERLEUKIN-6 in the pathogenesis of multiple myeloma. Cell biology international 24: 195-209, 2000.

GARDINER S M, KEMP P A, MARCH J E and BENNETT T: Effects of bosentan (Ro 47-0203), an ETA-, ETB-receptor antagonist, on regional haemodynamic responses to endothelins in conscious rats. British journal of pharmacology 112: 823-830, 1994.

GOTO K, KASUYA Y, MATSUKI N, TAKUWA Y, KURIHARA H, ISHIKAWA T, KIMURA S, YANAGISAWA M and MASAKI T: Endothelin activates the dihydropyridine-sensitive, voltage-dependent Ca2+ channel in vascular smooth muscle. Proceedings of the National Academy of Sciences of the United States of America 86: 3915-3918, 1989.

GULATI A, BRIYAL S, GANDHAKWALA R, KHAN M and LAVHALE M: Effect of centhaquin on endothelin receptors following resuscitation of hemorrhaged rat. Critical Care Medicine 44: 163, 2016a.

GULATI A, BRIYAL S, LAVHALE M S, GANDHAKWALA R and KHAN M: Endothelin Receptor Alteration Following Hemorrhagic Shock and Resuscitation by Centhaquin. Circulation 136: A20622, 2017.

GULATI A: Evidence for antagonistic activity of endothelin for clonidine induced hypotension and bradycardia. Life Sci 50: 153-160, 1992.

GULATI A, GOYAL A O, LAVHALE M S, GULATI S and SCHEETZ M: Human Pharmacokinetics of Centhaquin Citrate, a Novel Resuscitative Agent. Circulation 134 (Suppl 1): A16607-A16607, 2016.

GULATI A, LAVHALE M S, GARCIA D J and HAVALAD S: Centhaquin improves resuscitative effect of hypertonic saline in hemorrhaged rats. The Journal of surgical research 178: 415-423, 2012.

GULATI A, REBELLO S and KUMAR A: Role of sympathetic nervous system in cardiovascular effects of centrally administered endothelin-1 in rats. The American journal of physiology 273: H1177-1186, 1997a.

GULATI A and SEN A P: Dose-dependent effect of diaspirin cross-linked hemoglobin on regional blood circulation of severely hemorrhaged rats. Shock 9: 65-73, 1998.

GULATI A, SEN A P, SHARMA A C and SINGH G: Role of E T and N O in resuscitative effect of diaspirin cross-linked hemoglobin after hemorrhage in rat. The American journal of physiology 273: H827-836, 1997b.

GULATI A, SINGH R, CHUNG S M and SEN A P: Role of endothelin-converting enzyme in the systemic hemodynamics and regional circulatory effects of proendothelin-1 (1-38) and diaspirin cross-linked hemoglobin in rats. J Lab Clin Med 126: 559-570, 1995.

GULATI A and SRIMAL R C: Endothelin antagonizes the hypotension and potentiates the hypertension induced by clonidine. European journal of pharmacology 230: 293-300, 1993.

GULATI A, ZHANG Z, MURPHY A and LAVHALE M S: Efficacy of centhaquin as a small volume resuscitative agent in severely hemorrhaged rats. Am J Emerg Med 31: 1315-1321, 2013.

GUTIERREZ G, REINES H D and WULF-GUTIERREZ M E: Clinical review: hemorrhagic shock. Critical care 8: 373-381, 2004.

HAMA T, MIYAMOTO M, TSUKUI H, NISHIO C and HATANAKA H: Interleukin-6 as a neurotrophic factor for promoting the survival of cultured basal forebrain cholinergic neurons from postnatal rats. Neuroscience letters 104: 340-344, 1989.

HARRIS P J, ZHUO J, MENDELSOHN F A and SKINNER S L: Haemodynamic and renal tubular effects of low doses of endothelin in anaesthetized rats. The Journal of physiology 433: 25-39, 1991.

HELMY A, JALAN R, NEWBY D E, JOHNSTON N R, HAYES P C and WEBB D J: Altered peripheral vascular responses to exogenous and endogenous endothelin-1 in patients with well-compensated cirrhosis. Hepatology 33: 826-831, 2001.

HERCULE H C and OYEKAN A O: Cytochrome P450 omega/omega-1 hydroxylase-derived eicosanoids contribute to endothelin(A) and endothelin(B) receptor-mediated vasoconstriction to endothelin-1 in the rat preglomerular arteriole. The Journal of pharmacology and experimental therapeutics 292: 1153-1160, 2000.

HIRSCHBERG R, KOPPLE J, LIPSETT P, BENJAMIN E, MINEI J, ALBERTSON T, MUNGER M, METZLER M, ZALOGA G, MURRAY M, LOWRY S, CONGER J, MCKEOWN W, O'SHEA M, BAUGHMAN R, WOOD K, HAUPT M, KAISER R, SIMMS H, WARNOCK D, SUMMER W, HINTZ R, MYERS B, HAENFTLING K, CAPRA W and E T A L.: Multicenter clinical trial of recombinant human insulin-like growth factor I in patients with acute renal failure. Kidney Int 55: 2423-2432, 1999.

HOFFMAN A, ABASSI Z A, BRODSKY S, RAMADAN Rand WINAVER J: Mechanisms of big endothelin-1-induced diuresis and natriuresis: role of E T(B) receptors. Hypertension 35: 732-739, 2000.

INOUE A, YANAGISAWA M, KIMURA S, KASUYA Y, MIYAUCHI T, GOTO K and MASAKI T: The human endothelin family: three structurally and pharmacologically distinct isopeptides predicted by three separate genes. Proc Natl Acad Sci USA 86: 2863-2867, 1989.

JACOB M and KUMAR P: The challenge in management of hemorrhagic shock in trauma. Medical journal, Armed Forces India 70: 163-169, 2014.

JOCHEM J, ZWIRSKA-KORCZALA K, GWOZDZ B, WALICHIEWICZ P and JOSKO J: Cardiac and regional haemodynamic effects of endothelin-1 in rats subjected to critical haemorrhagic hypotension. Journal of physiology and pharmacology: an official journal of the Polish Physiological Society 54: 383-396, 2003.

KIM J Y, KAWABORI M and YENARI M A: Innate inflammatory responses in stroke: mechanisms and potential therapeutic targets. Current medicinal chemistry 21: 2076-2097, 2014.

KITAMURA K, TANAKA T, KATO J, OGAWA T, ETO T and TANAKA K: Immunoreactive endothelin in rat kidney inner medulla: marked decrease in spontaneously hypertensive rats. Biochemical and biophysical research communications 162: 38-44, 1989.

KOHAN D E, ROSSI N F, INSCHO E W and POLLOCK D M: Regulation of blood pressure and salt homeostasis by endothelin. Physiological reviews 91: 1-77, 2011.

KOMAROV P G, KOMAROVA E A, KONDRATOV R V, CHRISTOV-TSELKOV K, COON J S, CHERNOV M V and GUDKOV A V: A chemical inhibitor of p53 that protects mice from the side effects of cancer therapy. Science 285: 1733-1737, 1999.

KON V, YOSHIOKA T, FOGO A and ICHIKAWA I: Glomerular actions of endothelin in vivo. The Journal of clinical investigation 83: 1762-1767, 1989.

KOSSMANN T, HANS V, IMHOF H G, TRENTZ O and MORGANTI-KOSSMANN M C: Interleukin-6 released in human cerebrospinal fluid following traumatic brain injury may trigger nerve growth factor production in astrocytes. Brain research 713: 143-152, 1996.

KOWALCZYK A, KLENIEWSKA P, KOLODZIEJCZYK M, SKIBSKA Band GORACA A: The role of endothelin-1 and endothelin receptor antagonists in inflammatory response and sepsis. Archivum immunologiae et therapiae experimentalis 63: 41-52, 2015.

LAVHALE M S, BRIYAL S, PARIKH N and GULATI A: Endothelin modulates the cardiovascular effects of clonidine in the rat. Pharmacological research 62: 489-499, 2010.

LAVHALE M S, HAVALAD S and GULATI A: Resuscitative effect of centhaquin after hemorrhagic shock in rats. The Journal of surgical research 179: 115-124, 2013.

LAWRENCE E, SINEY L, WILSONCROFT P, KNOCK G A, TERENGHI G, POLAK J M and BRAIN S D: Evidence for ETA and ETB receptors in rat skin and an investigation of their function in the cutaneous microvasculature. Br J Pharmacol 115: 840-844, 1995.

LEONARD M G and GULATI A: Endothelin B receptor agonist, IRL-1620, enhances angiogenesis and neurogenesis following cerebral ischemia in rats. Brain research 1528: 28-41, 2013.

LIANGOS O, WALD R, O'BELL J W, PRICE L, PEREIRA B J and JABER B L: Epidemiology and outcomes of acute renal failure in hospitalized patients: a national survey. Clin J Am Soc Nephrol 1: 43-51, 2006.

LODGE N J, ZHANG R, HALAKA N N and MORELAND S: Functional role of endothelin ETA and ETB receptors in venous and arterial smooth muscle. European journal of pharmacology 287: 279-285, 1995.

LOWRY O H, ROSEBROUGH N J, FARR A L and RANDALL R J: Protein measurement with the Folin phenol reagent. The Journal of biological chemistry 193: 265-275, 1951.

MAGGI C A and MELI A: Suitability of urethane anesthesia for physiopharmacological investigations in various systems. Part 2: Cardiovascular system. Experientia 42: 292-297, 1986.

MARIK P E and FLEMMER M: The immune response to surgery and trauma: Implications for treatment. The journal of trauma and acute care surgery 73: 801-808, 2012.

MATHISON Y and ISRAEL A: Endothelin E T(B) receptor subtype mediates nitric oxide/cGMP formation in rat adrenal medulla. Brain Res Bull 45: 15-19, 1998.

MAZZONI M R, BRESCHI M C, CECCARELLI F, LAZZERI N, GIUSTI L, NIERI P and LUCACCHINI A: Suc-[Glu9, Ala11,15]-endothelin-1 (8-21), IRL 1620, identifies two populations of E T(B) receptors in guinea-pig bronchus. Br J Pharmacol 127: 1406-1414, 1999.

MEES S T, TOELLNER S, MARX K, FAENDRICH F, KALLEN K J, SCHROEDER J, HAIER J and KAHLKE V: Inhibition of interleukin-6-transsignaling via gp130-Fc in hemorrhagic shock and sepsis. The Journal of surgical research 157: 235-242, 2009.

MENG Z H, DYER K, BILLIAR T R and TWEARDY D J: Distinct effects of systemic infusion of G-CSF vs. IL-6 on lung and liver inflammation and injury in hemorrhagic shock.

Shock 14:41-48, 2000.

MICKLEY E J, GRAY G A and WEBB D J: Activation of endothelin ETA receptors masks the constrictor role of endothelin ETB receptors in rat isolated small mesenteric arteries. British journal of pharmacology 120: 1376-1382, 1997.

MOMMSEN P, BARKHAUSEN T, FRINK M, ZECKEY C, PROBST C, KRETTEK C and HILDEBRAND F: Productive capacity of alveolar macrophages and pulmonary organ damage after femoral fracture and hemorrhage in IL-6 knockout mice. Cytokine 53: 60-65, 2011.

MORAN A, TSIMELZON A I, MASTRANGELO M A, W U Y, Y U B, HILSENBECK S G, POLI V and TWEARDY D J: Prevention of trauma/hemorrhagic shock-induced lung apoptosis by IL-6-mediated activation of Stat3. Clinical and translational science 2: 41-49, 2009.

NAMAS R, GHUMA A, TORRES A, POLANCO P, GOMEZ H, BARCLAY D, GORDON L, ZENKER S, KIM H K, HERMUS L, ZAMORA R, ROSENGART M R, CLERMONT G, PEITZMAN A, BILLIAR T R, OCHOA J, PINSKY M R, PUYANA J C and VODO-VOTZ Y: An adequately robust early TNF-alpha response is a hallmark of survival following trauma/hemorrhage. PloS one 4: e8406, 2009.

O'DONNELL J N, GULATI A, LAVHALE M S, SHARMA S S, PATEL A J, RHODES N J and SCHEETZ M H: Pharmacokinetics of centhaquin citrate in a rat model. J Pharm Pharmacol 68: 56-62, 2016a.

O'DONNELL J N, O'DONNELL E P, KUMAR E J, LAVHALE M S, ANDURKAR S V, GULATI A and SCHEETZ M H: Pharmacokinetics of centhaquin citrate in a dog model. *J Pharm Pharmacol* 68: 803-809, 2016b.

OBERHOLZER A, OBERHOLZER C and MOLDAWER L L: Cytokine signaling—regulation of the immune response in normal and critically ill states. Critical care medicine 28: N3-12, 2000.

PACHER P, NAGAYAMA T, MUKHOPADHYAY P, BATKAI S and KASS D A: Measurement of cardiac function using pressure-volume conductance catheter technique in mice and rats. Nature protocols 3: 1422-1434, 2008.

PALADINO L, SINERT R, WALLACE D, ANDERSON T, YADAV K and ZEHTABCHI S: The utility of base deficit and arterial lactate in differentiating major from minor injury in trauma patients with normal vital signs. Resuscitation 77: 363-368, 2008.

PAPALEXOPOULOU K, CHALKIAS A, PLIATSIKA P, PAPALOIS A, PAPAPANAGIOTOU P, PAPADOPOU-LOS G, ARNAOUTOGLOU E, PETROU A, GULATI A and XANTHOS T: Centhaquin Effects in a Swine Model of Ventricular Fibrillation: Centhaquin and Cardiac Arrest. *Heart, Lung and Circulation* 26: 856-863, 2017.

PAPAPANAGIOTOU P, XANTHOS T, GULATI A, CHALKIAS A, PAPALOIS A, KONTOULI Z, ALEGA-KIS A and IACOVIDOU N: Centhaquin improves survival in a swine model of hemorrhagic shock. The Journal of surgical research 200: 227-235, 2016.

PEAKE N J, KHAWAJA K, MYERS A, NOWELL M A, JONES S A, ROWAN A D, CAWSTON T E and FOSTER H E: Interleukin-6 signalling in juvenile idiopathic arthritis is limited by proteolytically cleaved soluble interleukin-6 receptor. Rheumatology 45: 1485-1489, 2006.

PERNOW J, BOHM F, JOHANSSON B L, HEDIN U and RYDEN L: Enhanced vasoconstrictor response to endothelin-B-receptor stimulation in patients with atherosclerosis.

Journal of cardiovascular pharmacology 36: S418-420, 2000.

ROSSAINT R, CERNY V, COATS T J, DURANTEAU J, FERNANDEZ-MONDEJAR E, GORDINI G, STAHEL P F, HUNT B J, NEUGEBAUER E and SPAHN D R: Key issues in advanced bleeding care in trauma. Shock 26: 322-331, 2006.

SANCHEZ A, CONTRERAS C, MARTINEZ P, MUNOZ M, MARTINEZ A C, GARCIA-SACRISTAN A, HERNANDEZ M and PRIETO D: Endothelin A (E T(A)) receptors are involved in augmented adrenergic vasoconstriction and blunted nitric oxide-mediated relaxation of penile arteries from insulin-resistant obese zucker rats. J Sex Med 11: 1463-1474, 2014.

SANDOO A, VAN ZANTEN J J, METSIOS G S, CARROLL D and KITAS G D: The endothelium and its role in regulating vascular tone. The open cardiovascular medicine journal 4: 302-312, 2010.

SCHNEIDER M P, BOESEN E I and POLLOCK D M: Contrasting actions of endothelin E T(A) and E T(B) receptors in cardiovascular disease. Annual review of pharmacology and toxicology 47: 731-759, 2007.

SHACKFORD S R, MACKERSIE R C, HOLBROOK T L, DAVIS J W, HOLLINGSWORTH-FRIDLUND P, HOYT D B and WOLF P L: The epidemiology of traumatic death. A population-based analysis. Archives of surgery 128: 571-575, 1993.

SHARMA A C, SINGH G and GULATI A: Decompensation characterized by decreased perfusion of the heart and brain during hemorrhagic shock: role of endothelin-1. The Journal of trauma 53: 531-536, 2002.

SRIRAM K and O'CALLAGHAN J P: Divergent roles for tumor necrosis factor-alpha in the brain. Journal of neuroimmune pharmacology: the official journal of the Society on NeuroImmune Pharmacology 2: 140-153, 2007.

SUPAVEKIN S, ZHANG W, KUCHERLAPATI R, KASKEL F J, MOORE L C and DEVARAJAN P: Differential gene expression following early renal ischemia/reperfusion. *Kidney Int* 63: 1714-1724, 2003.

THAKALI K, GALLIGAN J J, FINK G D, GARIEPY C E and WATTS S W: Pharmacological endothelin receptor interaction does not occur in veins from E T(B) receptor deficient rats. Vascul Pharmacol 49: 6-13, 2008.

VASSILEVA, MOUNTAIN C and POLLOCK D M: Functional role of ETB receptors in the renal medulla. Hypertension 41: 1359-1363, 2003.

Journal of molecular and cellular cardiology 42: 620-630, 2007.

YEAGER M E, BELCHENKO D D, NGUYEN C M, COLVIN K L, IVY D D and STENMARK K R: Endothelin-1, the unfolded protein response, and persistent inflammation: role of pulmonary artery smooth muscle cells. American journal of respiratory cell and molecular biology 46: 14-22, 2012.

```
                      SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-Succinyl

<400> SEQUENCE: 1

Asp Glu Glu Ala Val Tyr Phe Ala His Leu Asp Ile Ile Trp
1               5                   10
```

VIDOVIC M, CHEN M M, LU Q Y, KALLONIATIS K F, MARTIN B M, TAN A H, LYNCH C, CROAKER G D, CASS D T and SONG Z M: Deficiency in endothelin receptor B reduces proliferation of neuronal progenitors and increases apoptosis in postnatal rat cerebellum. *Cell Mol Neurobiol* 28:1129-1138, 2008.

VINCENZI R, CEPEDA L A, PIRANI W M, SANNO-MYIA P, ROCHA ESM and CRUZ R J, JR.: Small volume resuscitation with 3% hypertonic saline solution decrease inflammatory response and attenuates end organ damage after controlled hemorrhagic shock. *Am J Surg* 198: 407-414, 2009.

VIRDIS A and SCHIFFRIN E L: Vascular inflammation: a role in vascular disease in hypertension? Current opinion in nephrology and hypertension 12: 181-187, 2003.

WHITE L R, JUUL R, SKAANES K O and AASLY J: Cytokine enhancement of endothelin E T(B) receptor-mediated contraction in human temporal artery. European journal of pharmacology 406: 117-122, 2000.

W U D, DAI H, ARIAS J, LATTA L and ABRAHAM W M: Low-volume resuscitation from traumatic hemorrhagic shock with Na$^+$/H$^+$ exchanger inhibitor. Critical care medicine 37: 1994-1999, 2009.

YANAGISAWA M, KURIHARA H, KIMURA S, TOMOBE Y, KOBAYASHI M, MITSUI Y, YAZAKI Y, GOTO K and MASAKI T: A novel potent vasoconstrictor peptide produced by vascular endothelial cells. Nature 332: 411-415, 1988.

YANG S, H U S, CHOUDHRY M A, RUE L W, 3R D, BLAND K I and CHAUDRY I H: Anti-rat soluble IL-6 receptor antibody down-regulates cardiac IL-6 and improves cardiac function following trauma-hemorrhage.

What is claimed is:

1. A method of treating an individual suffering acute kidney function decline comprising administering to the individual a therapeutically effective amount of a composition comprising centhaquin or a salt thereof.

2. The method of claim 1, wherein the acute kidney function decline is associated with acute kidney failure.

3. The method of claim 2, wherein the acute kidney failure is caused by or is associated with critical illness, reduced cardiac output, trauma, reduced blood oxygenation, systemic toxicity caused by reaction to injury in another organ, systemic hypotension resulting from cardiorenal syndrome, cardiac surgery or acute decompensated heart failure, a reduction in circulating volume due to hemorrhage, septic shock, hypovolemic shock, excessive dengue, a surgical procedure, rhabdomyolysis or a reduction in local renal blood flow resulting from hepatorenal syndrome or liver transplant, nephrotoxicity resulting from drugs, radiocontrast media, a non-steroidal anti-inflammatory drug (NSAID), an antibiotic, or a chemotherapeutic agent, or dehydration caused by diarrhea, vomiting, diuretics or excessive sweating.

4. The method of claim 1, wherein the salt is citrate, pyruvate, or lactate.

5. The method of claim 1, wherein the centhaquin or salt thereof is administered at a dose of about 0.0001 mg/kg to about 1.0 mg/kg.

6. The method of claim 5, wherein the centhaquin or salt thereof is administered in single or multiple doses.

7. The method of claim 4, wherein the salt is citrate.

8. The method of claim 5, wherein the centhaquin or salt thereof is administered at a dose of 0.0004 mg/kg to 0.5 mg/kg.

9. The method of claim 8, wherein the centhaquin or salt thereof is administered at a dose of 0.01 mg/kg.

10. The method of claim 9, wherein the centhaquin or salt thereof is coadministered with a resuscitation fluid, wherein the resuscitation fluid is a colloid solution, a crystalloid solution, blood, a blood component, or a blood substitute.

11. The method of claim 6, wherein the centhaquin or salt thereof is administered with an endothelin B (ETB) receptor agonist selected from the group consisting of N-Succinyl-[Glu$^9$, Ala$^{11,15}$] endothelin 1 (IRL-1620), BQ-3020, [Ala$^{1,3,11,15}$]-endothelin, sarafotoxin S6c, and endothelin 3.

12. The method of claim 11, wherein the endothelin B (ETB) receptor agonist is N-Succinyl-[Glu$^9$, Ala$^{11,15}$] endothelin 1 (IRL-1620).

13. The method of claim 12, wherein the ETB receptor agonist is administered at a dose ranging from 0.0001 mg/kg to 0.5 mg/kg.

14. The method of claim 13, wherein the method comprises administering multiple doses of the ETB receptor agonist.

15. The method of claim 13, wherein the method comprises administering a single dose of the ETB receptor agonist.

\* \* \* \* \*